(12) United States Patent
Hjálmarsson et al.

(10) Patent No.: US 11,357,237 B2
(45) Date of Patent: Jun. 14, 2022

(54) APPARATUS FOR PROCESSING AND GRADING FOOD ARTICLES AND RELATED METHODS

(71) Applicant: Valka EHF, Kopavogur (IS)

(72) Inventors: Helgi Hjálmarsson, Kopavogur (IS); Einar Bjorn Jonsson, Rekjavik (IS); Hannes Gunnarsson, Gardabaer (IS); Ingolfur Harri Hermannsson, Rekjavik (IS); Jon Eiriksson, Kopavogur (IS)

(73) Assignee: VALKA EHF, Kopavogur (IS)

( * ) Notice: Subject to any disclaimer, the term of this patent is extended or adjusted under 35 U.S.C. 154(b) by 38 days.

(21) Appl. No.: 16/567,903

(22) Filed: Sep. 11, 2019

(65) Prior Publication Data
US 2020/0077670 A1 Mar. 12, 2020

Related U.S. Application Data

(63) Continuation-in-part of application No. PCT/IB2018/057196, filed on Sep. 19, 2018, which is
(Continued)

(51) Int. Cl.
*A22C 17/00* (2006.01)
*B25J 9/00* (2006.01)
(Continued)

(52) U.S. Cl.
CPC ...... *A22C 17/0093* (2013.01); *A22C 17/0006* (2013.01); *A22C 17/008* (2013.01);
(Continued)

(58) Field of Classification Search
CPC ............ A22C 17/0093; A22C 17/0006; A22C 17/008; B25J 11/045; B25J 11/055; B07C 5/368; B07C 5/36
(Continued)

(56) References Cited

U.S. PATENT DOCUMENTS

| 512,182 A | 1/1894 | Scheurer |
| 1,496,376 A | 6/1924 | Perley |
(Continued)

FOREIGN PATENT DOCUMENTS

| CN | 101498601 B | 4/2011 |
| DE | 3302718 A1 | 9/1983 |
(Continued)

OTHER PUBLICATIONS

International Search Report and Written Opinion for International application No. PCT/EP2019/074281 filed Sep. 11, 2019, 13 pages.
(Continued)

*Primary Examiner* — Richard T Price, Jr.
(74) *Attorney, Agent, or Firm* — Morrison & Foerster LLP

(57) ABSTRACT

This disclosure relates to apparatuses and methods for processing and grading food articles. For example, provided herein is a system for grading a portioned food article, in which the system includes: a first conveyor; a first receiving conveyor and a second receiving conveyor, defining a space therebetween; at least one spray-removal robot; and a third receiving conveyor. The spray-removal robot may include at least one valve with a nozzle, in which the valve ejects fluid through the nozzle to impact a food article being moved on the first conveyor toward the third receiving conveyor, such that at least one portion of the food article is moved by the impact through the space between the first receiving conveyor and the second receiving conveyor, and such that at least one portion of the food article is moved by the first receiving conveyor and the second receiving conveyor to the third receiving conveyor.

20 Claims, 36 Drawing Sheets

Related U.S. Application Data a continuation-in-part of application No. PCT/IB2016/051192, filed on Mar. 2, 2016.

(60) Provisional application No. 62/729,781, filed on Sep. 11, 2018, provisional application No. 62/560,620, filed on Sep. 19, 2017, provisional application No. 62/127,150, filed on Mar. 2, 2015, provisional application No. 62/255,963, filed on Nov. 16, 2015.

(51) Int. Cl.
  *B25J 11/00* (2006.01)
  *G01N 33/12* (2006.01)

(52) U.S. Cl.
  CPC ......... *B25J 9/0093* (2013.01); *B25J 11/0045* (2013.01); *B25J 11/0055* (2013.01); *G01N 33/12* (2013.01)

(58) Field of Classification Search
  USPC .......................................... 452/150, 177–184
  See application file for complete search history.

(56) References Cited

U.S. PATENT DOCUMENTS

| | | |
|---|---|---|
| 1,706,734 A | 3/1929 | Hughes |
| 2,168,419 A | 8/1939 | Paterson |
| 2,377,123 A | 5/1945 | Leslie et al. |
| 3,319,766 A | 5/1967 | Crosby et al. |
| 3,561,552 A | 2/1971 | Rischke |
| 3,656,617 A | 4/1972 | De Bie |
| 3,756,374 A | 9/1973 | Burt et al. |
| 3,872,695 A | 3/1975 | Busek |
| 4,008,888 A | 2/1977 | Vinciguerra |
| 4,106,174 A | 8/1978 | Ilines |
| 4,122,941 A | 10/1978 | Giles et al. |
| 4,308,928 A | 1/1982 | Oshima et al. |
| 4,310,276 A | 1/1982 | Castagnoli |
| 4,344,493 A | 8/1982 | Salmonsen et al. |
| 4,358,009 A | 11/1982 | Rysti |
| 4,381,582 A | 5/1983 | Korhonen |
| 4,398,612 A | 8/1983 | Mikami et al. |
| 4,421,185 A | 12/1983 | Koto et al. |
| 4,428,179 A | 1/1984 | Jordan et al. |
| 4,442,910 A | 4/1984 | Mikami |
| 4,483,047 A | 11/1984 | Linville, Jr. |
| 4,557,019 A | 12/1985 | Van Devanter et al. |
| 4,561,510 A | 12/1985 | Sugioka et al. |
| 4,564,103 A | 1/1986 | Sashiki et al. |
| 4,570,831 A | 2/1986 | Izumi et al. |
| 4,600,096 A | 7/1986 | Yamano et al. |
| 4,603,768 A | 8/1986 | Deutschle |
| 4,615,403 A | 10/1986 | Nakamura |
| 4,619,359 A | 10/1986 | Kennedy, Jr. et al. |
| 4,632,254 A | 12/1986 | Scopatz |
| 4,662,508 A | 5/1987 | Inoue et al. |
| 4,681,176 A | 7/1987 | Moran et al. |
| 4,708,215 A | 11/1987 | Nakamura et al. |
| 4,720,961 A | 1/1988 | Jordan |
| 4,748,724 A | 6/1988 | Lapeyre et al. |
| 4,758,778 A | 7/1988 | Kristinsson |
| 4,765,488 A | 8/1988 | Moriarity |
| 4,821,820 A | 4/1989 | Edwards et al. |
| 4,843,561 A | 6/1989 | Larson |
| 4,870,799 A | 10/1989 | Bergerioux et al. |
| 4,874,049 A | 10/1989 | Kee et al. |
| 4,911,281 A | 3/1990 | Jenkner |
| 4,962,568 A | 10/1990 | Rudy et al. |
| 4,963,251 A | 10/1990 | Bohm et al. |
| 4,970,757 A | 11/1990 | Heiland et al. |
| 5,054,831 A | 10/1991 | Ting et al. |
| 5,162,016 A | 11/1992 | Malloy |
| 5,205,779 A | 4/1993 | O'Brien et al. |
| 5,247,761 A | 9/1993 | Miles et al. |
| 5,318,173 A | 6/1994 | Datari |
| 5,340,949 A | 8/1994 | Fujimura et al. |
| 5,403,056 A | 4/1995 | Wallace |
| 5,429,223 A | 7/1995 | Moeller |
| 5,501,313 A | 3/1996 | Bonnet |
| 5,613,595 A | 3/1997 | Ukada |
| 5,626,236 A | 5/1997 | Hiebert |
| 5,699,896 A | 12/1997 | Spada et al. |
| 5,813,195 A | 9/1998 | Nielsen et al. |
| 5,842,306 A | 12/1998 | Onosaka et al. |
| 5,957,306 A | 9/1999 | Hoffman |
| 5,998,740 A | 12/1999 | Kvisgaard et al. |
| 6,002,125 A | 12/1999 | Schubert |
| 6,015,049 A | 1/2000 | Heikes |
| 6,122,895 A | 9/2000 | Schubert |
| 6,124,560 A | 9/2000 | Roos et al. |
| 6,126,017 A | 10/2000 | Hours |
| 6,234,300 B1 | 5/2001 | De Vos et al. |
| 6,321,135 B1 | 11/2001 | Asgeirsson |
| 6,388,209 B1 | 5/2002 | Gudmundsson |
| 6,407,346 B1 | 6/2002 | Baker |
| 6,437,256 B1 | 8/2002 | Miyamoto |
| 6,444,926 B1 | 9/2002 | Ricciardi, Sr. |
| 6,493,605 B1 | 12/2002 | Prideaux et al. |
| 6,640,158 B1 | 10/2003 | Brandt, Jr. |
| 6,787,712 B2 | 9/2004 | Asai et al. |
| 6,955,031 B2 | 10/2005 | Doake et al. |
| 7,057,118 B2 | 6/2006 | Arnason et al. |
| 7,080,739 B2 | 7/2006 | Guy et al. |
| 7,240,465 B2 | 7/2007 | Davi' et al. |
| 7,252,584 B2 | 8/2007 | Kragh |
| 7,258,237 B2 | 8/2007 | Nielsen |
| 7,323,643 B2 | 1/2008 | Hjalmarsson |
| 7,368,670 B2 | 5/2008 | Hjalmarsson |
| 7,395,934 B2 | 7/2008 | Gudjonsson |
| 7,452,266 B2 | 11/2008 | Bottemiller |
| 7,715,935 B2 | 5/2010 | Vogeley, Jr. et al. |
| 7,904,198 B2 | 3/2011 | Hawes |
| 7,967,149 B2 | 6/2011 | Helgi |
| 8,158,895 B2 | 4/2012 | Grundtvig et al. |
| 8,662,314 B2 | 3/2014 | Jones et al. |
| 9,079,223 B2 | 7/2015 | Bjornsson et al. |
| 9,095,147 B2 | 8/2015 | Hjalmarsson et al. |
| 2002/0067797 A1 | 6/2002 | Safai et al. |
| 2002/0071038 A1 | 6/2002 | Mihelcic |
| 2003/0052049 A1 | 3/2003 | Franc |
| 2004/0022930 A1 | 2/2004 | Skjervold et al. |
| 2004/0231480 A1 | 11/2004 | Wattles et al. |
| 2005/0032471 A1 | 2/2005 | Pfarr et al. |
| 2005/0085176 A1 | 4/2005 | Houtz |
| 2005/0137744 A1 | 6/2005 | Winkelmolen et al. |
| 2005/0147325 A1 | 7/2005 | Chen et al. |
| 2006/0161380 A1 | 7/2006 | Bottemiller |
| 2006/0162515 A1 | 7/2006 | Vogeley et al. |
| 2006/0182603 A1 | 8/2006 | Hawes |
| 2007/0039763 A1 | 2/2007 | Hjalmarsson |
| 2007/0144792 A1 | 6/2007 | Hjalmarsson |
| 2007/0290516 A1 | 12/2007 | Buljo |
| 2009/0026119 A1 | 1/2009 | Hjalmarsson |
| 2009/0057098 A1 | 3/2009 | Helgi |
| 2009/0145670 A1 | 6/2009 | Grundtvig et al. |
| 2009/0170417 A1 | 7/2009 | Janssen et al. |
| 2009/0216368 A1 | 8/2009 | Thorsson |
| 2009/0238670 A1 | 9/2009 | Helgi et al. |
| 2009/0301940 A1 | 12/2009 | Elvarsson et al. |
| 2010/0101191 A1 | 4/2010 | Lindee |
| 2012/0150339 A1 | 6/2012 | Bjornsson et al. |
| 2012/0307013 A1 | 12/2012 | Hjalmarsson et al. |
| 2017/0028429 A1* | 2/2017 | Linares .................. B05B 16/20 |
| 2018/0009105 A1* | 1/2018 | Kutsukake ............. B25J 9/0093 |
| 2018/0065135 A1* | 3/2018 | Linares ................. B05B 14/465 |
| 2019/0000094 A1 | 1/2019 | Hjalmarsson et al. |
| 2019/0337167 A1* | 11/2019 | Clifford .................. B05B 14/40 |
| 2020/0288731 A1 | 9/2020 | Hjalmarsson et al. |

FOREIGN PATENT DOCUMENTS

| | | |
|---|---|---|
| DE | 4413967 A | 11/1994 |
| DE | 69104122 T2 | 3/1995 |

(56) References Cited

FOREIGN PATENT DOCUMENTS

| | | |
|---|---|---|
| DE | 20203818 U1 | 5/2002 |
| DE | 202004001567 U1 | 2/2005 |
| DE | 102004056031 A1 | 5/2006 |
| DE | 102006061571 A1 | 7/2008 |
| DE | 202011110569 U1 | 10/2014 |
| EP | 734653 A | 10/1996 |
| EP | 761322 A1 | 3/1997 |
| EP | 1074822 A2 | 2/2001 |
| EP | 1687599 B1 | 4/2007 |
| EP | 1819994 B1 | 10/2008 |
| EP | 1896196 B1 | 12/2010 |
| EP | 3178571 A1 | 6/2017 |
| FR | 2454338 A1 | 11/1980 |
| FR | 2595589 A1 | 9/1987 |
| FR | 2744984 A1 | 8/1997 |
| FR | 2754239 A1 | 4/1998 |
| GB | 242848 A | 11/1925 |
| GB | 483949 A | 4/1938 |
| GB | 2116732 B | 2/1986 |
| GB | 2405081 A | 2/2005 |
| GB | 2415944 A | 1/2006 |
| JP | S6031421 A | 2/1985 |
| JP | S62249818 A | 10/1987 |
| JP | H07256582 A | 10/1995 |
| JP | H0882546 A | 3/1996 |
| JP | H09224935 A | 9/1997 |
| WO | WO-1989008983 A1 | 10/1989 |
| WO | WO-1993016849 A1 | 9/1993 |
| WO | WO-1995035238 A1 | 12/1995 |
| WO | WO-1996008322 A1 | 3/1996 |
| WO | WO-1999044759 A1 | 9/1999 |
| WO | WO-2000022934 A1 | 4/2000 |
| WO | WO-2000023771 A1 | 4/2000 |
| WO | WO-2000023772 A1 | 4/2000 |
| WO | WO-2001007324 A1 | 2/2001 |
| WO | WO-2001010574 A1 | 2/2001 |
| WO | WO-2001022043 A2 | 3/2001 |
| WO | WO-2001027567 A2 | 4/2001 |
| WO | WO-2002043502 A2 | 6/2002 |
| WO | WO-2003008917 A1 | 1/2003 |
| WO | WO-2003069285 A2 | 8/2003 |
| WO | WO-2004090481 A1 | 10/2004 |
| WO | WO-2005051812 A1 | 6/2005 |
| WO | WO-2005062994 A2 | 7/2005 |
| WO | WO-2005085776 A1 | 9/2005 |
| WO | WO-2005095904 A1 | 10/2005 |
| WO | WO-2005102620 A1 | 11/2005 |
| WO | WO-2006064521 A1 | 6/2006 |
| WO | WO-2006092311 A1 | 9/2006 |
| WO | WO-2006106532 A1 | 10/2006 |
| WO | WO-2007022782 A2 | 3/2007 |
| WO | WO-2007083327 A2 | 7/2007 |
| WO | WO-2007134603 A1 | 11/2007 |
| WO | WO-2008095500 A2 | 8/2008 |
| WO | WO-2016139611 A2 | 9/2016 |
| WO | WO-2019058262 A1 | 3/2019 |
| WO | WO-2020053310 A1 | 3/2020 |
| WO | WO-2020225364 A1 | 11/2020 |

OTHER PUBLICATIONS

International Preliminary Report on Patentability for International Application No. PCT/IB2016/051192, dated Sep. 5, 2017, 11 pages.
International Search Report and Written Opinion for International application No. PCT/EP2019/074281 filed Feb. 17, 2020, 9 pages.
International Search Report and Written Opinion for International Application No. PCT/IB2016/051192, dated Sep. 12, 2016, 16 pages.
International Search Report and Written Opinion for International Application No. PCT/IB2018/057196, dated Jan. 7, 2019, 11 pages.
Unpublished U.S. Appl. No. 17/275,599, filed Mar. 11, 2021 titled "Apparatus for Processing and Grading Food Articles and Related Methods," (Copy not submitted herewith pursuant to the waiver of 37 C.F.R. § 1.98(a)(2)(iii)).
Certified priority document of International Patent Application No. PCT/IS2006/000008 internationally filed Apr. 4, 2006, 12 pages.
Extended European Search Report for European Patent Application No. EP 1000150.9, completed on Jul. 28, 2010, 7 pages.
International Search Report and Written Opinion for International Application No. PCT/EP2020/062716, dated Jul. 21, 2020, 10 pages.
International Search Report and Written Opinion for International Application No. PCT/IS2004/000014, dated Nov. 18, 20004, 8 pages.
International Search Report and Written Opinion for International Application No. PCT/IS2005/000006, dated Jun. 15, 2005, 8 pages.
International Search Report and Written Opinion for International Application No. PCT/IS2007/000003, dated Sep. 11, 2007, 12 pages.
International Search Report and Written Opinion for International Application No. PCT/IS2007/000004, dated Sep. 13, 2007, 13 pages.
International Search Report and Written Opinion for International Application No. PCT/IS2007/000013, dated Nov. 30, 2007, 10 pages.
International Search Report for International Application No. PCT/IB2010/002109, dated Nov. 30, 2010, 4 pages.
International Search Report for PCT/IS2011/000001, Completed by the European Patent Office dated Jun. 27, 2011, 2 Pages.
Unpublished U.S. Appl. No. 17/609,280, filed May 7, 2020 titled "Conveyor System and Method," (Copy not submitted herewith pursuant to the waiver of 37 C.F.R. § 1.98(a)(2)(iii)).

* cited by examiner

APPARATUS FOR PROCESSING AND GRADING FOOD ARTICLES AND RELATED METHODS

RELATED APPLICATIONS

This application claims the benefit of priority from U.S. Provisional Application No. 62/729,781, filed on Sep. 11, 2018.

FIELD OF THE DISCLOSURE

Embodiments of the disclosure generally relate to apparatuses and methods for processing and grading food articles, for example, based on at least one characteristic of the food articles, wherein the grading comprises arranging the food articles along a conveyor and/or grading the articles onto one or more receiving areas.

BACKGROUND

Conventional grading machines include arms and/or trays to grade food articles while the food articles move along a conveyor. Food articles are often graded based on different characteristics, such as weight. Such methods often require several human participants to double check automatic procedures performed by machines, or to perform additional actions not performed by machines.

For example, U.S. Pat. No. 7,258,237 describes a grading technique that includes weighing and portioning an item. In the grading technique, natural foodstuff items with varying weights are subjected to a weighing-in, and are thereafter selectively fed together in a computer controlled manner. According to this reference, a robot device including a grip, operated by a control system, is used for removing items from a delivery station to a receiving area for placement into a particular batch.

Similar methods for poultry packaging are described in "Robotic Packaging of Poultry products, by K. Khodabandehloo, Department of Mechanical Engineering, University of Bristol ISBN 0442316615 (Routledge, 1992)" and "Benefits of Experts robots intelligence vs. Skill, by K. Khodabandehloo, Department of Mechanical Engineering, University of Bristol ISBN 0387537317 (Routledge, 1992)". The previous references disclose a robot used to place poultry portions into trays according to a defined scheme.

BRIEF SUMMARY OF THE DISCLOSURE

This summary is provided to introduce a selection of concepts in a simplified form. These concepts are described in further detail in the detailed description of example embodiments of the disclosure below. This Summary is not intended to identify key features or essential features of the claimed subject matter, nor is it intended to be used to limit the scope of the claimed subject matter.

Applicants have discovered that one disadvantage of having a robot arm picking the articles up from a conveyor is that it is difficult to design a good gripper arm to handle (e.g., grasp) delicate food products that typically come in various sizes. If the gripper arm is big enough for the biggest articles, it will require significantly more space between small articles than would otherwise be needed. Furthermore, such gripping robotic arms are not able to grasp articles that are oriented very close to each other on the conveyor. For example, such gripping robotic arms would not be able to grasp fish portions that are cut prior to being graded, but wherein the cut portions are still in the shape of the original fillet, without disturbing or even damaging the surrounding portions.

Embodiments herein include methods for grading food articles on a surface, and/or robots and apparatus. The surface may be a conveyor having an in-feed end and an out-feed end. Some embodiments comprise cutting a food article (e.g., a fish fillet) into a plurality of portions that are bisected by a line that is parallel to the in-feed end and/or the out-feed end of the conveyor. In embodiments, each portion of a plurality of portions may have an alignment and orientation. Grading a portion of the plurality of portions may include moving at least one portion of the plurality of portions, while at least substantially maintaining the alignment and orientation of each portion of the plurality of portions. In particular examples, moving the at least one portion may remove the portion(s) from a surface whereupon the portions are disposed.

In some embodiments, a method for grading food articles includes cutting a food article into a plurality of portions oriented parallel to each other. Some examples include grading at least one of the plurality of portions that is oriented parallel to at least another of the plurality of portions, wherein the at least another of the plurality of portions is/are not graded. Some examples comprise grading at least one of the plurality of portions that is positioned on the conveyor such that each side of the at least one portion(s) is proximate a side of at least one adjacent portion; e.g., a cut portion is graded from within the middle of the shape of the original food article.

In some embodiments, a food article is cut into the plurality of portions, such that the cut portions are oriented very close to each other on the conveyor (for example, wherein the cut portions are separated by a space that is essentially the width of a blade of the cutting instrument). In some examples, at least one of the very closely oriented portions is graded without damaging and/or changing the orientation and/or alignment of the other portion(s) on the conveyor.

In particular embodiments, a method for grading food articles comprises at least one step selected from the group consisting of: capturing a first x-ray image of a food article; detecting at least a first portion of the food article to be removed, and at least a second portion of the food article to retain using the first x-ray image; cutting the first portion of the food article away from the second portion of the food article; moving the first portion of the food article automatically with a machine; and capturing a second x-ray image of the second portion of the food article. Certain examples include a method comprising all of the foregoing steps.

In particular embodiments, a method for grading food articles comprises at least one step selected from the group consisting of: cutting a food article into a plurality of portions oriented parallel to each other, wherein each portion has an alignment and orientation; capturing an x-ray image of the plurality of portions oriented parallel to each other; and moving less than all of the plurality of portions automatically with a machine. Some examples comprise detecting which portions of the plurality of portions contain an undesirable component of the portion (for example, with a first x-ray machine); and moving only portions of the plurality of portions containing an undesirable component. In particular examples, the undesirable component is selected from the group consisting of bones (i.e., a bone or bone fragment), cartilage, fat, defects in flesh, tough tissues, skin, blood, and organs. In certain examples, the undesirable component is a bone. In certain embodiments, at least one detected portion containing an undesirable component is moved automatically, and any remaining portion(s) comprising a further undesirable component are detected (for example, in a second x-ray machine).

Some embodiments include a grading device (i.e., a robot), which grading device may have any number of degrees of freedom. In particular embodiments, the grading device may comprise a horizontally movable support member; a vertically movable support member slidably coupled to the horizontally movable support member; a first actuator attached to the horizontally movable support member; a second actuator attached to the vertically movable support member; and a means for moving at least one portion of a food article attached to the vertically movable support member (e.g., a needle array, and a gripper). In some examples, the means for moving at least one portion of a food article may be utilized to move a plurality of portions at substantially the same time (i.e., in one movement of the grading device).

Some embodiments include an automated food processing system that contains, in sequential order on a conveyor, a first x-ray machine, at least one cutting machine, and a second x-ray machine. In some embodiments, the cutting machine(s) is adapted to cut out a portion containing a bone or bone fragment from a food article, leaving one or more portions of the food article containing flesh. In some examples, the automated food processing system comprises computer programming to utilize information from the second x-ray machine to locate a bone or bone fragment in a food article portion, and a computer adapted to adjust the operation of the cutting machine(s) according to the location of a bone or bone fragment in a portion of a food article, so as to maximize the size of the one or more portions of the food article containing flesh that remain(s) after cutting. In particular examples, the automated food processing system comprises at least one grading device (e.g., one, two, three, four, five, or more grading devices) that is adapted to move a portion of the food article containing bones after cutting, as determined by the second x-ray machine; for example, to reposition the portion on the conveyor before the cutting machine(s), or to remove the portion from the conveyor. The grading device(s) may be positioned anywhere in the automated food processing system; for example, following an x-ray machine or conveyor.

In some embodiments, an automated food processing system comprises computer programming to utilize information from the first x-ray machine to locate a bone or bone fragment in a food article portion. In particular examples, the automated food processing system comprises at least one grading device that is adapted to move a portion of the food article containing bones after cutting, as determined by the first x-ray machine; for example, to reposition the portion on the conveyor before the cutting machine(s), or to remove the portion from the conveyor.

In some embodiments, the grading robot may include a first mounting member mounted to a side of a grading conveyor and a second mounting member mounted to a side of the grading conveyor (for example, a side other than that to which the first mounting member is mounted). The grading robot may include a first guide member horizontally mounted to both the first mounting member and the second mounting member, and a horizontally movable support member slidably coupled to the first guide member. The grading robot may include a second guide member mounted to the horizontally movable support member, and a vertically movable support member slidably coupled to the second guide member. The grading robot may in some examples comprise at least one additional actuator, so as to provide at least one additional degree of freedom. Furthermore, the grading robot may include a first actuator (e.g., air cylinder, motor, linear motor, traditional motor, and solenoid) attached at one end to the horizontally movable support member. The first actuator may be attached at another end to the second mounting member. The grading robot may include a second actuator attached at one end to the second guide member. The second actuator may be attached at another end to the vertically movable support member. In some examples, a grading robot may include at least one needle or gripper attached to the vertically movable support member.

Some embodiments include at least one realigning apparatus for aligning food article. In particular embodiments, a realigning apparatus for aligning a food article or portion of a food article may comprise a first mini-conveyor; a second mini-conveyor disposed proximate the first mini-conveyor; a first actuator attached to the first mini-conveyor; and a second actuator attached to the second mini-conveyor, wherein the first mini-conveyor is mounted with a hinge such that the first mini-conveyor is separable from the second mini-conveyor. In some embodiments, a realigning apparatus may include a first mini-conveyor disposed above a processing conveyor, and a second mini-conveyor disposed above the processing conveyor proximate the first mini conveyor. Both the first mini-conveyor and second mini-conveyor may be tilted at an angle, such that the first mini-conveyor and second mini-conveyor form a V-shape.

Some embodiments include a food processing apparatus. In particular embodiments, a food processing apparatus comprises at least one conveyor; at least one grading device (e.g, a robot); and at least one imaging system, at least one cutting machine, and/or at least one realigning apparatus. In particular embodiments, the food processing apparatus comprises at least one of: x-ray machine(s), manual quality check station(s), automated quality check station(s), and realigning apparatus. Certain embodiments include a food processing apparatus comprising at least one conveyor; at least one x-ray machine; a first imaging system; at least one cutting machine; at least one quality check station; at least one additional imaging system; at least one grading device; at least one realigning apparatus; and at least one computer programmed to utilize information from the additional imaging system(s) to determine, for example, the location of a bone or bone fragment in a portion of a food article, the location of fat in a portion of a food article, the color of a portion of a food article, the location of a gap in a portion of a food article, the location of a visual defect in a portion of a food article, and the location of parasites in a portion of a food article, wherein the computer is programmed to utilize information about the movement of the at least one conveyor and any determined feature to adjust the position of the means for moving at least one portion of a food article of the grading device.

BRIEF DESCRIPTION OF THE DRAWINGS

The present disclosure may be understood more fully by reference to the following Detailed Description of several embodiments, which are illustrated in the appended figures, in which:

Referring to FIG. 1, portions 117 "three," "six," and "seven" are portions 117 that are positioned such that each side is proximate a side of at least one adjacent portion 117. Referring again to FIG. 1, portions 117 "one" and "eight" are in series with portion 117 "three," and portions 117 "two" and "four" are parallel to portion 117 "three."

FIG. 4(A-B) includes perspective views of illustrative cutting machines of a food processing apparatus.

FIG. 6(C-D) include perspective views of a representative means for moving at least one portion of a food article attached to a vertically movable support member. In this particular example, the means for moving at least one portion of a food article attached to a vertically movable support member is an example of a needle array attached to a lowermost portion of a vertically movable support member.

FIG. 8(A-C) also illustrates means for the removal of a portion 117 that has already been cut from a fillet 101 by the operation of a spray-removal robot 651 in a spray-removal grading section of a food processing apparatus 200.

FIGS. 9(F-G) include perspective views of a two degrees of freedom grading robot comprising a first, splitting plate in the direction perpendicular to the conveyor, and a second plate at the end of the first, splitting plate that can be rotated.

FIGS. 9(I-K) include perspective views of a four degrees of freedom grading robot. FIGS. 9(J-K) specifically include perspective views of a four degrees of freedom grading robot comprising two means for moving at least one portion of a food article. In this example, the two means for moving at least one portion of a food article can rotate around an axis that is parallel to the conveyor plane. Referring to FIGS. 9(I-J), a first means for moving at least one portion of a food article grips a portion of the food article (the pinbone portion of a fish fillet in the illustration of FIG. 9J).

FIG. 10(A-B) includes perspective views of illustrative realigning sections of a food processing apparatus.

FIG. 11(A-C) shows a system including three conveyors. The conveyor furthest to the left is the first conveyor (e.g., an x-ray conveyor) in the conveyor's direction of movement. The second conveyor from the left may be a retractable infeed conveyor. The conveyor furthest to the right may also be a retractable infeed conveyor; for example, where a person stands to ensure that food articles are properly oriented, and/or would that there is a desired spacing between the food articles (e.g., from overlapping (less than 0 mm) to 100 mm, from adjacent (0 mm) to 100 mm, from about 10 mm to 100 mm, and about 10 mm). The outfeed end of the first conveyor and the infeed end of the second conveyor move together in the conveyor's direction of movement as shown with the blue arrow. There may be a product sensor (e.g., an imaging device) associated with the first conveyor that measures the distance between the food articles on the conveyor. For example, the product sensor may first measure the distance between consecutive food articles on the conveyor.

Figure 11A:
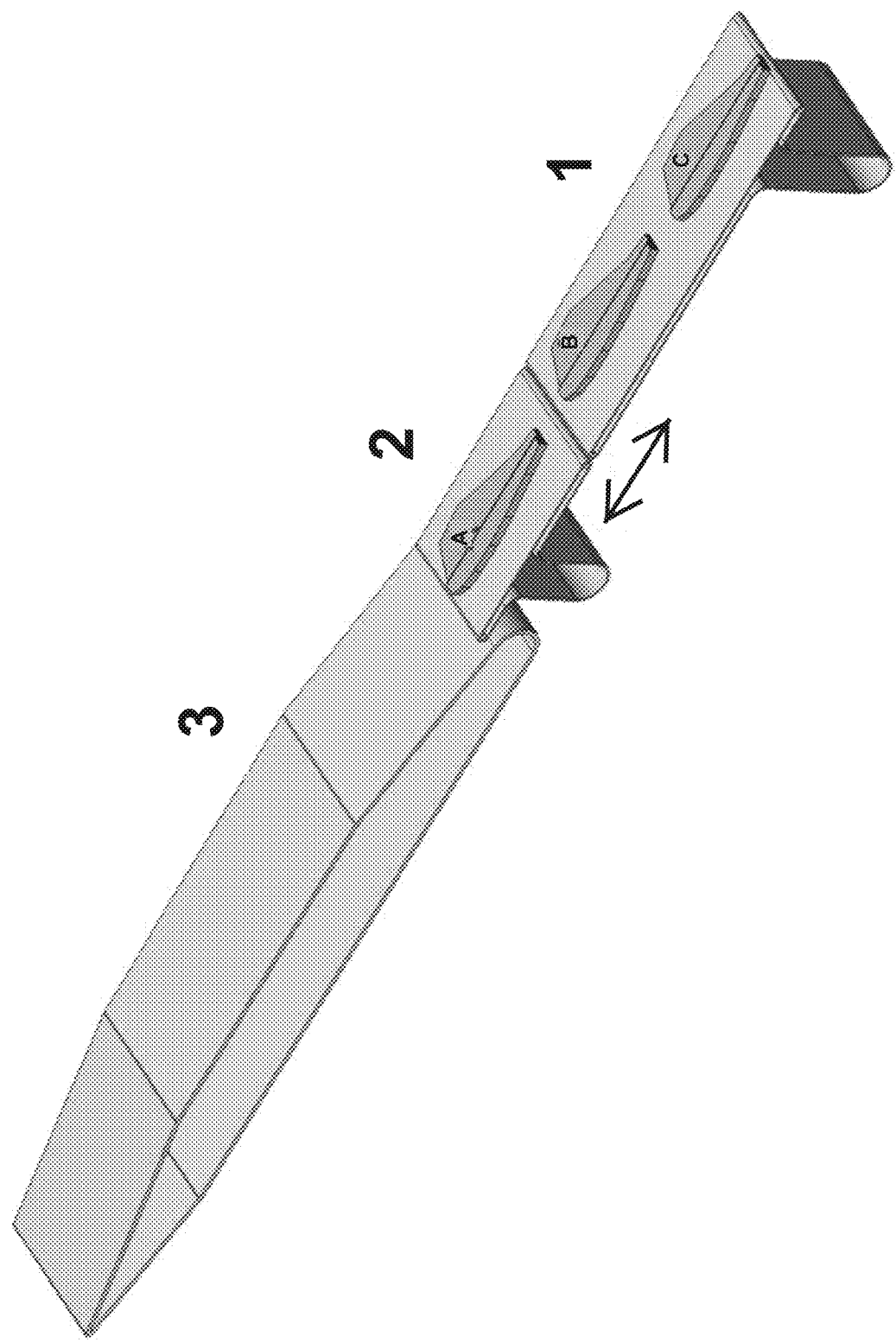
FIG. 11(A-C) includes perspective views of a representative system that may be used to align food articles in some embodiments.

In the example shown in FIG. 11A, the spacing between food article A and food article B is higher (e.g., more than 100 mm) than the desired spacing (e.g., about 10 mm). In this case, the system will wait until food article A has reached the second conveyor, and then it will move the outfeed end of the first conveyor and the infeed end of the second conveyor at the same time, until the spacing between food article A and food article B is close to the desired spacing (e.g., approximately or exactly the desired spacing).

Figure 11B:
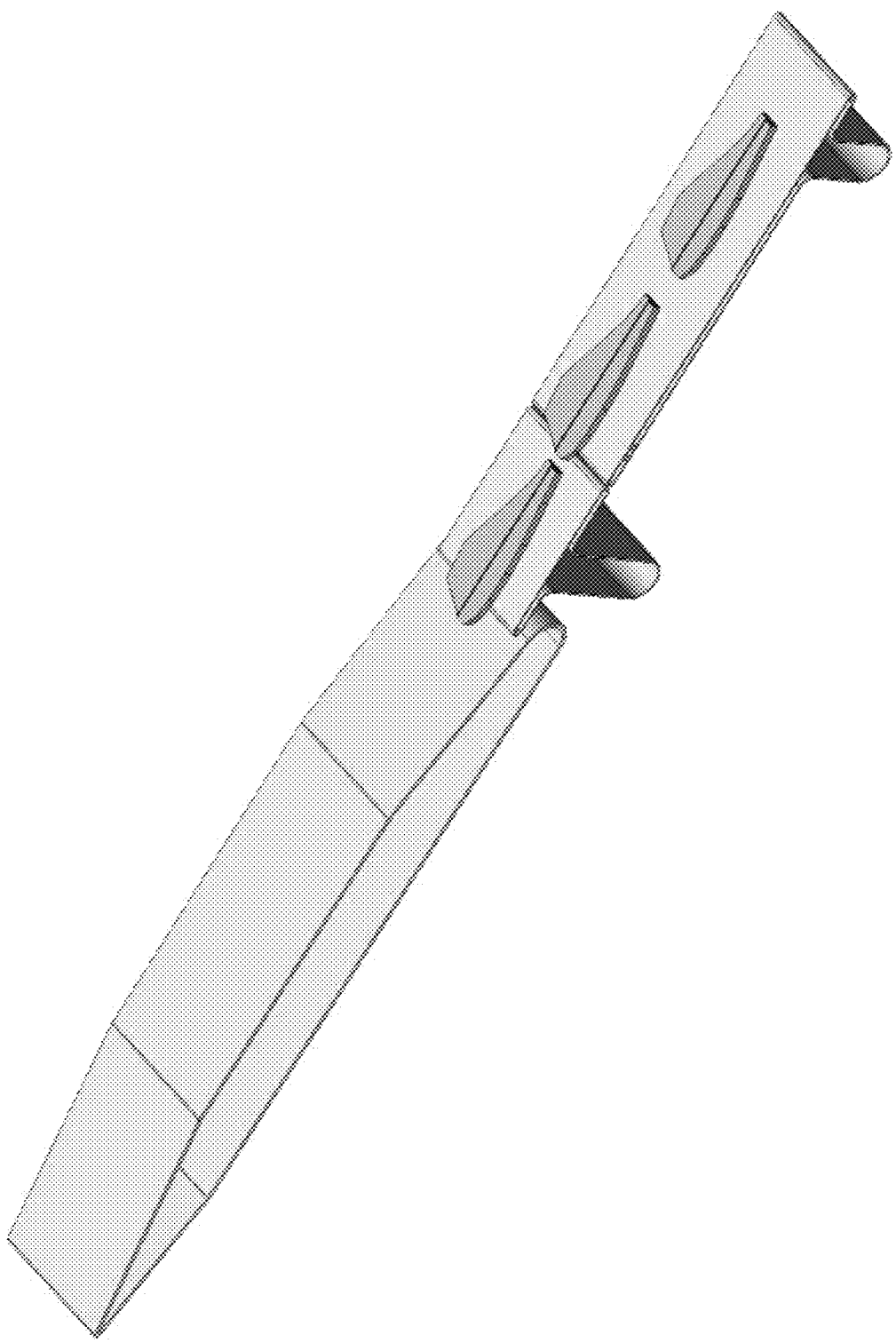

In the example shown in FIG. 11B, the desired spacing has been obtained between food article A and food article B. Once a sufficient part of food article B has been transferred over to the second conveyor, the outfeed end of the first conveyor (and the infeed end of the second conveyor at the same time) is moved back in the direction opposite to which the conveyor system is moving, such that it will be ready to move forward again for the next food article.

Figure 11C:
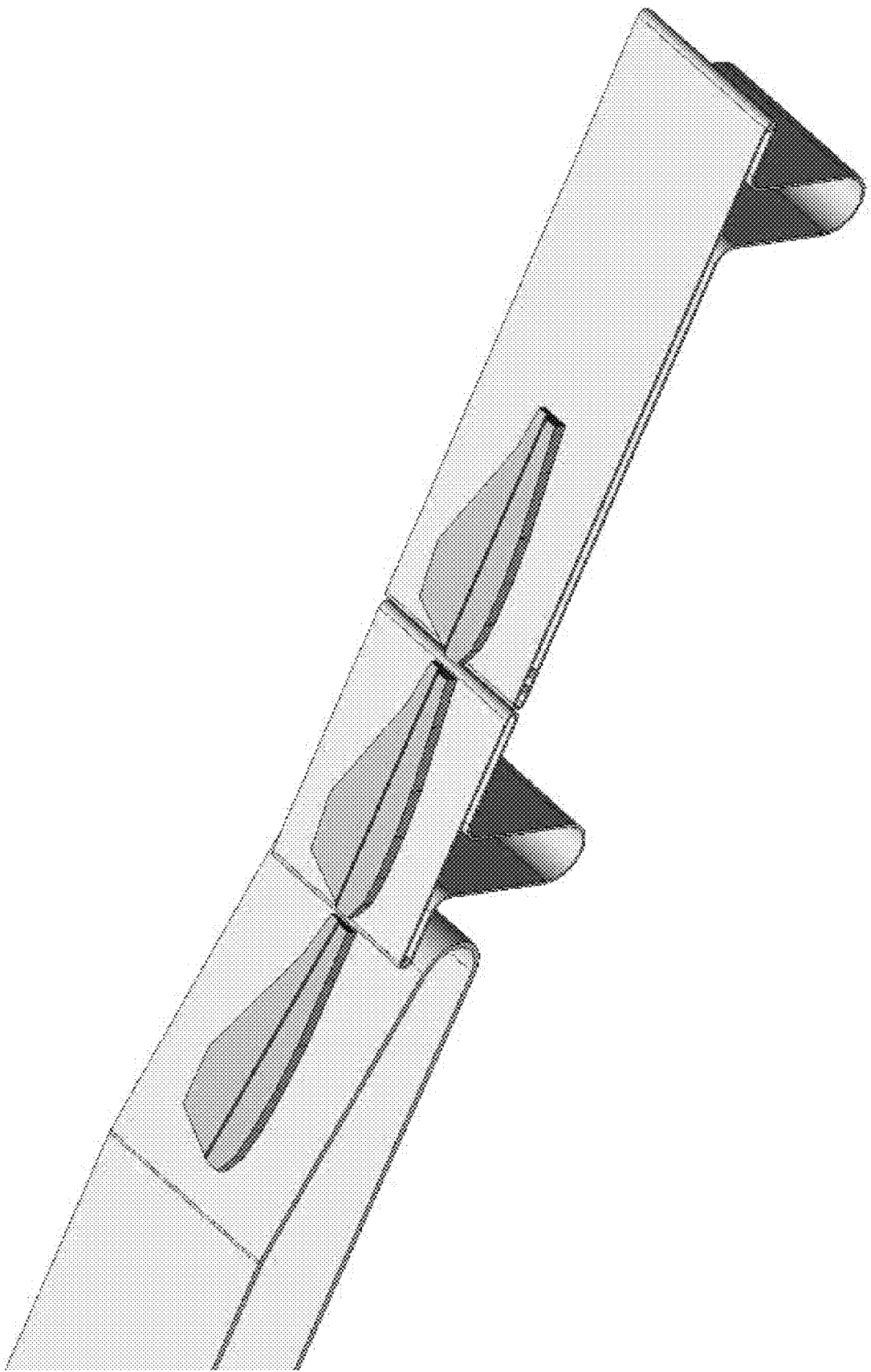

In the example shown in FIG. 11C, the desired spacing has been obtained between all three food articles.

DETAILED DESCRIPTION

Disclosed generally herein are food processing systems and apparatus comprising one or more of: at least one x-ray machine to determine the location of undesirable components (e.g., bones) within a food article (e.g., a fish fillet); at least one cutting machine to cut a food article into portions; at least one food grading apparatus for grading portions of a food article based on different characteristics; and at least one realigning apparatus, as well as methods utilizing the same. The grading apparatus may be able to grade portions of a food article oriented parallel to each other and in series with each other with respect to the direction of movement of a conveyor surface, as is described in further detail below, and may be able to grade portions of a cut food article from the middle of the article. The grading apparatus may be able to grade portions while maintaining an original alignment and orientation of the portions.

The illustrations presented herein are not meant to be actual views of any particular food processing apparatus, x-ray machine, cutting machine, food grading apparatus, realigning apparatus, or component thereof, but are merely simplified schematic representations employed to describe illustrative embodiments. The drawings are not necessarily to scale.

Relational Terms: As used herein, any relational term, such as "first," "second," "over," "beneath," "top," "bottom," "underlying," "up," "down," etc., is used for clarity and convenience in understanding the disclosure and accompanying drawings, and does not connote or depend on any specific preference, orientation, or order, except where the context clearly indicates otherwise. The terms "vertical" and "horizontal" merely refer to a drawing figure as oriented on the drawing sheet, and in no way are limiting of orientation of a food processing apparatus, food grading apparatus, or any portion thereof.

Alignment: As used herein, the term "alignment" refers to the position of a food article and the surface of a conveyor in the vertical dimension; for example, the completeness of the contact between a food article and a conveyor surface. In particular examples, a food article may be flat, bunched, or folded. In some embodiments, whether the alignment of a food article portion during grading is "substantially preserved" may be determined by whether the food article portion(s) remains flat on the surface of the conveyor throughout the process; e.g., the entire bottom surface of the portion retains contact throughout the process with the surface of the conveyor.

Cutting: As used herein, the term "cutting" includes, for example and without limitation: cutting and removing unwanted components (e.g., bones, cartilage, fat, defects in flesh, tough tissues, skin, blood, and organs) from a food article, such as a fish fillet, and/or cutting a food article into portions. The term "advanced cut" refers specifically to the process by which a food article is cut into portions by a cutting machine.

Figure 1:
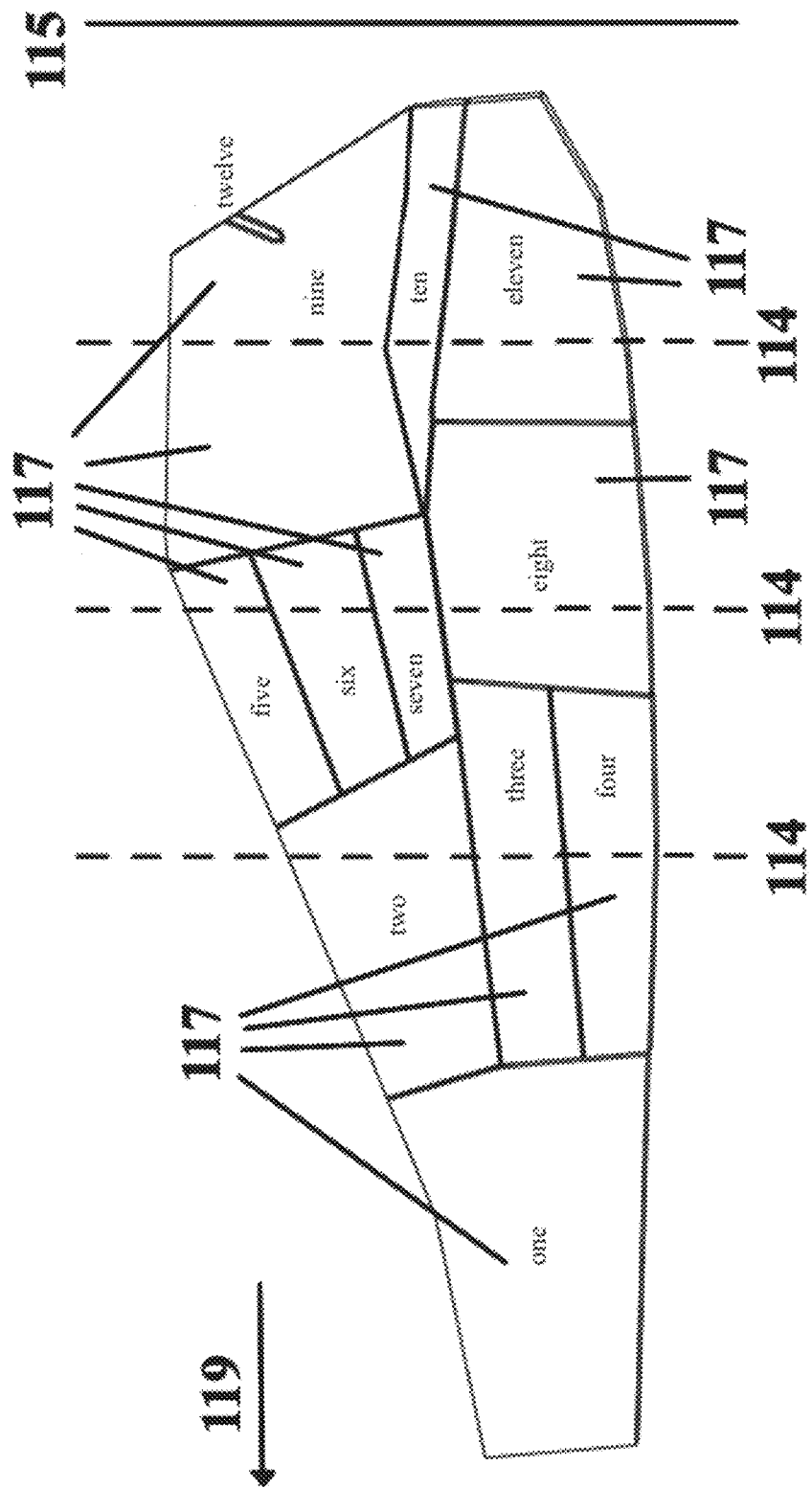
FIG. 1 includes a top view of an example of a food article 101 (i.e., a fish fillet) cut into portions 117, wherein included in the shape of the original food article 101 is a first plurality of portions 117 ("two," "three," and "four"), a second plurality of portions ("five," "six," "seven," and "eight"), and a third plurality of portions ("nine," "ten," and "eleven"), each of which is bisected by a line 114 parallel to out-feed end 115 of the conveyor upon which the article 101 is disposed.

Grading: As used herein, the term "grading" refers to a process by which portions of a food article (e.g., a fish fillet, cut so as to maintain the resulting portions together in the general shape of the original fillet; FIG. 1) are separated, for example, according to one or more selection criteria. In some embodiments, a food article is graded by a method comprising "movement" of at least one portion of the food article to an area that is separate from an area including at least one of the remaining portions of the food article. In some examples, a food article is graded by moving at least one portion of the food article to remove the portion(s) from a conveyor surface.

In series: As used herein, the term "in series" refers to portions arranged next to each other in a direction in which a conveyor is moving. In the illustrative cut food article 101 of FIG. 1, portions "one," "two," "five," and "nine" are in series; i.e., they are next to each other in the direction 119 the conveyor is moving.

Orientation: As used herein, the term "orientation" refers to the position of a food article and the surface of a conveyor in the two dimensions of the surface. In some embodiments, whether the orientation of food article portions during grading is "substantially preserved" may be determined by whether the position of one side (or edge) of the food article portion(s) is maintained throughout the process with respect to an edge of the conveyor. In some examples, "substantial preservation" of the orientation of food article portions may be determined by whether the general shape of the portion(s) is maintained throughout the process on the conveyor. For example, a bilaterally symmetrical portion may be flipped upside-down on the conveyor in these examples, wherein the orientation is substantially preserved, because the general shape of the portion is maintained.

Parallel: As used herein, the term "parallel" refers to portions arranged next to each other in a direction perpendicular to the direction in which a conveyor is moving. In the illustrative cut food article 101 of FIG. 1, portions "two," "three," and "four" are parallel; i.e., they are next to each other in the direction perpendicular to the direction 119 the conveyor is moving.

Properly (aligned and/or oriented): As used herein, the term "properly aligned" refers to a food article or portion(s) thereof that is flat against a conveyor (e.g., without any folds) upon which the article or portion(s) is being transported, and the terms "proper orientation," "oriented properly," and "properly oriented" mean that the food article or portion(s) thereof is positioned correctly with respect to the conveyor. In other words, the terms "proper orientation and alignment," "oriented and aligned properly," and "properly oriented and aligned" mean that the shape of a food article or portion(s) thereof is positioned in a certain manner with respect to the conveyor and the direction the conveyor is moving.

Robot: As used herein, the terms "robot" and "device" are used interchangeably.

Tray: As used herein, the term "tray" refers to any receptacle for a graded portion of a food article.

Figure 2:
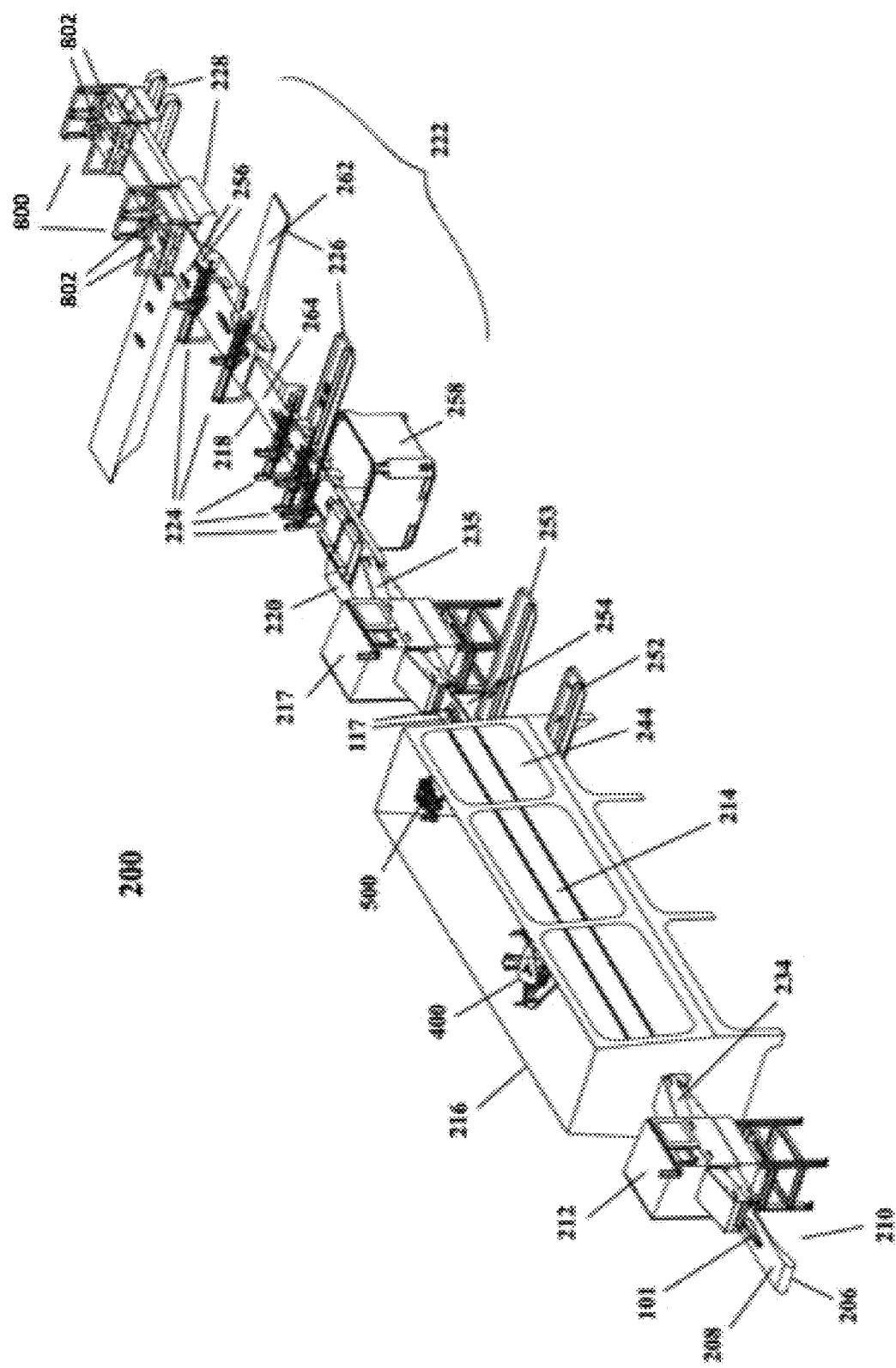
FIG. 2 includes a perspective view of an example of a food processing apparatus.

FIG. 2 is a top perspective view of a food processing apparatus 200 according to some embodiments. The food processing apparatus 200 may detect and cut undesired portions 117 from food articles, for example, being carried through the food processing apparatus 200 by the directional movement of a feed conveyor 208 surface. The food processing apparatus 200 may grade food articles according to certain characteristics (e.g., weight, quality, size, type, etc.). For example, the food processing apparatus 200 may be configured to automatically cut pin bones, other bones or bone fragments, cartilage, and/or other undesirable components from a food article 101. The food processing apparatus 200 may cut the food article 101 into desired portions, 117 and grade the portions 117 according to at least one characteristic. In the drawings, the food articles are illustrated by way of example as fish fillets; however, the food processing apparatus 200 in other examples is used to process and grade any of several different food articles (e.g., beef, pork, poultry, lamb, crustaceans, etc.).

The food processing apparatus 200 may be utilized in the meat industry to cut ribs away from a carcass, such that the ribs are not cut, but the food processing apparatus 200 can cut through other bones in the meat sections. The food processing apparatus 200 may be utilized in the poultry industry for fully automatic detection and cutting of cartilage, for example, in the front tip of chicken breasts, which commonly remain attached to the breasts after filleting.

An exemplary food processing apparatus 200 according to some embodiments may include one or more of each of: a feed conveyor 208; an aligning section 210; an first x-ray machine 212, 217; a cutting conveyor 214; a cutting machine 216; a first imaging system 234; a removal or check section 244, 254; at least a second imaging system 235; and at least one computer.

As shown in FIG. 2, an exemplary food processing apparatus 200 according to some embodiments may include a feed conveyor 208; an aligning section 210; a first x-ray machine 212; a cutting conveyor 214, a cutting machine 216; a first imaging system 234; an automatic removal section 244; a (e.g., manual) check section 254; at least a second x-ray machine 217; at least a second imaging system 235; a rejection section 220; a grading conveyor 218; at least one grading robot 224; at least one processing conveyor 226; at least one realigning section 800; at least one realigning apparatus 802; and at least one computer. With regard to each of the foregoing components of a food processing apparatus 200 according to certain embodiments, the computers described independently for each may in some examples be either a single central computer or in other examples a plurality of computers.

As shown in FIG. 2, a pre-trimming line 206 may precede the food processing apparatus 200. On the pre-trimming line 206, fish fillets 101 may be manually or automatically trimmed prior to entering the food processing apparatus 200. For example, on the pre-trimming line 206, undesirable components, for example, loose bones, cartilage, parasites, blood spots, or obvious defects in flesh, may be removed from fish fillets 101. In some embodiments, fish fillets 101 within the pre-trimming line 206 may include skin. In some embodiments, the fish fillets 101 may not include skin.

The feed conveyor 208 may follow the pre-trimming line 206, and may transport fish fillets 101 leaving the pre-trimming line 206 to the aligning section 210. In the aligning section 210, fish fillets 101 may be properly aligned and placed in a proper orientation prior to continuing through the food processing apparatus 200. For example, a fish fillet 101 may be properly oriented when a longitudinal length of the fish fillet 101 is substantially parallel to a length of a conveyor. As another non-limiting example, a fish fillet 101 may be properly oriented on a conveyor when a tail portion of the fish fillet 101 is positioned to come first as the fish fillet 101 is transported on the conveyor.

In some embodiments, alignment and orientation of fish fillets 101 may be performed manually. In some embodiments, the fish fillets 101 may be aligned and oriented automatically by an imaging device and automated robotic arm combination (e.g., a robotic arm may be utilized to rotate or push forward a food article, such as a fish fillet). Accordingly, each fish fillet 101 may be properly aligned and oriented prior to being fed into the first x-ray machine 212. For example, FIG. 11(A-C) shows a system that may be used to align food articles in some embodiments.

Fish fillets 101 may be fed one by one into the first x-ray machine 212, which may capture a first x-ray image of each fish fillet 101. The first x-ray machine 212 may also capture the precise location of bones within each fish fillet 101. Additionally, the first x-ray machine 212 may capture the precise location of each fish fillet 101 with respect to the feed conveyor 208. For example, the food processing apparatus 200 may include the x-ray machine described in U.S. Patent Application Publication No. 2012/0307013 A1, the disclosure of which is incorporated in its entirety herein by this reference. The first x-ray machine 212 may transfer information regarding the location of the bones within each fish fillet 101, and the location of each fish fillet 101 with respect to the feed conveyor 208 to a computer. The feed conveyor 208 may convey the fish fillets 101 through the first x-ray machine 212, and then off of the feed conveyor 208 and onto the cutting conveyor 214. In some embodiments, the feed conveyor 208 and/or the cutting conveyor 214 may comprise one or more of a belt, cords, a plurality of members linked together, etc. The cutting conveyor 214 may feed the fish fillets 101 to be cut in the cutting machine 216.

The computer may be programmed to track the movement of each fish fillet 101 as the fish fillet 101 moves through the food processing apparatus 200. The computer may use images taken from the first x-ray machine 212, in addition to information related to the movement of the feed conveyor 208 and cutting conveyor 214, to determine an estimated location of each fish fillet 101 within the food processing apparatus 200. However, some uncertainty may arise as to the precise location of each fish fillet 101 within the food processing apparatus 200, for example, when the fish fillet 101 moves from the feed conveyor 208 to the cutting conveyor 214. In some examples, the uncertainty is acceptable to the process. In other examples, this uncertainty is unacceptable to the process and more accuracy is needed. Therefore, particular examples may include an imaging system 234 on the cutting conveyor 214. The imaging system 234 may capture a three-dimensional ("3D") image of each fish fillet 101. In some examples, the imaging system 234 captures a 3D image of the fish fillet 101 as the fish fillet 101 is disposed on the cutting conveyor 214, before the fish fillet 101 is subject to any further manipulations that may alter its alignment and/or orientation.

Figure 3:
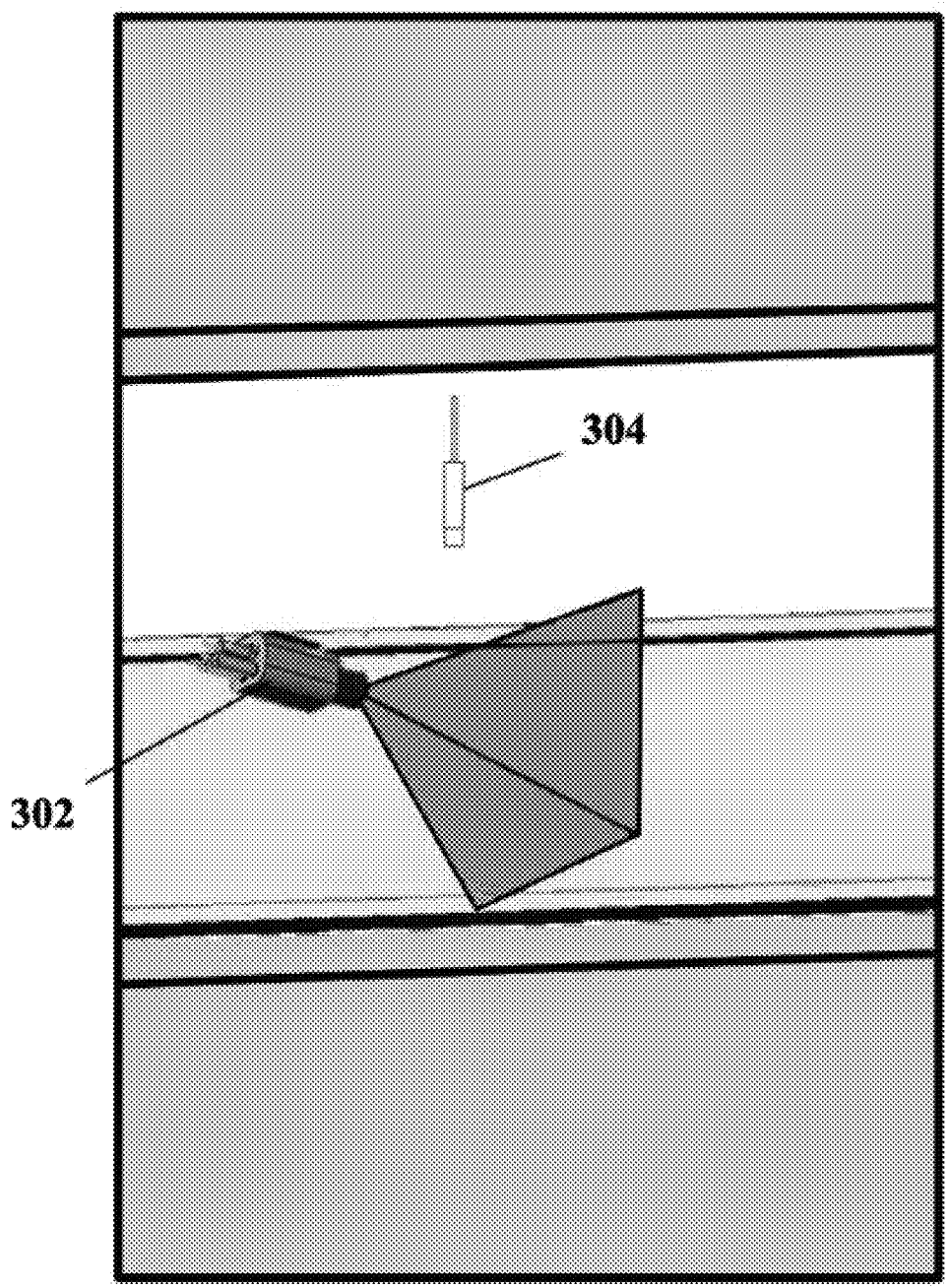
FIG. 3 includes a perspective view of an example of a 3D camera of an imaging system of a food processing apparatus.

As shown in FIG. 3, the imaging system 234, which may point towards the cutting conveyor 214, in some embodiments may include a 3D camera 302. The imaging system 234 may include a laser 304 that puts a light on the fish fillet 101. In some embodiments, the imaging system 234 may capture a silhouette image or a full color 3D image. In some embodiments, the x-ray image of each fish fillet 101 may be used to generate a 3D image of the fish fillet 101. In some examples, the intensity of each pixel in the first x-ray image may be based on the thickness of the fish fillet 101. For example, the thinner the fish fillet 101 is, the higher the intensity of a correlating pixel may be, and conversely, the thicker the fish fillet 101 is, the lower the intensity of a correlating pixel may be. With the 3D camera 302, it may be possible to capture a height profile of the fish fillet 101 along the image.

The 3D image of each fish fillet 101 captured by the imaging system 234 may provide an accurate measurement of a volume of each fish fillet 101. Furthermore, a color 3D image may provide information as to a location of fat within the fish fillet 101. The 3D image may also provide more accurate information as to the weight distribution of each fish fillet 101. For example, the imaging system 234 may transfer the 3D image to the computer. The computer may be programmed to determine an alignment and orientation of each fish fillet 101. From any and all of the foregoing information, the computer may adjust cutting procedures (described in further detail below), for example, to account for the particular alignment and orientation of the fish fillet 101.

The computer may match the first x-ray image of each fish fillet 101 captured by the first x-ray machine 212 with the 3D image of each fish fillet 101 captured by the imaging system 234 (e.g., by mapping the image from tail to head) to determine the precise location of the bones within each fish fillet 101 with respect to the cutting conveyor 214. In some embodiments, this may be accomplished by matching a center of gravity of the first x-ray image and the 3D image of each fish fillet 101, as well as the principle axis of the first x-ray image and the 3D image of each fish fillet 101, as described in a mapping procedure of U.S. Patent Application Publication No. 2012/0307013 A1. In some embodiments, multiple x-ray images may be taken of each fish fillet 101 at differing angles, and the multiple resulting x-ray images are matched using a coordinate system, as described in U.S. Patent Application Publication No. 2012/0307013 A1. Any combination of the above described methods for determining the precise location of bones within a fish fillet 101 may be used. Furthermore, any of the mapping procedures described in U.S. Patent Application Publication No. 2012/0307013 A1 may be used.

The computer may determine an individualized cutting pattern for each fish fillet 101 using information related to the precise location of bones within each fish fillet 101. For example, the cutting pattern of each fish fillet 101 may be determined to cut out portions 117 of the fish fillets 101 containing bones, while minimizing an amount of flesh removed with the bones. Furthermore, the cutting pattern may also be determined based on the weight distribution of the fish fillet 101 determined by the first x-ray image and 3D image. Thus, the cutting pattern can be determined to cut the fish fillets 101 into portions 117 of fixed weight, length, and/or in a pattern which optimizes a portion 117 yield. The cutting pattern for each fish fillet 101 may be superimposed onto the first x-ray image of the fish fillet 101, 3D image of the fish fillet 101, or both. The fish fillet 101 may then be cut into portions 117 according any of the methods and using any of the cutting machinery described in U.S. Patent Application Publication No. 2012/0307013 A1. The cutting machine 216 may include at least one cutting robot 400, which is described in further detail below with reference to FIG. 4(A-B). In some examples, a single cut portion 117 of a fish fillet 101 may contain all the parts of the fish fillet 101 having bones, and another cut portion 117 may include all the parts not having bones. A fish fillet 101 may be cut into a shape that maintains the outline of the original fish fillet 101, wherein the shape comprises both portions 117 that are in series with one another, and into portions 117 that are parallel to each other.

FIG. 4(A-B) depicts two illustrative cutting robots 400. However, any cutting robot (for example, any of the cutting robots described in U.S. Patent Application Publication No. 2012/0307013 A1) may be used in certain embodiments. The cutting robot 400 may be powered by any means known in the art, for example and without limitation, air cylinders, motors, and hydraulic powering means. The cutting robot 400 may also use any type of cutting known in the art, for example and without limitation, waterjet cutting, cutting with rotating knives, and ultrasonic cutting. If water jet cutting is used any type of cutting head can be used to focus the high pressure water into a thin beam that can cut through the food objects. The cutting robot 400 may also have any number of degrees of freedom. For example, a cutting robot 400 with a single degree of freedom may move in a direction perpendicular to the cutting conveyor 214, or at an angle to the cutting conveyor 214, such that it is capable of make straight cuts across the surface of the cutting conveyor 214.

Figure 4A:
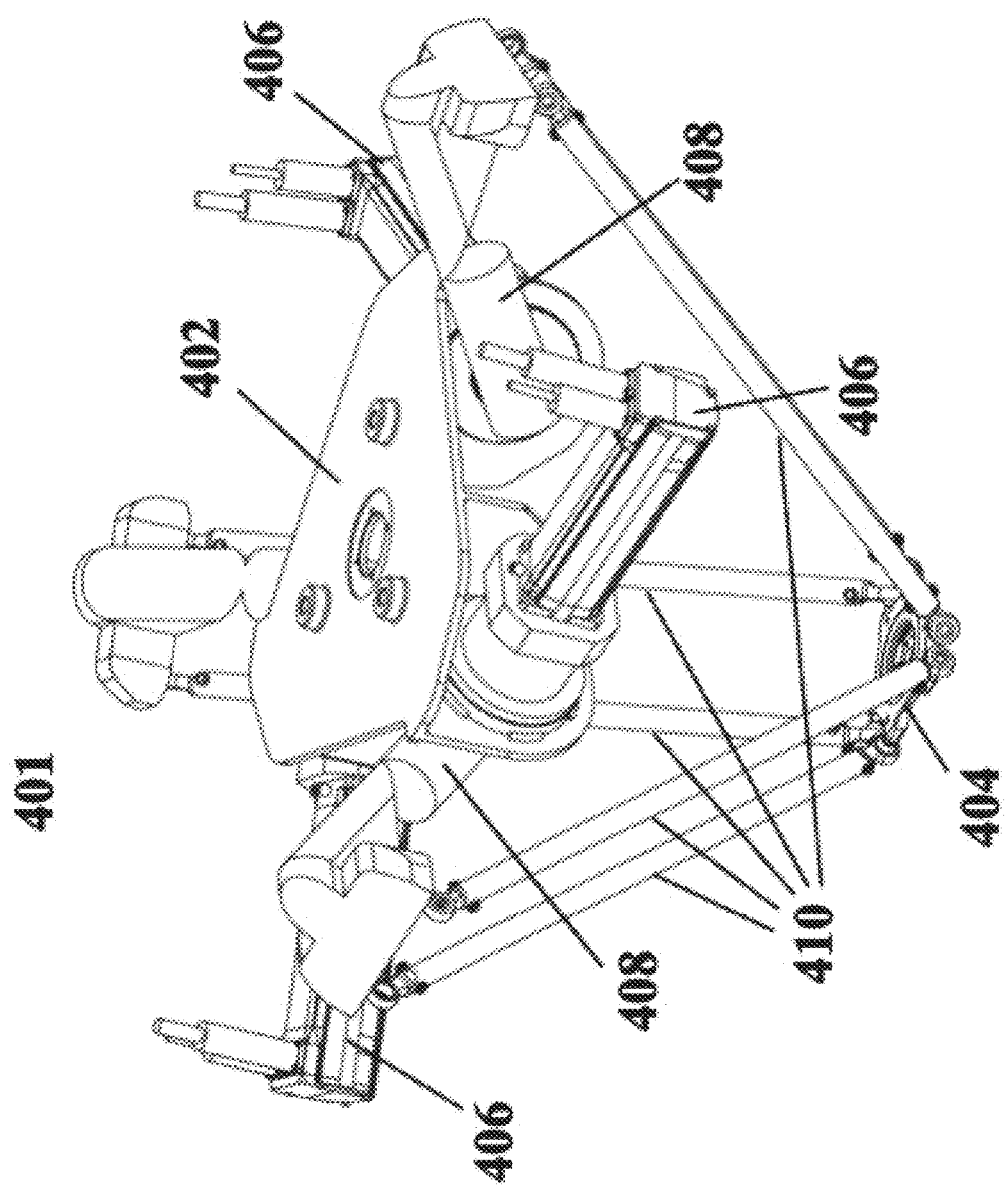
FIG. 4A includes a perspective view of an example of a "delta" or "spider" cutting robot (i.e., a three degrees of freedom cutting robot).

FIG. 4A illustrates a "delta" or "spider" cutting robot 401 with three degrees of freedom. If the x-axis is in the direction of movement of the cutting conveyor 214, the y-axis is horizontal to the direction of movement of the cutting conveyor 214, and the z-axis is the height from the cutting conveyor 214, the "delta" or "spider" cutting robot 401 may be mounted with a base plate 402 in a plane parallel to the surface of the cutting conveyor 214, and at a distance above the surface of the cutting conveyor 214. The "delta" or "spider" cutting robot 401 may further include a parallel plate 404 that is parallel to the base plate 402, where a cutting head (not shown) may be mounted. The "delta" or "spider" cutting robot 401 may further include three motors 406, which may rotate a solid shaft 408 that is connected with bars 410 to the parallel plate 404. The "delta" or "spider" cutting robot 401 may then move freely in the x-, y-, and z-direction within a moving envelope. In certain examples, the moving envelop may be about 200 mm in the z-direction, and about 600-800 mm in the x- and y-direction.

Figure 4B:
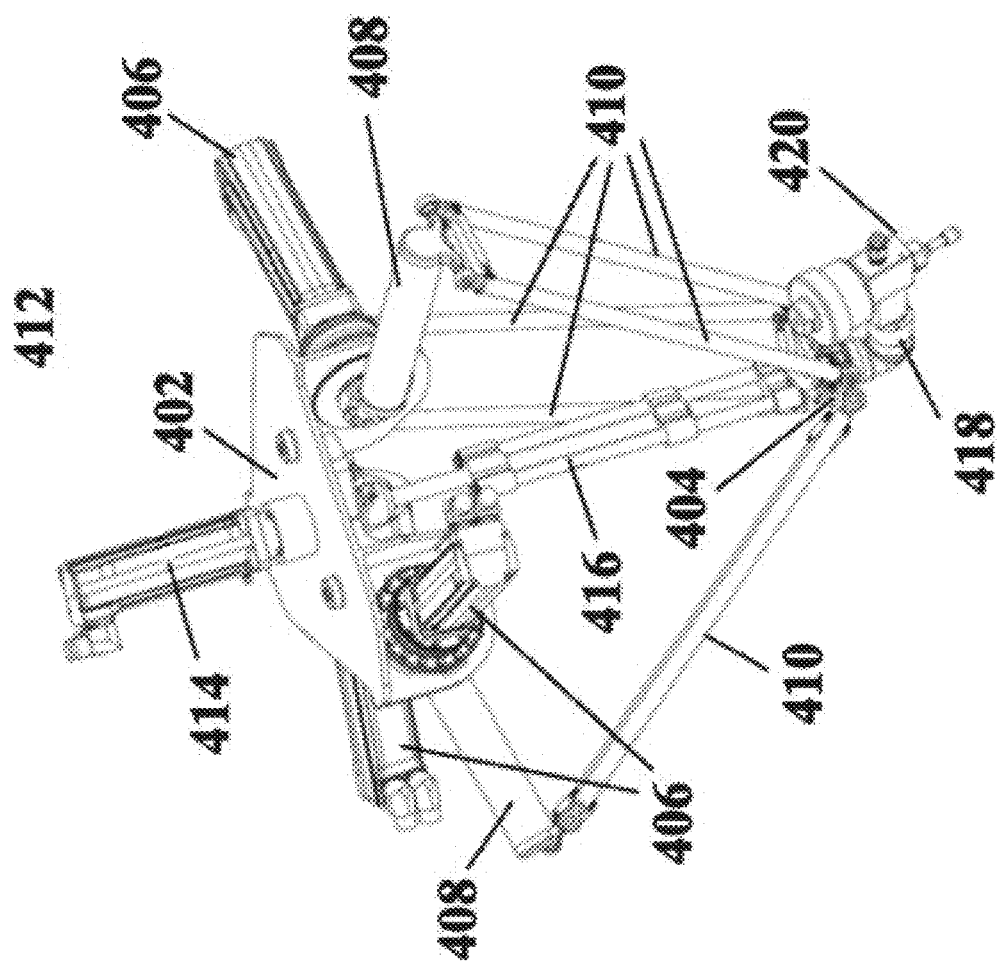
FIG. 4B includes a perspective view of an example of a four degrees of freedom cutting robot.

As illustrated in FIG. 4B, the cutting robot 400 may be a four degrees of freedom cutting robot 412, where the additional degree of freedom allows the four degrees of freedom cutting robot 412 to cut a fish fillet 101 at a certain angle. In such an embodiment, the four degrees of freedom cutting robot 412 may include a motor 414 at the top of the base plate 402 that can rotate the shaft 416. The shaft 416 may be connected to a perpendicular gear 418 that is connected to a parallel plate 404. A cutting head 420 may be connected to the perpendicular gear 418, such that a rotation of the cutting head 420 can be performed. In some examples, the cutting head 420 can rotate around any axis in its moving envelope that is parallel to the x-axis.

In some embodiments, the cutting robot 400 may be a six degree of freedom cutting robot (not shown). A six degree of freedom cutting robot may be able to move freely in the x-, y-, and z-direction, and also be able to rotate around the x-, y-, and z-axis to perform arbitrary cuts.

In some embodiments, during cutting procedures, an alignment and orientation of each fish fillet 101 with respect to the cutting conveyor 214 may be at least substantially preserved. In some embodiments, the alignment and/or orientation of the fish fillet 101 may be disturbed. In particular embodiments, the cutting machine 216 may include a scraper located proximate a top surface of the cutting conveyor 214. The scraper may be so located as to contact the now cut portions 117 of the fish fillet 101 and to generally realign portions 117 that have moved out of the original alignment and orientation.

Referring to again to FIG. 2, the cutting machine 216 may include an automatic removal section 244. Alternatively, the automatic removal section 244 may be located outside the cutting machine 216, but preferably closely proximate the cutting machine 216 with the cutting robot 400. The automatic removal section 244 may include at least one robotic arm 500 (as described in more detail below in FIG. 6(A-E)) following the at least one cutting robot 400 of the cutting machine 216, for removing cut portions 117 of a fish fillet 101 having bones. A robotic arm 500 of a food processing apparatus 200 may also be, for example, a grading robot 224, as described in further detail below (e.g., needle grading robot 600, two-degree of freedom grading robot 700, three degrees of freedom grading robot, four degrees of freedom grading robot (FIGS. 9(I-K)), gripper grading robot 601, or spray-removal robot 651 (FIG. 7A).

In some embodiments, the cutting machine 216 communicates with the robotic arm 500, for example, via a computer receiving an input signal from the cutting machine 216, and delivering an output signal to the robotic arm 500. For example, the cutting machine 216 may communicate to the robotic arm 500 the location, alignment, and/or orientation of portions 117 cut according to the cutting pattern employed by the cutting machine 216, and may also communicate the identification of portions 117 containing bones or other undesirable attributes, so that such portions can be removed by the robotic arm 500.

The removal process may be performed while the cut fish fillets 101 are still on the cutting conveyor 214, as the most accurate information about the precise location of the portions 117 and bones is available. The computer may control the at least one robotic arm 500 and direct the at least one robotic arm 500 to grip portions 117 of a fish fillet 101 having bones, and to remove the portions 117 from the cutting conveyor 214. For example, portions 117 of the fish fillets 101 known to have bones (e.g., a pin bone section)

may be automatically removed by the at least one robotic arm 500. Furthermore, portions 117 of the fish fillets 101 that are indicated as having bones in the first x-ray image or 3D image may be removed.

Figure 5:
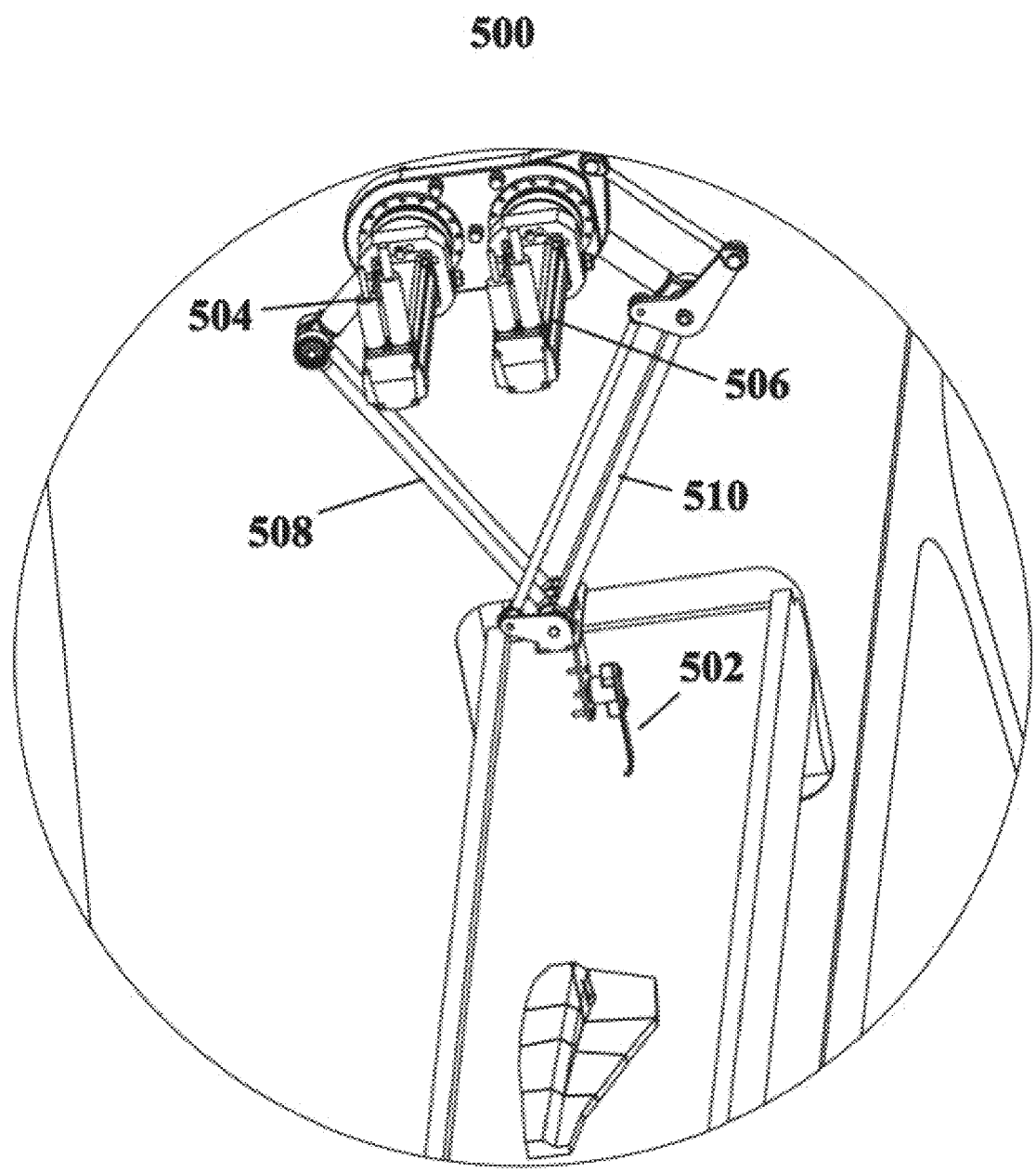
FIG. 5 includes a perspective view of an example of a robotic arm of a food processing apparatus.

FIG. 5 is a perspective view of a robotic arm 500 of the food processing apparatus 200 of FIG. 2. In some embodiments, at least one robotic arm 500 may grip a portion 117 of a cut fish fillet 101, and slide the portion 117 off of a side of the cutting conveyor 214 into a first conveyor or tray 252.

As shown in FIG. 5, a robotic arm 500, located in the automatic removal section 244 and proximate the exit of the cutting machine 216, may include a gripper 502, a first motor 504, a second motor 506, a first control arm 508, and a second control arm 510. The first control arm 508 may be coupled to the first motor 504 at a first end of the first control arm 508, and may be coupled to the gripper 502 at a second end of the first control arm 508. The second control arm 510 may be coupled to the second motor 506 at a first end of the second control arm 510, and may be coupled to the gripper 502 at a second end of the second control arm 510. The first motor 504 and second motor 506 may be controlled by a computer. The first motor 504 may rotate the first control arm 508 about the first end of the first control arm 508. The second motor 506 may rotate the second control arm 510 about the first end of the second control arm 510. When the first ends of the first and second control arms 508, 510 are rotated, the second ends of the first and second control arms 508, 510 may manipulate the gripper 502. For example, the computer may control the first and second motors 504, 506 to move the first and second control arms 508, 510, respectively, and, in turn, manipulate the gripper 502 to grip portions 117 of a cut fish fillet 101 containing bones. The computer may further manipulate the gripper 502 to dispose the portions 117 of the fish fillet 101 containing bones in a first conveyor or tray 252. In some embodiments, the gripper 502 is rotated with an actuator; for example and without limitation, an air cylinder, motor, linear motor, traditional motor, or solenoid (not shown in images).

In particular embodiments, the gripper 502 may include a hook that can be slipped under a portion 117 to be removed, or stuck into the portion 117 to be removed. In particular embodiments, the gripper 502 may include at least two members that can clamp or press the portion 117 between the two members. In particular embodiments, the gripper 502 may include a suction member that uses a vacuum to suck the portion 117 against the gripper 502. In particular embodiments, the at least one robotic arm 500 may include the robotic gripper unit described in U.S. Patent Application Publication No. 2012/0307013 A1, and/or may include the associated gripper described in U.S. Patent Application Publication No. 2012/0307013 A1. In particular embodiments, the at least one robotic arm 500 may be replaced with at least one grading robot 224, which is described above and in further detail below in relation to FIG. 6(A-E) and FIG. 9(A-K).

In some embodiments, the first conveyor or tray 252 may comprise a box, bin, tub, and/or basket. In some embodiments, the at least one robotic arm 246 may grip a portion 117 and lift the portion 117 off of the cutting conveyor 214 and subsequently place the portion 117 in the first conveyor or tray 252. In some examples, the alignment and orientation of the portions 117 of the fish fillet 101 not containing bones are not substantially disturbed during the removal process. In other words, an alignment and orientation of the portions 117 not containing bones may be preserved, while portions 117 containing bones are removed. The removal process may be fully automatic, and may be controlled by the computer, for example, based on at least one of the first x-ray image, 3D image, and cutting pattern of each fish fillet 101. In some embodiments, the cutting machine 216 may include a robotic arm 500 similar to the any of the robotic arms described in U.S. Patent Application Publication No. 2012/0307013 A1.

The food processing apparatus 200 may optionally include a check section 254 following the cutting machine 216 and automatic or manual removal section 244. In some embodiments, the cutting machine 216 may not include the at least one robotic arm 246, and the check section 254 may serve to remove portions 117 of a fish fillet 101 containing an undesirable component, for example, bones. In some embodiments including the at least one robotic arm 246, the check section 254 may be utilized to ensure that after the fish fillet 101 has been cut, and portions 117 removed by the at least one robotic arm 246, that all portions 117 containing bones have been removed. Portions 117 containing bones that are removed in the check section 254 and placed in a second conveyor or tray 253. In some examples, the check section 254 is a manual check section 254. In some embodiments, the food processing apparatus 200 may not include a check section 254, and may include just the at least one robotic arm 246 for removing portions 117 of fish fillets 101 having bones. All portions 117 of a fish fillet 101 placed in the first and second conveyors or trays 252, 253 may then be taken to be used in other products and applications. The alignment and orientation of the remaining portions 117 may be preserved.

As shown in FIG. 2, a fish fillet 101 may be moved into a second x-ray machine 217. The second x-ray machine 217 may function the same as the first x-ray machine 212, with similar components, and may take a second x-ray image of the fish fillet 101. The second x-ray machine 217 may x-ray and capture second x-ray images of the remaining portions 117, which may be oriented parallel to each other, in series with each other, or both. The second x-ray machine 217 may transfer the second x-ray images to the computer. The computer may be programmed to determine, based on the second x-ray images from the second x-ray machine 217, whether any bones remain in any of the remaining portions 117 of the fish fillet 101. Furthermore, the computer may be programmed to determine from the second x-ray images whether the fish fillet 101 has been advanced cut by the cutting machine 216.

In some embodiments, the second x-ray images may be utilized by the computer, for example and without limitation, to control a pull-back conveyor (not pictured) that directs portions 117 that still contain bones onto another conveyor (not pictured) while the remaining portions 117 that are bone-free may move onto the grading conveyor 218. In some examples, the bones from the portions 117 that still contain bones may be manually removed, and the manually-processed portions 117 may be moved again through the second x-ray machine 217. By way of further example, the second images may be utilized to provide feedback to the computer controlling the cutting robot 400 about the performance of the cutting. In certain examples wherein the cutting machine 216 has a tendency to leave bones in portions that are supposed to be bone-free, this feedback is important for correcting this tendency, but the feedback may also assist in optimizing yield.

Optimization of the yield following the cutting process occurs when there is some error rate in which operation of the cutting robot 400 fails to completely cut away all of a bone or bone fragment into a portion for removal. For example, when a computer is controlling the cutting robot 400 to make the closest cut possible to the bone or bone fragment, the rate of errors is likely to increase. Conversely, when a computer is controlling the cutting robot 400 to minimize the occurrence of such errors, the amount of flesh left in portions 117 containing bones is likely to increase. Therefore, in some embodiments, the second x-ray images may be utilized to provide feedback to the computer controlling the cutting robot 400 about the error rate, and the computer controlling the cutting robot 400 may adjust the operation of the cutting robot 400 to approach an optimal error rate (e.g., a non-zero rate of bones and bone fragments remaining in cut portions 117).

Further optimization of the yield can be obtained by inspecting the portions 117 containing bones that are identified by the second x-ray machine 217, as the characteristics of the extra tissue on those portions can then be evaluated.

In some embodiments, the remaining portions 117 of the fish fillet 101 may move from the cutting conveyor 214 to the grading conveyor 218, while at least substantially maintaining the alignment and orientation of the remaining portions 117. The grading conveyor 218 may be larger in width than the cutting conveyor 214, to allow for more portion positions 256 during the grading process, as described in further detail below. Furthermore, the grading conveyor 218 may include one or more sub-conveyors in series. In some embodiments, one or more sub-conveyors forming the grading conveyor 218 may vary in size and rate of movement. The grading conveyor 218 may feed the remaining portions 117 of the fish fillet 101 through a rejection section 220. The rejection section 220 may remove an entire fish fillet 101 from the grading conveyor 218 that, for some reason, may not have been cut into portions 117 in the cutting machine 216. For example, the rejection section 220 may include a scraper to slide an uncut fish fillet 101 off of the grading conveyor 218 and into a tray or onto a separate conveyor for further processing. The rejection section 220 may send data to a computer about an uncut fish fillet 101, and the computer may be programmed to adjust or improve cutting procedures based on the data.

As shown in FIG. 2, a fish fillet 101 may be moved into to a second imaging system 235, which may function the same as the first imaging system 234, with similar components. For example, a laser 304 may illuminate the portions 117, and a 3D camera 302 may transfer a 3D image to a computer programmed to determine features comprising, for example and without limitation, the location of fat, color, gaping, and other visual defects. In some examples, the second imaging system 235 captures a 3D image of a portions 117 as the portion 117 is disposed on a receiving conveyor, before the fish fillet 101 is subject to any further manipulations that may alter its alignment and/or orientation (e.g., a grading conveyor 218). Using certain wavelengths, the laser 304 may provide a 3D image utilized by the computer to detect parasites. From any and all of the foregoing information, the computer may adjust grading procedures (described in further detail below), for example, to grade the portions 117 according to these features.

In some embodiments, the remaining portions 117 of the fish fillet 101 may move from the second imaging system 235 into one or more further cutting machines 216, either directly, or after or betwixt grading procedures. In particular embodiments, the computer uses the information gathered from processing the 3D image to adjust or control cutting procedures in a further cutting machine 216.

In embodiments, the grading conveyor 218 may feed the portions 117 of a cut fish fillet 101 through a grading section 222 of the food processing apparatus 200. The grading section 222 may include at least one grading robot 224, at least one tub 258 beneath the grading conveyor 218, and a plurality of processing conveyors 226. As the remaining portions 117 pass under the grading robot(s) 224, the computer may direct the grading robot(s) 224 to move portions 117 of a fish fillet 101. The grading robot 224 may be selected from the group consisting of a needle grading robot 600, as described further below with respect to FIG. 6(A-E); a two-degree of freedom grading robot 700, as described further below with respect to FIG. 9(A-K); a three degrees of freedom grading robot; a four degrees of freedom grading robot; a gripper grading robot 601; and a spray-removal robot 651 (FIG. 7A) as described further below.

Figure 7A:
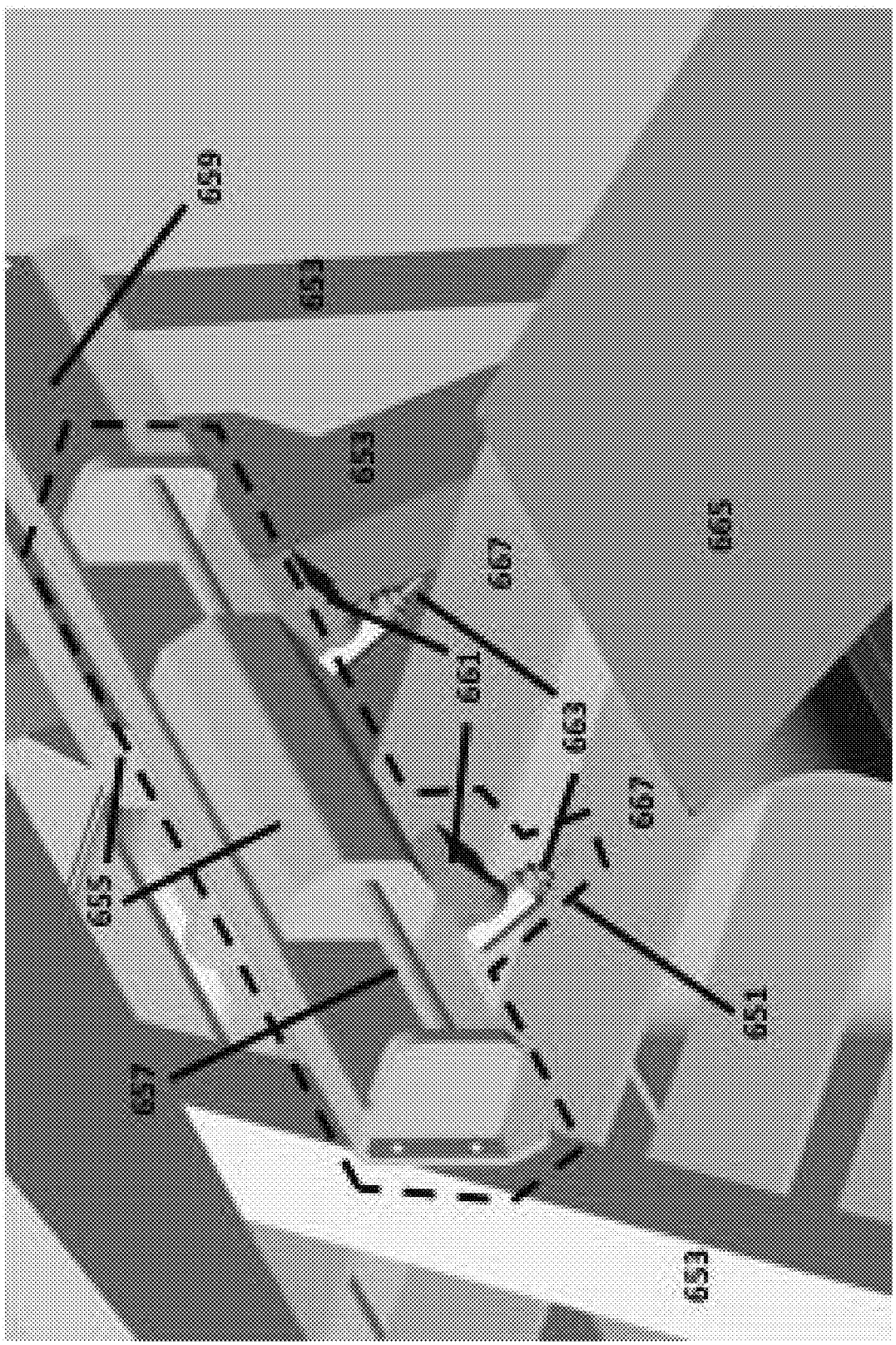
FIG. 7A includes a perspective view of a spray-removal grading section of a food processing apparatus 200. In some embodiments, a spray-removal robot 651 in the spray-removal section uses a stream of fluid (e.g., water) to remove a cut food portion 117 from a conveyor system including a first conveyor 665, for example, at an angle, as shown in FIG. 7B.
Figure 7B:
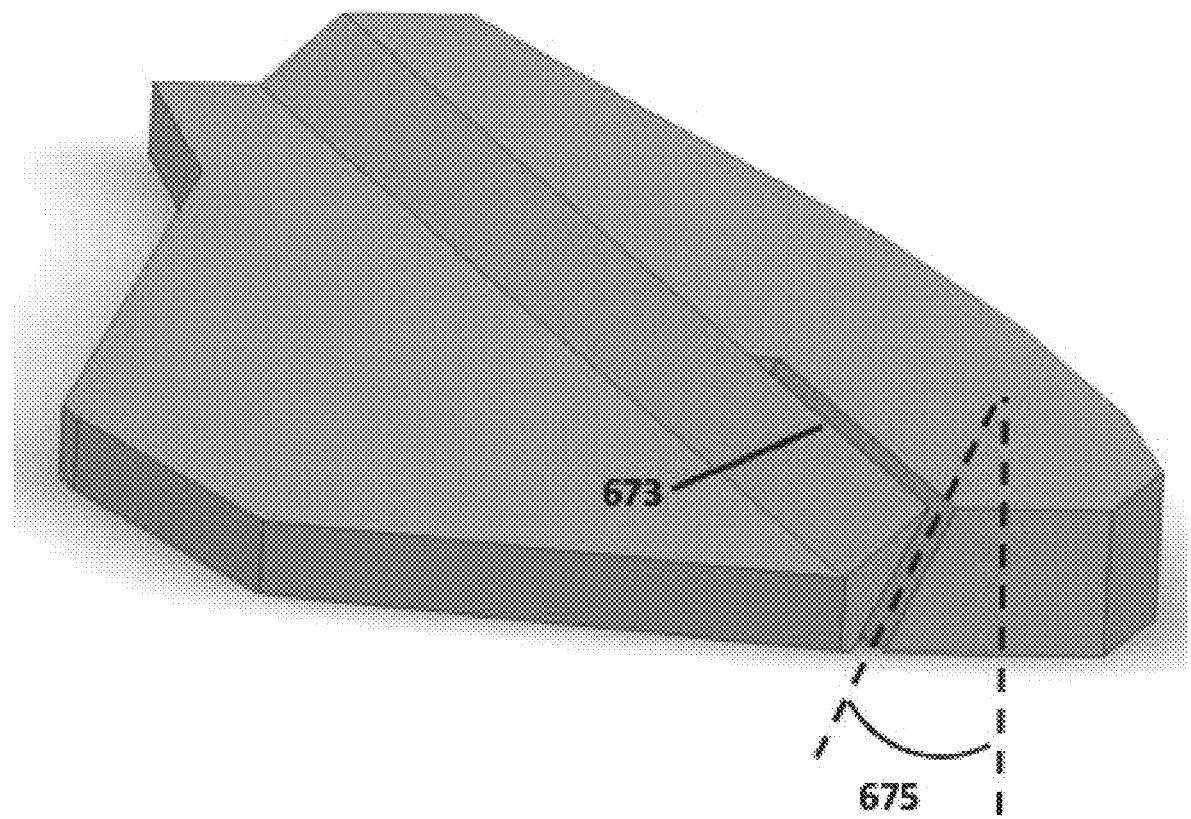
FIG. 7(A-E) illustrates means for the removal of a portion 117 that has already been cut from a fillet 101 by the operation of a spray-removal robot 651 in a spray-removal grading section of a food processing apparatus 200.
Referring to FIG. 7C, in some modes of operation, the ejection of fluid from the nozzle 663 can be controlled, such that a portion 117 defined by a partial cut 673 (i.e., starting and/or ending within the fillet 101) is made, for example, to leave the fillet 101 intact around the volume of the cut.
FIG. 7D includes a perspective view of a spray-removal section of a food processing apparatus 200 that comprises a plurality of spray-removal robots 651 that forces at least one food portion 117 on the same area 669 of a first conveyor 665, into the space between the first conveyor 665 and a receiving conveyor 667.
FIG. 7E includes a perspective view of a spray-removal robot 651 that comprises a spray array 664 containing a plurality of spray valve/nozzle elements (e.g., a left spray nozzle 666, a right spray nozzle 672, a center spray nozzle 674, and/or a second center spray nozzle 676).
Figure 7C:
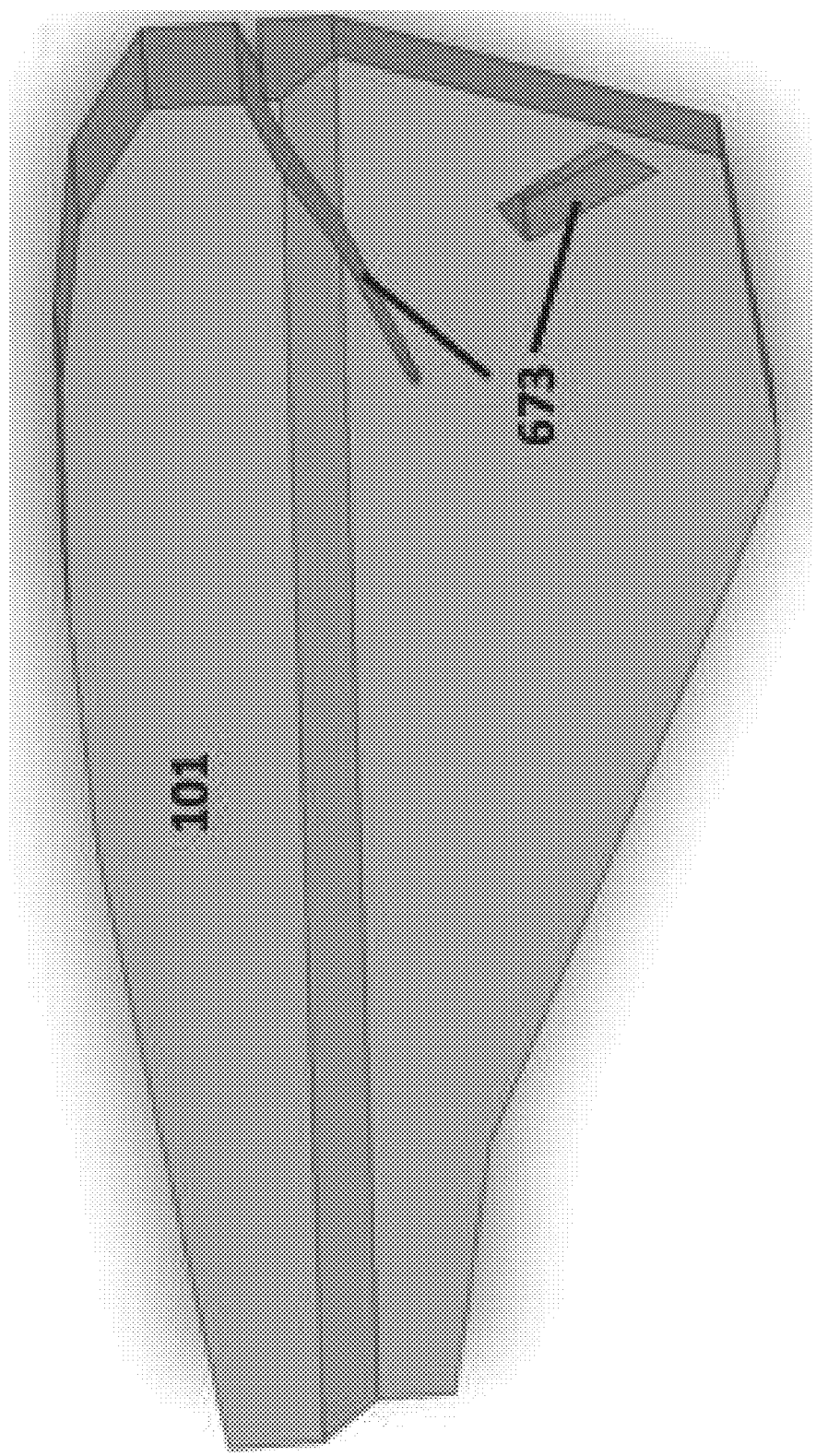
Figure 7D:
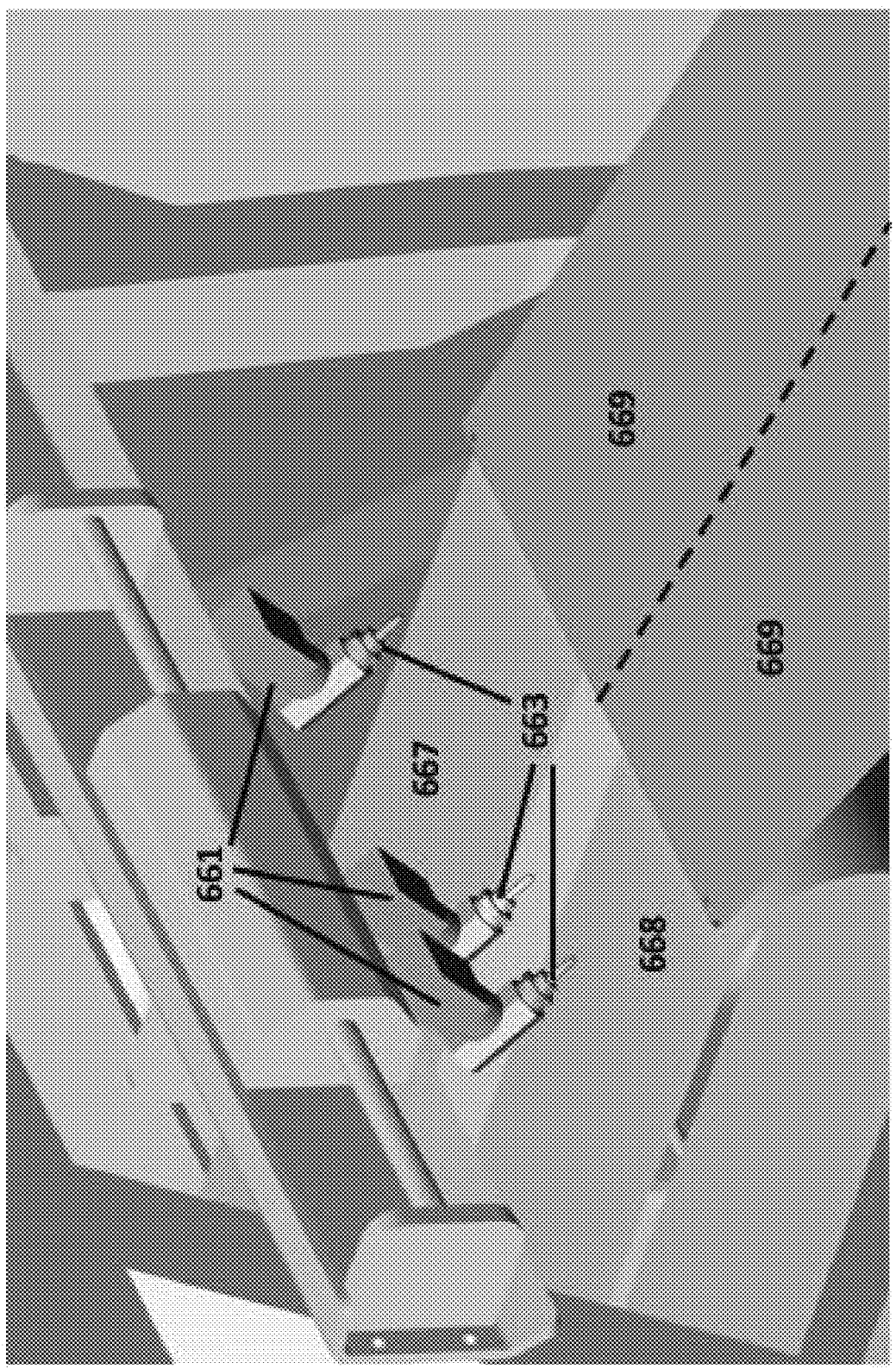
Figure 7E:
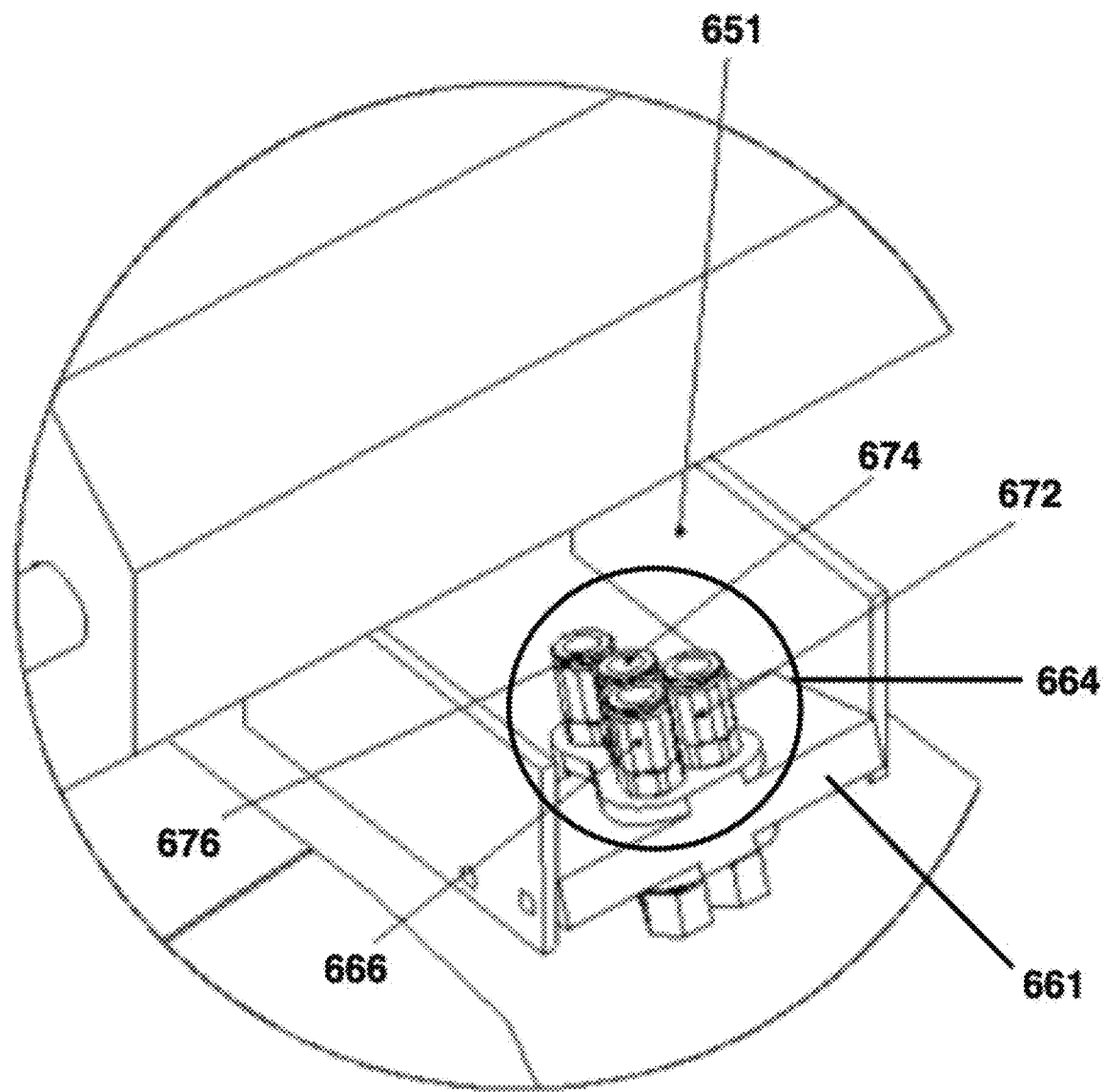

Referring to FIG. 7A and FIG. 7E, a spray-removal robot 651 may include at least one valve 661 that ejects a fluid (e.g., water) from a nozzle 663, and at least one actuator (e.g., air cylinder, motor, linear motor 655 with at least one guide member 657, traditional motor, and solenoid).

As shown in FIG. 7A, the mounting member 653 may extend up from a base member of the conveyor 665 and/or 667, and may extend above the conveyor 665 and/or 667. The support member 659, to which the spray-removal robot 651 is attached, may be horizontally mounted to the mounting member 653, with the nozzle 663 directed towards the first conveyor 665 (which may be the grading conveyor 118). The support member 659 may be sufficiently spaced from the top surface of the conveyor 665 and/or 667, such that a portion 117 may pass under the support member 659 and attached valve(s) 661. The linear motor 655 may drive the sliding of valve 661 back and forth along the guide member 657 in at least substantially horizontal directions.

As shown in FIG. 7E, the spray-removal robot 651 may contain a spray array 664 containing a plurality of spray nozzles. For example, a spray array 664 may contain a left spray nozzle 666, a right spray nozzle 672, and/or a center spray nozzle 674, wherein any of the spray array 664 may include at least one further nozzle in any of the left, right, and center positions. In the example shown in FIG. 7E, the spray array 664 includes a second center spray nozzle 676. In the spray array 664, a single spray nozzle or any combination of spray nozzles can be used in a particular application. For example, a larger number of spray nozzles may be used to remove a larger or wider portion 117 to be removed. For a smaller or more narrow portion 117 to be removed, a single nozzle might be used, or some but not all of the nozzles in the array that are oriented in the same direction (e.g., 674 and 676). If the next portion 117 to be removed is similarly oriented, but also somewhat larger or wider, the left spray nozzle 666 or right spray nozzle 673 could additionally be used. For an even larger or wider portion 117 to be removed, both the left spray nozzle 666 and the right spray nozzle 673 could additionally be used.

A computer may control the operation of the spray-removal robot 651. In operation, the computer may determine a location of a portion 117 to be removed from one or more of: information from the second imaging system 235, the second x-ray image, 3D image, first x-ray image, a signal from the cutting robot 400, movement of the cutting conveyor 214, and movement of the grading conveyor 218. Based on the estimated location of the portion 117 to be removed, the computer may cause the linear motor 655 may drive the sliding of a valve 661 horizontally along the guide member 657 until the valve 661 is oriented over a projected path of the section of the portion 117 to be removed.

Once a valve 661 has been oriented over the projected path of the portion 117 to be removed, the computer may determine, for example, based on the foregoing criteria, exactly when the portion 117 will be in a location and position where the valve 661 can eject fluid through the nozzle 663 to impact the portion 117. Then, the nozzle 663 is controlled to eject fluid along the desired path, and to shut off the fluid when the desired path is completed. In some examples, there may be multiple spray-removal robots 651 where each spray-removal robot 651 has attached a valve 661 and a nozzle 663, and, for example, be disposed to eject fluid at the same time to impact the same section of the portion 117 to be removed, or to impact multiple sections to be removed at the same time.

According to one mode of operation, the cut portions 117 are brought by the first conveyor 665 towards the spray-removal robot 651, and the receiving conveyor 667. The receiving conveyor 667 may convey portions 117 thereon, for example, to an X-ray machine 217, a further grading section 122, a realigning apparatus 800, or to any other conveyor where is to take place further grading, processing, and/or packaging of a fillet 101.

When the computer determines from one or more of the second x-ray image, 3D image, first x-ray image, a signal from the cutting robot 400, movement of the cutting conveyor 214, and movement of the grading conveyor 218, that the location of a section of the portion 117 to be removed (containing bones or exhibiting other undesirable attributes) is the location to be impacted by fluid ejected from the nozzle 663, the computer may then cause the valve 661 to eject fluid through the nozzle 663. When the section of the portion 117 to be removed is impacted by the fluid stream, it may be forced into the space between the first conveyor 665 and the receiving conveyor 667, such that the portion 117 to be removed will not be moved to the receiving conveyor 667, and other portions 117 of the fillet 101 are moved by the motion of the first conveyor 665 onto the surface of the receiving conveyor 667. The spray-removal robot 651 may optionally include a laser sensor to detect the location, alignment, and/or orientation of portions 117 on the receiving conveyor 667.

As shown in FIG. 7B, in particular embodiments, a spray-removal robot 651 may be used to remove portions 117 that have been cut by the cutting machine 216 at an angle 675 with respect to the first conveyor 665. For example, the computer that controls the operation of the spray-removal robot 651 may utilize information from a laser sensor and/or preceding elements of the system 200 (e.g., the cutting robot 400) to identify a portion 117 removed, wherein the position of the portion 117 is described by a plane bisecting the portion 117 at the angle 675. In particular examples, the portion 117 to be removed is the pinbone portion of a fish fillet 101. In such examples, angled cuts were made to track one or more particular feature(s) in the portions 117 for removal; for example, bones, such as the pinbone of a fish fillet 101.

The ejected fluid from the spray-removal robot 651 removes the portion 117 to be removed from the remainder of the fillet 101. In particular embodiments, the portion 117 to be removed is removed from the conveyor system by a force acting upon the section, which may be in addition to, or separate from, the force from the ejected fluid. In one embodiment, there may be sufficient space between the distal end of the first conveyor 665 and the proximal end of the receiving conveyor 667, such that a portion 117 to be removed can be forced into the space between the first conveyor 665 and the receiving conveyor 667, where gravity pulls the section down and away from the conveyors through the space between the distal end of the first conveyor 665 and the proximal end of the receiving conveyor 667.

Figure 8A:
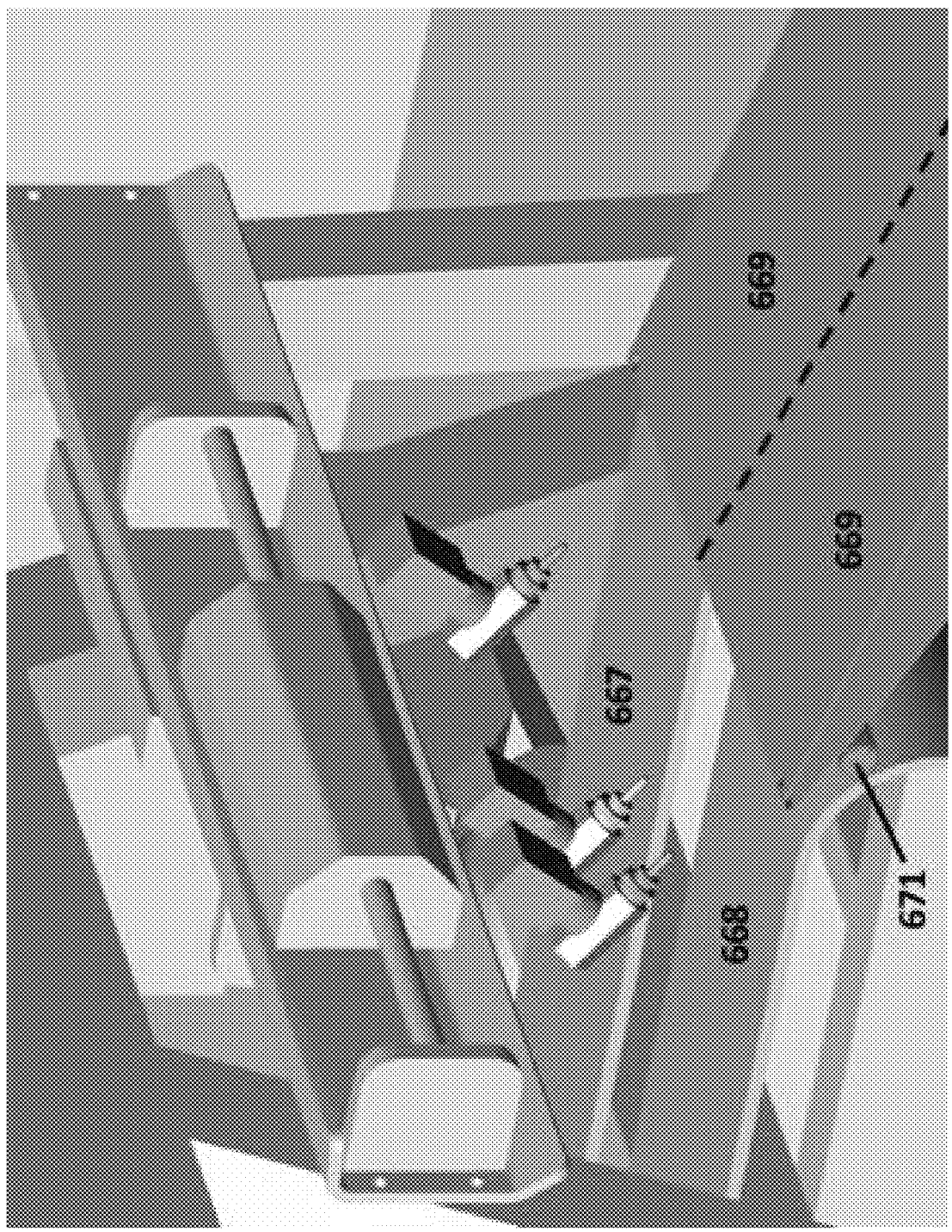
FIG. 8A includes a perspective view of a spray-removal section of a food processing apparatus 200 comprising a plurality of spray-removal robots 651, where a food portion 117 on the same area 669 of a first conveyor 665 passes into the space between the first conveyor 665 and a receiving conveyor 667. A shaft 671 comprised between the distal end of the first conveyor 669 and the proximal end of the receiving conveyor 667 and 668 increases the space between the conveyors.

Referring to FIG. 8A, in one embodiment, there is a shaft 671 between the conveyors that aids in pulling down the section to be removed, for example, by increasing the space between the distal end of the first conveyor 669 and the proximal end of the receiving conveyor 667 and 668. In some modes of operation, if the space between the distal end of the first conveyor 669 and the proximal end of the receiving conveyor 667 and 668 is increased sufficiently to aid in the removal of particular portions 117, the transfer of remaining portions from the first conveyor 665 to the receiving conveyor 667 may by negatively impacted by the spacing; for example, the transfer may not maintain accurate location and/or alignment of portions 117.

Therefore, in particular embodiments, a plate or conveyor system (FIG. 8(B-C)) with a slot 670 is positioned between the first conveyor 665 and the receiving conveyor 667, wherein the slot 670 is sized and positioned for the removal of the portion 117 impacted by the fluid from the spray-removal robot 651. For example, the slot 670 can be of a size at least as large as the portion 117 to be removed, and the portion 117 to be removed may be moved through the slot 670, for example, by a spray-removal robot 651, or by an independent actuator or robot. The size of the slot 670 may be fixed, or it may be variable, controlled by an actuator.

In some modes of operation defining the size and/or position of the slot 670 between a first receiving conveyor 667 and a second receiving conveyor 668, the first receiving conveyor 667 and the second receiving conveyor 668 may be moved in the direction perpendicular to the conveyor's movement 119. The first receiving conveyor 667 and the second receiving conveyor 668 may be moved together in particular embodiments, or independently in other embodiments. When moved together, the slot 670 is always approximately the same width, and the first receiving conveyor 667 and the second receiving conveyor 668 may be moved, such that the slot 670 is beneath the section of the portion 117 to be removed. When the first receiving conveyor 667 and the second receiving conveyor 668 are moved independently, the width of the slot 670 (along with its position beneath the received portions 117) can be adjusted, for example, according to information from the computer that controls the operation of the spray-removal robot 651.

Figure 8B:
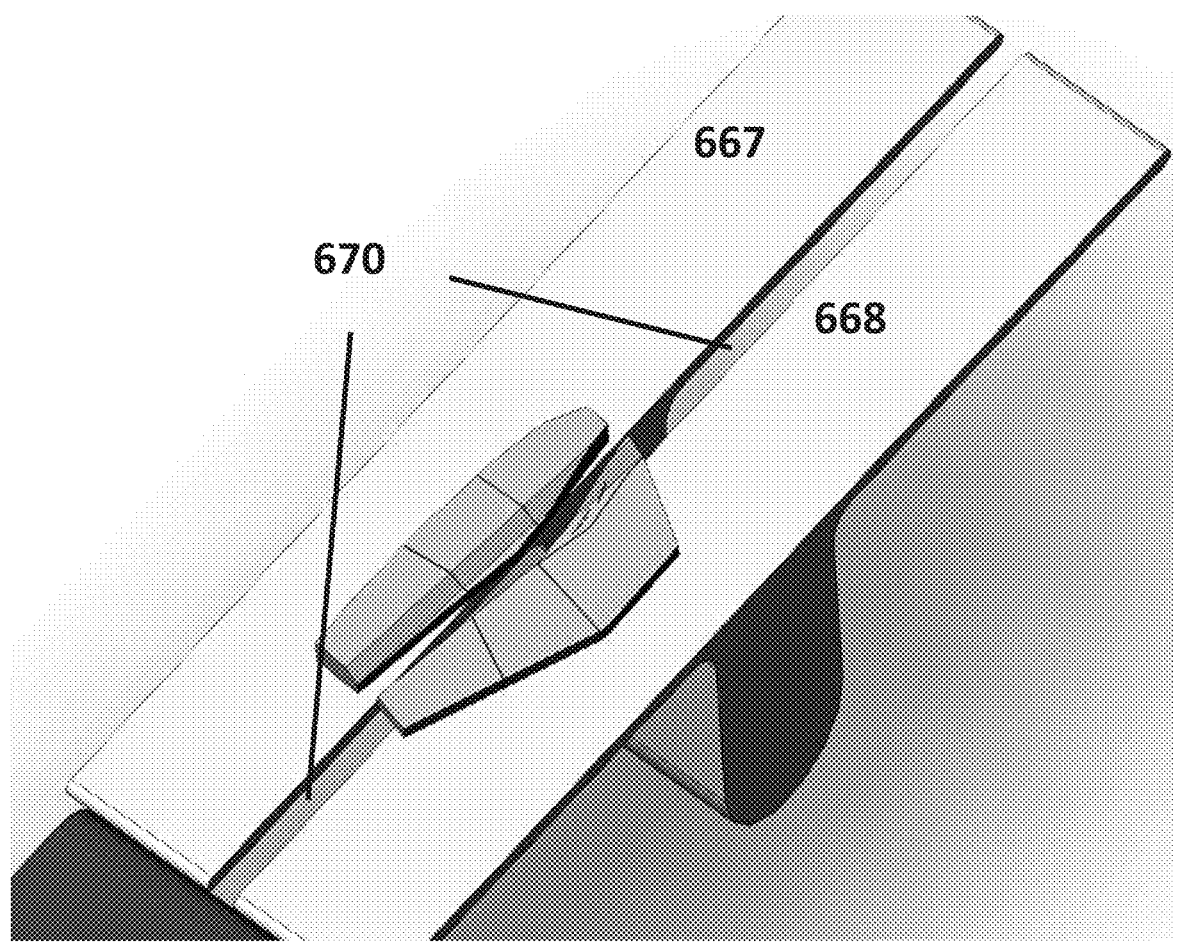
FIG. 8B includes a perspective view of a slot 670 positioned in certain embodiments between a first receiving conveyor 667 and a second receiving conveyor 668, wherein the portion 117 to be removed may be moved through the slot 670 as the fillet 101 is passed over it.
Figure 8C:
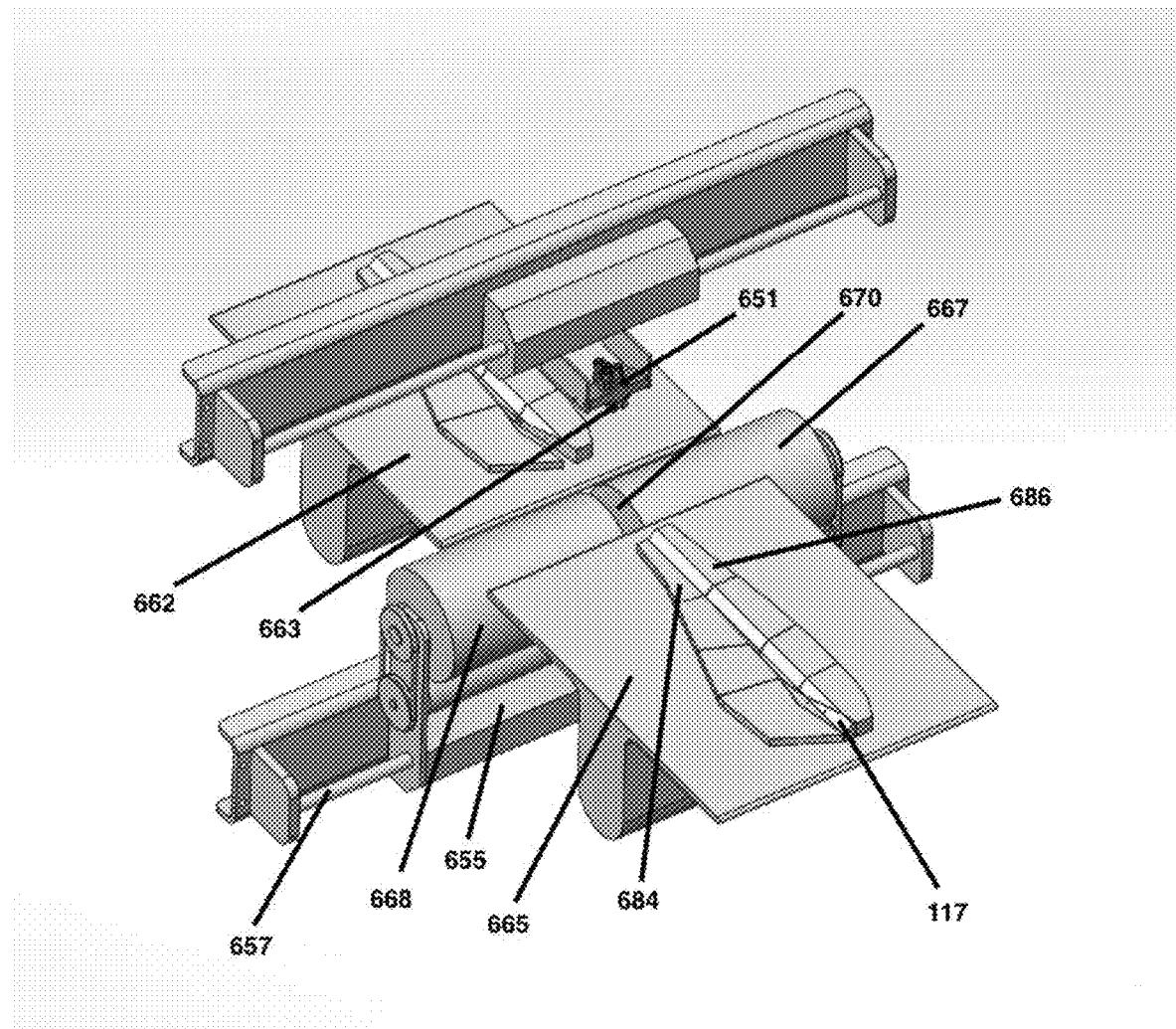
FIG. 8C includes a perspective view of a particular spray-removal section of a food processing apparatus 200 of the type comprising a slot 670 positioned between the first receiving conveyor 667 and a second receiving conveyor 668, wherein the portion 117 to be removed may be moved through the slot 670 as the fillet 101 is passed over it. In the spray-removal section of FIG. 8C, the receiving conveyors 667, 668 have a minimal length in the direction of the conveyor's movement 119, such that the receiving conveyor system is essentially a roller system.

Referring to FIG. 8C, the plate or conveyor system may have a length of zero or a minimal length in the direction of the conveyor's movement 119, such that the plate or conveyor system is a roller system or is essentially a roller system, respectively. Such a roller system may define the slot 670 between the first receiving conveyor 667 and the second receiving conveyor 668, each having a circular rotation. Such a roller system may include at least one actuator (e.g., air cylinder, motor, linear motor 655 with at least one guide member 657, traditional motor, and solenoid). The linear motor 655 may drive the sliding of the first receiving conveyor 667 and the second receiving conveyor 668 back and forth along the guide member 657 in at least substantially horizontal directions.

In some modes of operation, the plate or conveyor system aids in pulling down the portion 117 to be removed, for example, by controlling the size and position of the slot 670 between the first receiving conveyor 667 and the second receiving conveyor 668, such that the portion 117 to be removed falls through the slot 670 when the fillet 101 is moved by the combined action of the first receiving conveyor 667 and the second receiving conveyor 668 to a further receiving conveyor 662. As shown in FIG. 8C, a fillet 101 is carried to the plate or conveyor system by the first conveyor 665. If the portion(s) 684, 686, of the fillet 101 contacting the plate or conveyor system is intended to be moved to the further receiving conveyor 662, the size of the slot 670 is reduced or minimized, or the position of the slot 670 is moved away from beneath the portion(s) 684, 686, to ensure that the portion(s) 684, 686 do not fall through the slot 670. Just before a portion 117 to be removed contacts the plate or conveyor system, the first receiving conveyor 667 and/or the second receiving conveyor 668 are moved to define the slot 670 to an appropriate size that the portion 117 to be removed falls through the slot 670.

Figure 8D:
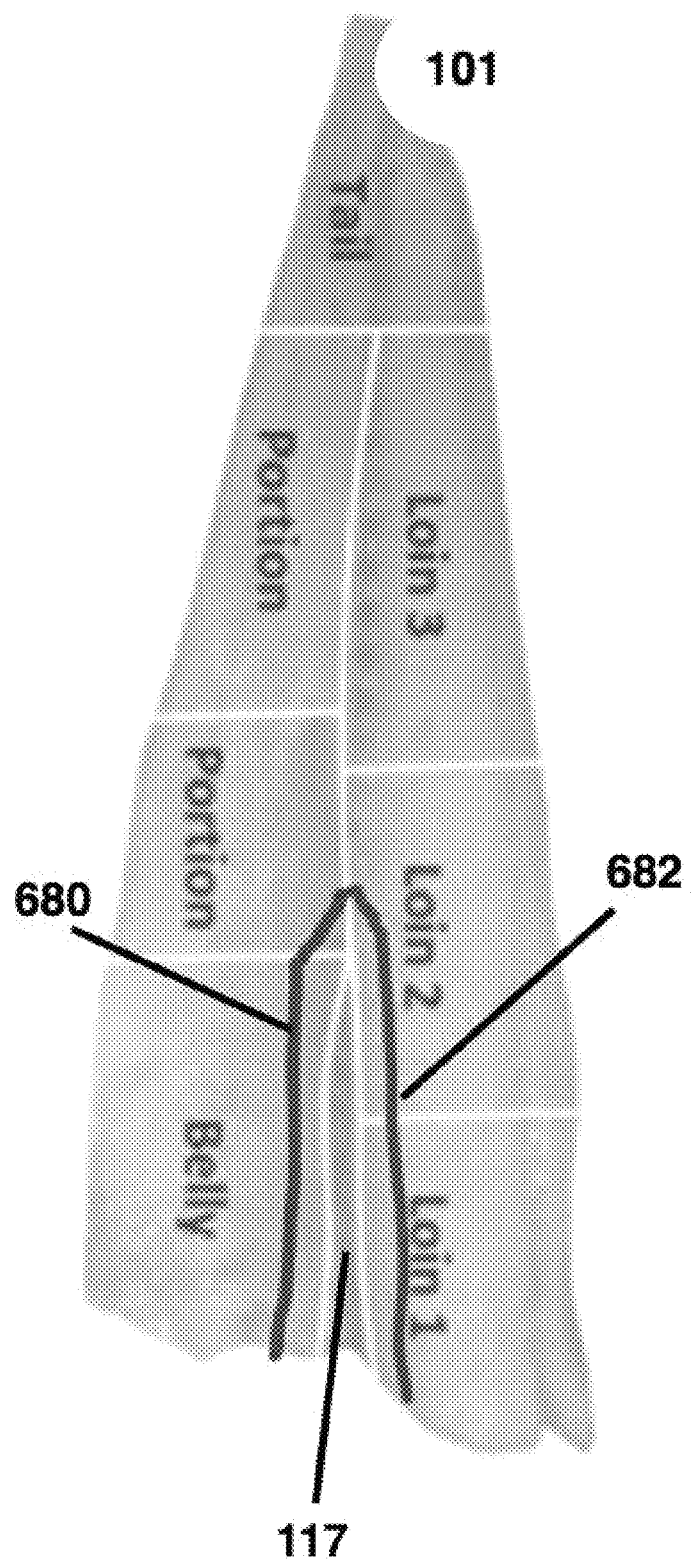
FIG. 8D includes a diagram of a fillet 101 as may be processed through a spray-removal section of a food processing apparatus 200 of the type comprising a slot 670 positioned between the first receiving conveyor 667 and a second receiving conveyor 668. In such a spray-removal section, the first receiving conveyor 667 may be positioned to contact the left edge 680 of the portion 117 to be removed, and the second receiving conveyor 668 may be positioned to contact the right edge 682 of the portion 117 to be removed.

For example, to remove the portion 117 to be removed from the fillet 101 shown in FIG. 8D, the first receiving conveyor 667 may be positioned to contact the left edge 680 of the portion 117 to be removed, and the second receiving conveyor 668 may be positioned to contact the right edge 682 of the portion 117 to be removed. In some examples, the first receiving conveyor 667 and/or the second receiving conveyor 668 may be positioned to contact the fillet 101 at a suitable distance from the left edge 680 and right edge 682 of the fillet 101, respectively, so as to define the slot 670 to be wider than the width of the portion 117 to be removed. The first receiving conveyor 667 and/or the second receiving conveyor 668 may then be controlled to follow the path of the edge of the portion 117 to be removed. Referring to FIG. 8C, once the portion 117 to be removed arrives in the target path of the spray-removal robot 651, one or more spray nozzles 651 are activated to force the portion 117 to be removed through the slot 670. Once the portion 117 to be removed has been removed through the slot 670, the spraying may be stopped, and the location and movement of first receiving conveyor 667 and the second receiving conveyor 668 are prepared for the next fillet 101.

In a grading section 122, the grading robot(s) 224 may be able to remove portions 117 of a fish fillet 101 still containing bones from the grading conveyor 218 and into the at least one tub 258. The at least one grading robot 224 may be able to move the portions 117 of a fish fillet 101 directly onto one of the plurality of processing conveyors 226. The grading robot(s) 224 may be able to move in the direction of movement of the grading conveyor 218, so that the grading robot(s) 224 remain above the portions 117 while the movement of the portions 117 is carried out.

In some embodiments, the at least one grading robot 224 may be capable of moving to a side of the grading conveyor 218, such that the grading robot 224 is not directly above the grading conveyor 218 but rather, may be directly above one of the plurality of processing conveyors 226 or the at least one tub 258. In some embodiments, a top surface 262 of at least one of the plurality of processing conveyors 226 may be at least substantially coplanar with a top surface 264 of the grading conveyor 218. In particular embodiments, the alignment and orientation of the portions 117 of a fish fillet 101 may be substantially preserved when a grading robot 224 moves the portions 117 from the grading conveyor 218 to a processing conveyor 226 having a top surface 262 substantially coplanar with the top surface 264 of the grading conveyor 218. In particular embodiments, a top surface 262 of the processing conveyor 226 may be lower than the top surface 264 of the grading conveyor 218, such that, when moved, the portions 117 are slid off the grading conveyor 218 by a grading robot 224 and dropped onto the processing conveyor 226.

In some embodiments, a fish fillet 101 may be cut and portions 117 of the cut fish fillet 101 graded at the same time. In particular embodiments, the grading is performed simultaneously as part of the cutting process. For example, the cutting robot 400 may be the same robot as the grading robot 600.

In some embodiments, a grading robot 224 may organize the portions 117 of a fish fillet 101 to different areas (portion positions 256) of the grading conveyor 218 according to different characteristics of the portions 117. For example, in some embodiments, a grading robot 224 may be controlled to move the tail portion of a fish fillet 101 to a certain portion position 256 of the grading conveyor 218, and to move all of the loin portions of the fish fillets 101 to another portion position 256 of the grading conveyor 218. In some embodiments, a grading robot 224 may organize the portions 117 of a fish fillet 101 according to a weight of the portions 117. For example, the grading robot 224 may be controlled to move all portions 117 having a weight within a first range of weight to a certain portion position 256 of the grading conveyor 218, and optionally to move all portions 117 having a weight within a second range of weight to another portion position 256 of the grading conveyor 218. In some embodiments, the at least one grading robot 224 may organize the portions 117 of a fish fillet 101 according to one or more metric and/or criterion of size, type, or quality. The different portion positions 256 of the grading conveyor 218 may be designated as leading to different processes. For example, the different portion positions 256 of the grading conveyor 218 may lead to different processing conveyors 226 or trays, which in turn, may lead to any of multiple different processes. Such processes may include one or more of packaging, breading, freezing, further cutting, and any other known process for food processing.

In some embodiments, a grading robot 224 may be able to move one or more portion(s) 117 from a group of portions 117 that are oriented parallel to each other without disturbing the alignment and orientation of the other portions 117 in the group. For example, with reference to FIG. 1, the grading robot 224 may be able to move portion 117 two from portions 117 four and five, without disturbing the alignment and orientation of portions 117 four and five. In particular embodiments, the alignment and orientation of the cut portions 117 may be substantially preserved when the grading robot 224 moves the portions 117 from the grading conveyor 218. The substantial preservation of orientation and/or alignment of portions during grading may provide an advantage over previously known grading robots that are limited to grading portions 117 that are in series. For example, previously known grading robots, such as scrapers, move across a conveyor and remove any portions 117 along a path of the scraper. Thus, previously known grading robots are unable to grade a single portion 117 of a group of portions 117 that are oriented parallel to each other.

At least one of the grading robot(s) 224 may be able to move a portion 117 of a fish fillet 101 without damaging the delicate flesh of the portions 117. For example, at least one grading robot 224 may be a needle grading robot 600 as described in FIG. 6(A-E), which includes at least one needle 602 that can be inserted into the flesh of each portion 117 without damaging the flesh. A computer, based on one or more of the second x-ray image, 3D image, first x-ray image, and estimated location of the portion 117 following the activity of the cutting robot 400, may control the needle grading robot 600 to a location in line with a center area of a portion 117 to be moved. The computer may then control the needle grading robot 600 to lower the needle(s) 602 into the center area of the portion 117 to be moved. The needle grading robot 600 may then be directed to move the portion 117 to a portion position 256, by moving the needle(s) 602 to the portion position 256 without retracting the needle(s) 602 from the portion 117, according to the selected function of the needle grading robot 600.

Having at least one needle 602 to puncture the portions 117 may provide an advantage over previously known grading robots. For example, previously known robots used to grade delicate food products often damage the flesh by breaking, crushing, or tearing the flesh of the portion 117 while moving the portion 117, for example, by pressing the flesh between two members. On the other hand, by puncturing the portions 117 with at least one needle 602, the flesh may not be broken, crushed, torn, or otherwise damaged. Furthermore, using at least one needle 602 to puncture the portions 117 may allow the alignment and orientation of the portions 117 to be maintained during grading. Contrariwise, pressing the portions 117 between two members can cause folds in the flesh that can disrupt the alignment or orientation of the portions 117.

In some embodiments, the alignment and orientation of the portions 117 may have to be maintained during the grading process for subsequent processes such as, for example, packaging and freezing processes. Accordingly, moving the portions 117 with at least one needle 602 may also provide an advantage over moving the portions 117 with scrapers, which are often used to move portions 117 of food articles 101 on a conveyor by placing a scraper to one side of the portion 117, and pushing the portion 256 to a desired location. Using a scraper to move the portions 117 can also cause folds in the flesh, which can disrupt the alignment and orientation of the portions 117. On the other hand, using at least one needle 602 to move the portions 117 may help to maintain the alignment and orientation of the portions 117 for further processes. For example, multiple needles 602 may be used to puncture a portion 117 and the multiple needles 602 may be spaced throughout the portion 117. Having multiple needles 602 contacting multiple locations throughout the portion 117 while the portion 117 is moved may assist in maintaining the alignment and orientation of the portion 117 for further processes.

Referring again to FIG. 6A, a needle grading robot 600 may include a first mounting member 603, a second mounting member 604, a first actuator (e.g., air cylinder 606, motor, linear motor, traditional motor, and solenoid), a second actuator 608, a first guide member 610, a second guide member 612, a horizontally movable support member 614, a vertically movable support member 616, a laser sensor 618, at least one needle 602, and a release mechanism 620.

The first mounting member 603 and second mounting member 604 may extend up from a base member 622 of the grading conveyor 218, and may extend above the grading conveyor 218. The first guide member 610 may be horizontally mounted to the first mounting member 603 and the second mounting member 604. The first guide member 610 may be sufficiently spaced from the top surface of the grading conveyor 218, such that a portion 117 may pass thereunder. A length of the first guide member 610 may be longer that than a width of the grading conveyor 218, such that the first guide member 610 extends out past the first and second mounting members 603, 604, and extends out past side surfaces of the grading conveyor 218 to allow for a grading robot 224 to place a portions 117 directly onto processing conveyors 226 next to the grading conveyor 218, as discussed above.

The horizontally movable support member 614 may be slidable back and forth along the first guide member 610 in at least substantially horizontal directions. The second guide member 612 may be mounted to the horizontally movable support member 614. The vertically movable support member 616 may be slidable up and down along the second guide member 612 in at least substantially vertical directions.

The first air cylinder 606 may be attached at one end to the horizontally movable support member 614, and may be attached at another end to the second mounting member 604. The second air cylinder 608 may be attached at one end to the second guide member 612, and attached at another end to the vertically movable support member 616. At least one needle 602 may be attached to a lowermost portion 624 of the vertically movable support member 616, and a length of the needle(s) 602 may be oriented in a direction at least substantially normal to the top surface of the grading conveyor 218. In some examples, the needle(s) 602 may have an outer diameter, for example and without limitation, within a range of 0.5 mm to 2 mm; or within a range of 0.1 mm to 0.4 mm; within a range of 2 mm to 5 mm. The release mechanism 620 may be attached to the lowermost portion 624 of the vertically movable support member 616 proximate at least one needle 602. The laser sensor 618 may be disposed proximate the second mounting member 604, and may track the position of the second guide member 612 and vertically movable support member 616.

A computer may control the operation of the at least one grading robot 224. In operation, the computer may determine an estimated location of a portion 117 to be moved based on one or more of the second x-ray image, 3D image, first x-ray image, movement of the cutting conveyor 214, and movement of the grading conveyor 218. Based on the estimated location of the portion 117 to be moved, the computer may cause the horizontally movable support member 614 to move horizontally until at least one needle 602 attached to the lowermost potion of the vertically movable support member 624 is oriented over a center of a projected path of the portion 117 to be moved. The laser sensor 618 may be used to determine when the vertically movable support member 616 is correctly oriented over the center of the projected path of the portion 117. The horizontally movable support member 614 is moved, for example, by pumping air into or sucking air out of a first air cylinder 606. By pumping air into or sucking air out of the first air cylinder 606, the first air cylinder 606 may be caused to extend or retract. By extending or retracting the first air cylinder 606, the first air cylinder 606 may push or pull the horizontally movable support member 614 along the first guide member 610. By pushing or pulling the horizontally movable support member 614, the at least one needle 602 may be moved along the first guide member 610 and across the width of the grading conveyor 218.

Once at least one needle 602 has been oriented over the center of the projected path of the portion 117 to be moved, the computer may determine, for example, based on the estimated location of the portion 117 and based on the movement of the grading conveyor 218, exactly when the portion 117 will be directly underneath the needle(s) 602. The computer may then cause the vertically movable support member 624 to move downwards towards the portion 117 such that the needle(s) 602 penetrates at least partially the flesh of the portion 117 to be moved. The vertically movable support member 624 is moved downwards by the action of a second actuator, for example, by pumping air into a second air cylinder 608 and extending the second air cylinder 608. Once the at least one needle 602 has penetrated the flesh of the portion 117 to be moved, that portion 117 can be moved by moving the horizontally movable support member 614 according to the above described procedure.

After the portion 117 has been moved by a needle grading robot 600, at least one needle 602 may be retracted from the flesh of the portion 117. In some embodiments, the procedure may happen naturally, for example, when the portions 117 are dropped into a tub 258. In such examples, the portions 117 may naturally fall of the needle(s) 602. In some embodiments, a release mechanism 620 may be used to press against the portion 117 as the at least one needle 602 is lifted. At least one needle 602 may be lifted, for example, by sucking air out of a second air cylinder 608 and retracting the second air cylinder 608. By retracting the second air cylinder 608, the vertically movable support member 624, to which the needle(s) 602 is attached, may be pulled up along the second guide member 612 by the second air cylinder 608. Once the vertically movable support member 624 has been moved up and the at least one needle 602 retracted from the portion 117, the grading process may begin again and may repeat the above described process in relation to another portion 117 to be moved.

In some embodiments, a needle grading robot 600 may include a plurality of needles 602 oriented linearly in a direction parallel to the direction the grading conveyor 218 is moving. In some embodiments, a needle grading robot 600 may include a plurality of needles 602 oriented linearly in a direction perpendicular to the direction the grading conveyor 218 is moving. In some embodiments, a needle grading robot 600 may include a plurality of needles 602 oriented in a shape of one or more of, for example and without limitation, a square, circle, triangle, or cross. For example, the orientation of the plurality of needles 602 may be chosen based on a projected function of a specific needle grading robot 600. For example, based on the shape of a portion 117 to be moved, certain orientations of the plurality of needles 602 may be better suited to maintain the alignment and orientation of the portion 117.

In some embodiments, where the needle grading robot 600 includes a plurality of needles 602, the plurality of needles 602 may all be pointed in a direction substantially normal to the top surface of the grading conveyor 218. In some embodiments, the plurality of needles 602 may be pointed in directions not substantially normal to the top surface of the grading conveyor 218. For example, the plurality of needles 602 may be pointed in directions, such that if the plurality of needles 602 touched the top surface of the grading conveyor 218, an angled formed between each needle 602 of the plurality of needles 602 and the top surface of the grading conveyor 218 would be an acute angle. In some embodiments, the plurality of needles 602 may include crossing needles 602.

In some embodiments, a grading robot 224 may lift a portion 117 from the top surface of the grading conveyor 218 in order to place the portion 117 in a portion position 256 on the grading conveyor 218, or to lift the portion 117 from the top surface of the grading conveyor 218 to remove the portion 117 from the grading conveyor 218, for example and without limitation, into a tray or bin or onto another conveyor entirely. In particular embodiments, a grading robot 224 that lifts a portion 117 from the top surface of the grading conveyor 218 may comprise a gripper (a "gripper grading robot" 601). As described above with regard to a robotic arm 500, a gripper may include, for example and without limitation, a hook that can be slipped under a portion 117 to be removed, or stuck into the portion 117 to be removed, at least two members that can clamp or press the portion 117 between the two members, a suction member that uses a vacuum to suck the portion 117 against the gripper, and/or any gripper described in U.S. Patent Application Publication No. 2012/0307013 A1.

Figure 6A:
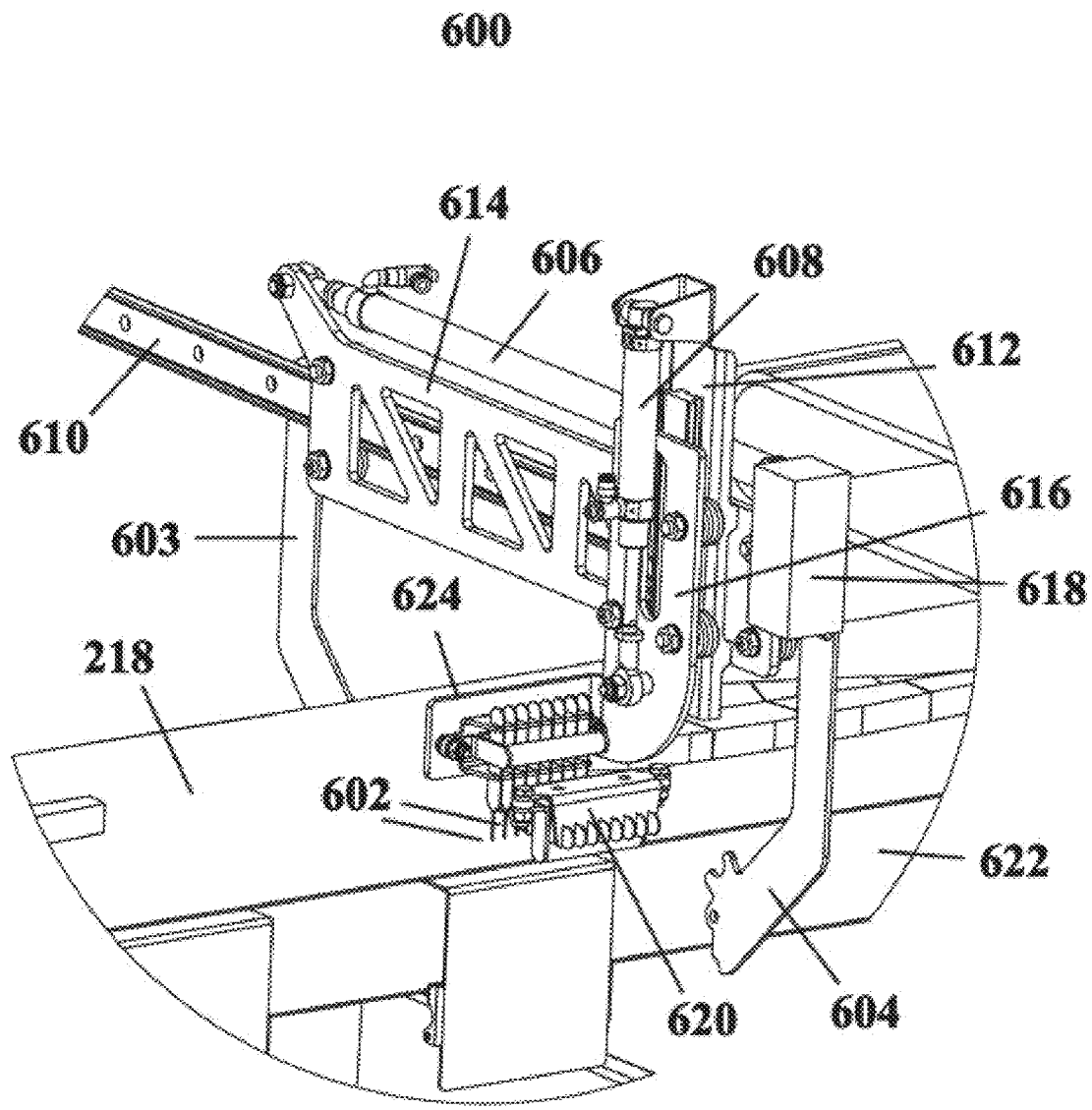
FIG. 6A includes a perspective view of an example of a needle grading robot of a food processing apparatus.
Figure 6B:
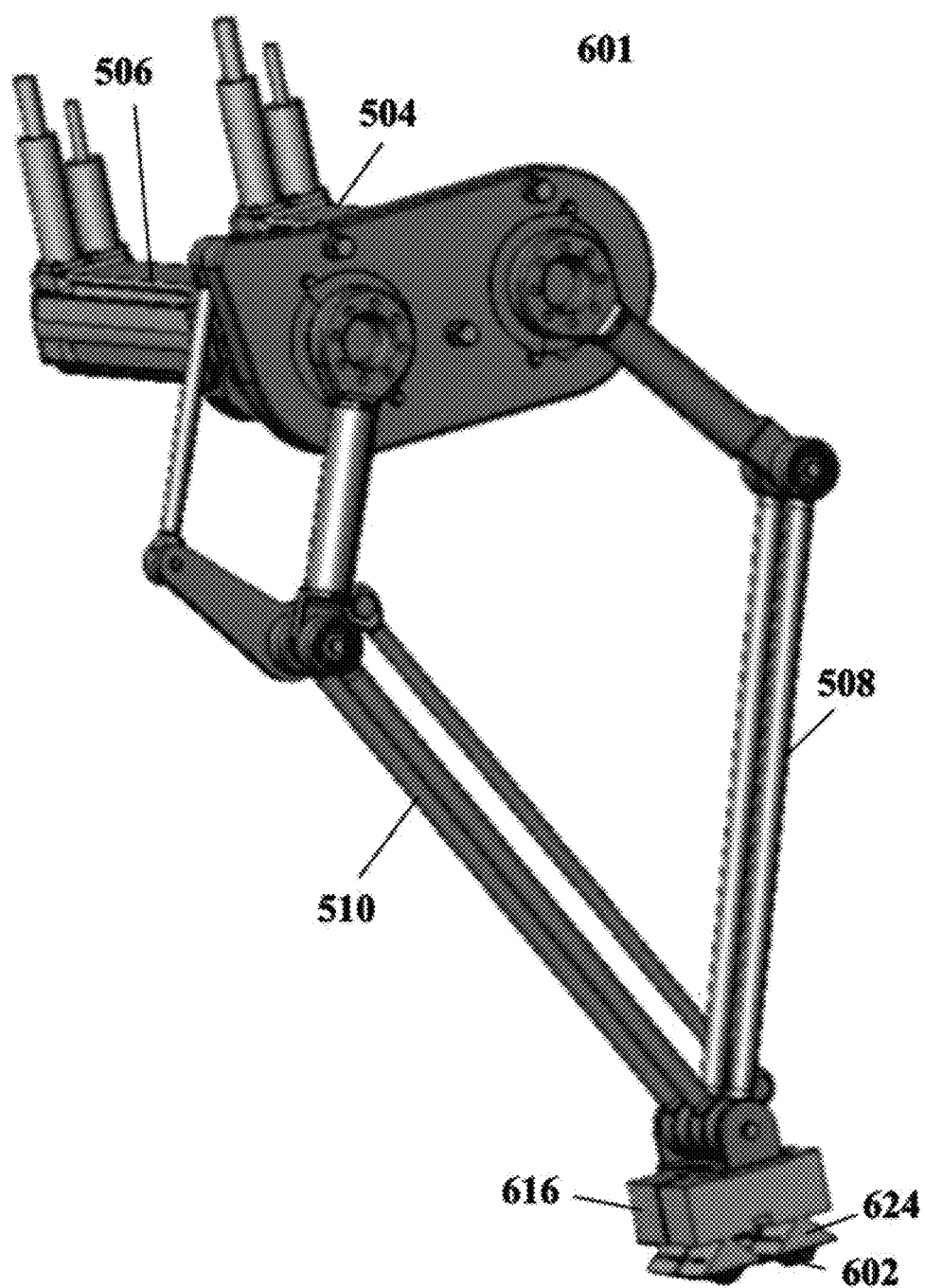
FIG. 6B includes a perspective view of a further example of a needle grading robot of a food processing apparatus.
Figure 6C:
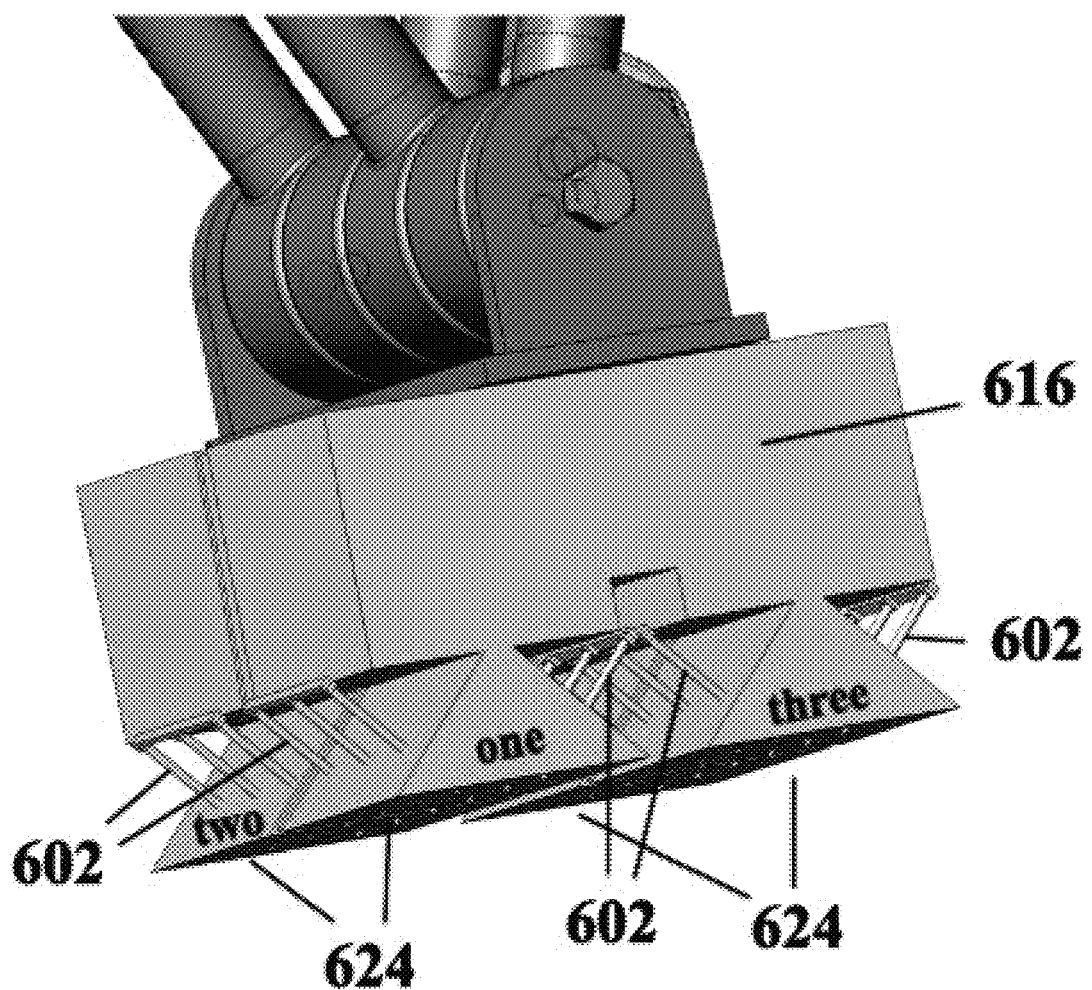
In FIG. 6C, the needles of the array are positioned proximate the vertically movable support member.

As shown in FIG. 6B, a needle grading robot 600 may be adapted to lift a portion 117 from the top surface of the grading conveyor 218 in order to place the portion 117 in a portion position 256 on the grading conveyor 218, or to lift the portion 117 from the top surface of the grading conveyor 218 to remove the portion 117 from the grading conveyor 218. FIG. 6(C-D) show at least one needle 602 attached to a lowermost portion 624 of the vertically movable support member 616 according to particular embodiments. In the needle grading robot 600 of FIG. 6C, the at least one needle 602 is disposed in eight sets of three needles 602, wherein two sets of three needles 602 are disposed in an area of the distal surface of the lowermost portion 624 of the vertically movable support member 616, and the needles 602 are positioned proximate the vertically movable support member 616. In the needle grading robot 600 of FIG. 6C, the distal surface of the lowermost portion 624 of the vertically movable support member 616 is separated into four areas.

Figure 6D:
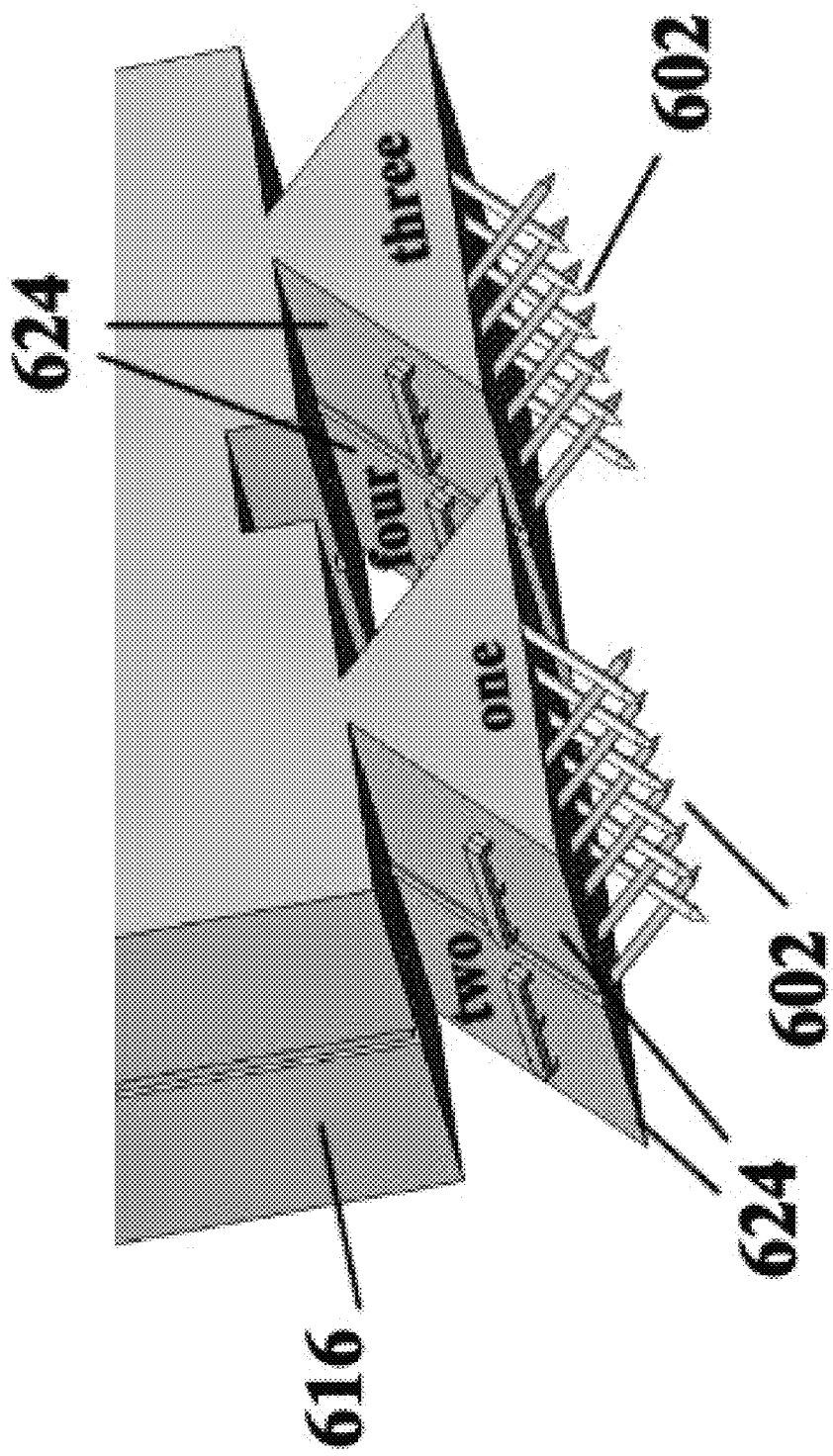
In FIG. 6D, the needles of the array are positioned distal the vertically movable support member.
Figure 6E:
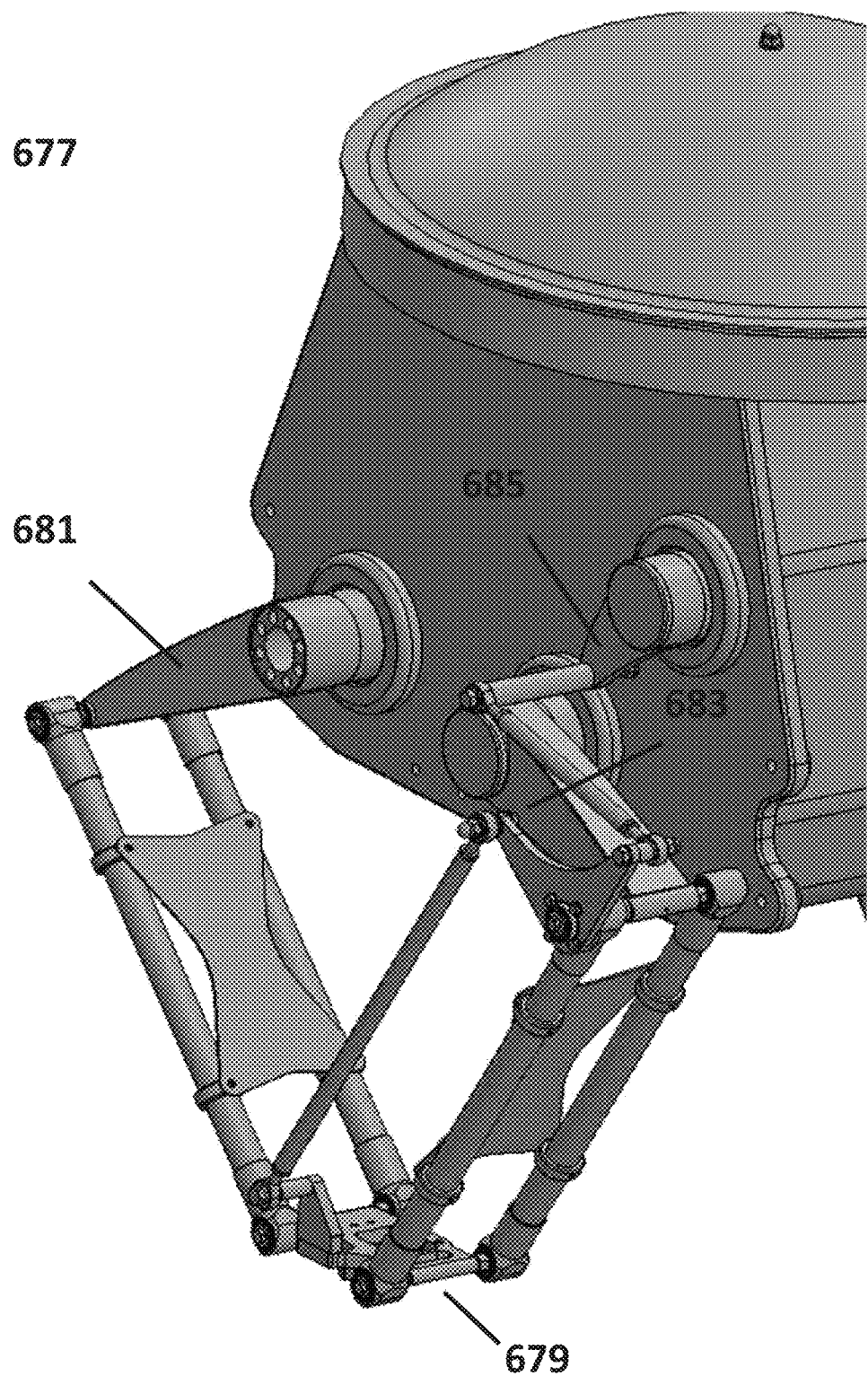
FIG. 6E includes a perspective view of an example of a three degrees of freedom robot 677 that may be utilized in some embodiments, for example, as a spray-removal robot 651. In particular embodiments, a three degrees of freedom robot 677 comprises a first primary axis 681 and a second primary axis 683 that can control the location of a parallel plate 679 in the Y and Z directions, and a third axis 685 that can tilt the parallel plate 679 in a plane that is perpendicular to the direction of the conveyor.

To grip a portion 117 to slide or lift the portion 117, the needles 602 are moved to a position distal the vertically movable support member 616, piercing the flesh of the portion 117, as shown in FIG. 6D. Any method may be used to extend the needles to a position distal the vertically movable support member 616, for example, air compression. The sets of needles 602 shown in FIGS. 6(C-D) may be moved separately in some examples, according to the grading application. For example, to move small portions 117 only needle 602 set "one" may be extended; to move a bigger, longer portion 117, both needle 602 sets "one" and "two" may be extended; and to move a shorter, wider portion 117, both needle 602 sets "one" and "three" may be extended; and to move a longer, bigger portion 117, all of needle 602 sets "one," "two," "three," and "four" may be extended.

In some embodiments, a needle grading robot 600 or gripper grading robot 601 may be capable of rotation in a plane parallel to the surface of the grading conveyor 218, for example, to orient or reorient a portion 117 on the surface of the grading conveyor 218. For example, as shown in FIG. 4(A-B) with regard to a cutting robot 400, the needle grading robot 600 or gripper grading robot 601 may include a motor 414 that can rotate, directly or indirectly, the vertically movable support member 616. Thus, in some examples, the vertically movable support member 616 can rotate around any axis in its moving envelope that is parallel to the x-axis (e.g., the surface of the grading conveyor 218).

In particular embodiments, a needle grading robot 600 (e.g., as shown in FIGS. 6(C-D)) may be utilized to lift a plurality of portions 117, for example, before they are moved to a different position on the top surface of the grading conveyor 218, or removed from the top surface of the grading conveyor 218. Such embodiments may in some examples provide the particular advantage of advantage to increasing capacity, for example, when the plurality of portions 117 are removed from the top surface of the grading conveyor 218. In some examples, a single needle grading robot 600 may be utilized to lift a plurality of portions 117 of a fish fillet 101 that each contain, for example, a bone or bone fragment. For example and without limitation, and with reference to FIG. 1, a single needle grading robot 600 may be utilized to lift portions 117 "ten" and "twelve." In this example, both needle 602 sets "one" and "two" may be utilized to grip portion 117 "ten," and needle 602 set "four" may be utilized to grip portion 117 "twelve." For example and without limitation, the needle grading robot 600 may be moved to the desired position (e.g., a different position on the top surface of the grading conveyor 218, or a position that is removed from the top surface of the grading conveyor 218), and both pieces may be released from the gripper, either individually, or at the same time. By way of further example, the needle grading robot 600 may be moved to a first desired position of a first portion 117 (e.g., a different position on the top surface of the grading conveyor 218), the first portion 117 may be released from the gripper at the first position, the needle grading robot 600 may then be moved to a second desired position of a second portion 117, and the second portion 117 may be released from the gripper at the second position (e.g., a position that is removed from the top surface of the grading conveyor 218).

By lifting the portion 117 from the top surface of the grading conveyor 218, the grading robot(s) 224 may maintain an orientation of the portion 117 while moving the portion 117 to another conveyor. For example, moving a portion 117 from the grading conveyor 218 to a processing conveyor 126, wherein the top surface 164 of the grading conveyor 118 is substantially coplanar with the top surface 162 of the processing conveyor 126, sliding the portion 117 along the top surfaces of the grading conveyor 218 and another conveyor, may subject the portion 117 to conveyors traveling in different directions when the portion 117 is moved from the grading conveyor 218 to the other conveyor. Accordingly, the portion 117 is likely to at least partially rotate such that the orientation of the portion 117 is disturbed. Thus, by lifting the portion 117, a change in orientation may be avoided.

In some embodiments, at least one grading robot 224 may slide the portion 117 along the top surface of the grading conveyor 218 to a portion position 256 on the grading conveyor 218, as described above. In some embodiments, the grading robot(s) 224 may slide the portion 117 completely off of the top surface of the grading conveyor 218 and into a tray or tub 258 or onto another conveyor, as described above. In particular embodiments, a grading robot 224 that slides a portion 117 along the top surface of the grading conveyor 218 to a portion position 256 on the grading conveyor 218 may be a two degrees of freedom grading robot 700.

Figure 9A:
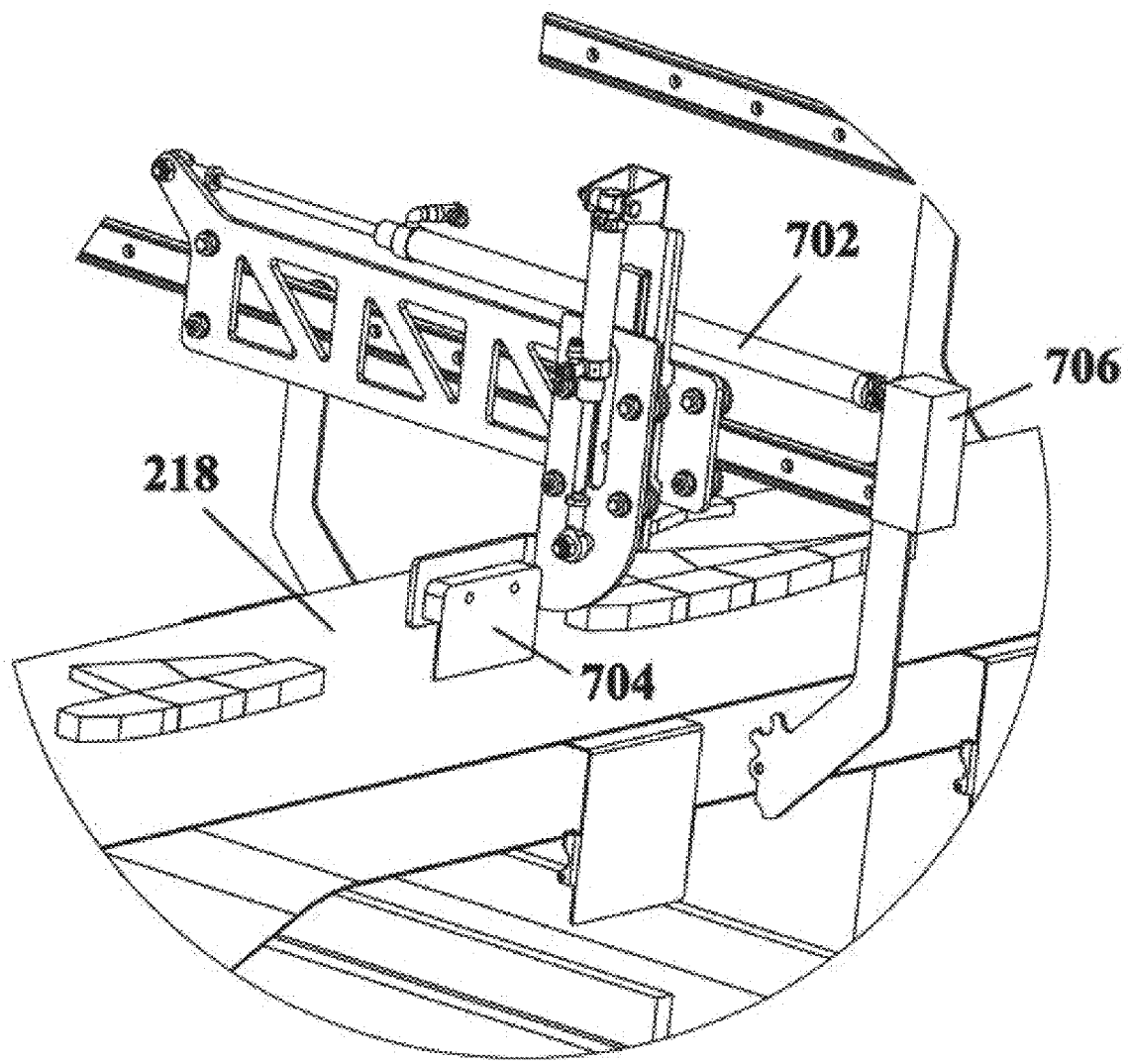
FIG. 9A includes a perspective view of a two degrees of freedom grading robot of a food processing apparatus.
Figure 9B:
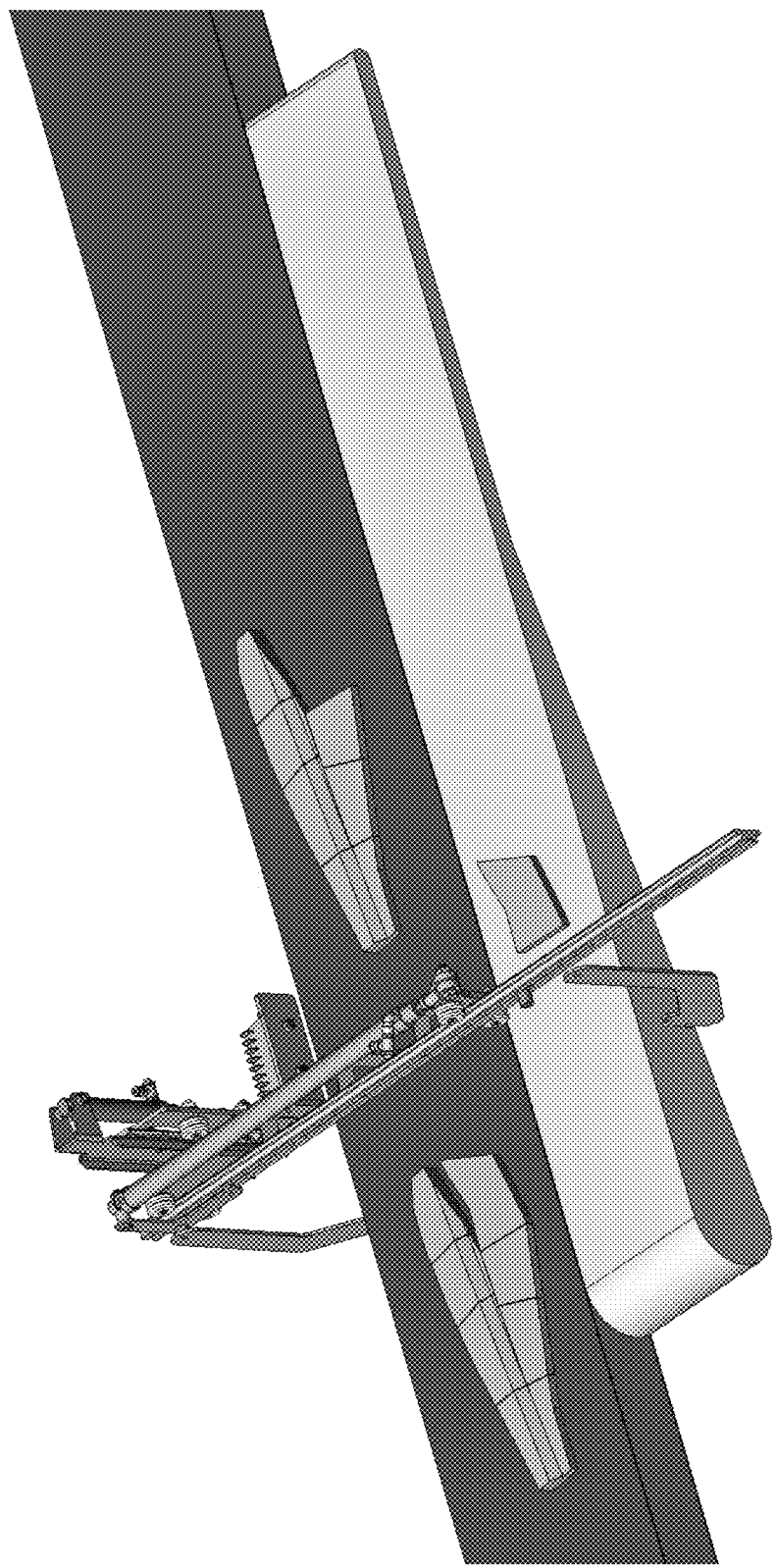
FIG. 9B includes a view of the two degrees of freedom grading robot disposed to transfer at least one portion of the food article from a first conveyor to a second conveyor. In this example, the second conveyor is oriented in parallel with respect to the first conveyor. However, the second conveyor may alternatively be oriented perpendicularly, or at any other angle, with respect to the first conveyor. Furthermore, any grading robot (e.g., one, two, three, four, or more degrees of freedom grading robots described herein) may be utilized to transfer a portion of the food article from a first to a second conveyor. Referring again to FIG. 9B, in this illustration only one portion is transferred from a first to a second conveyor. However, any number of portions may be transferred, depending on the particular grading robot utilized. Conveyor belts may be positioned to keep the transfer between the belts as smooth as possible. Furthermore, a middle plate can potentially be included, and the second conveyor may in some examples be positioned a little bit lower than the first conveyor that originally comprises the portion(s) on its surface.
Figure 9C:
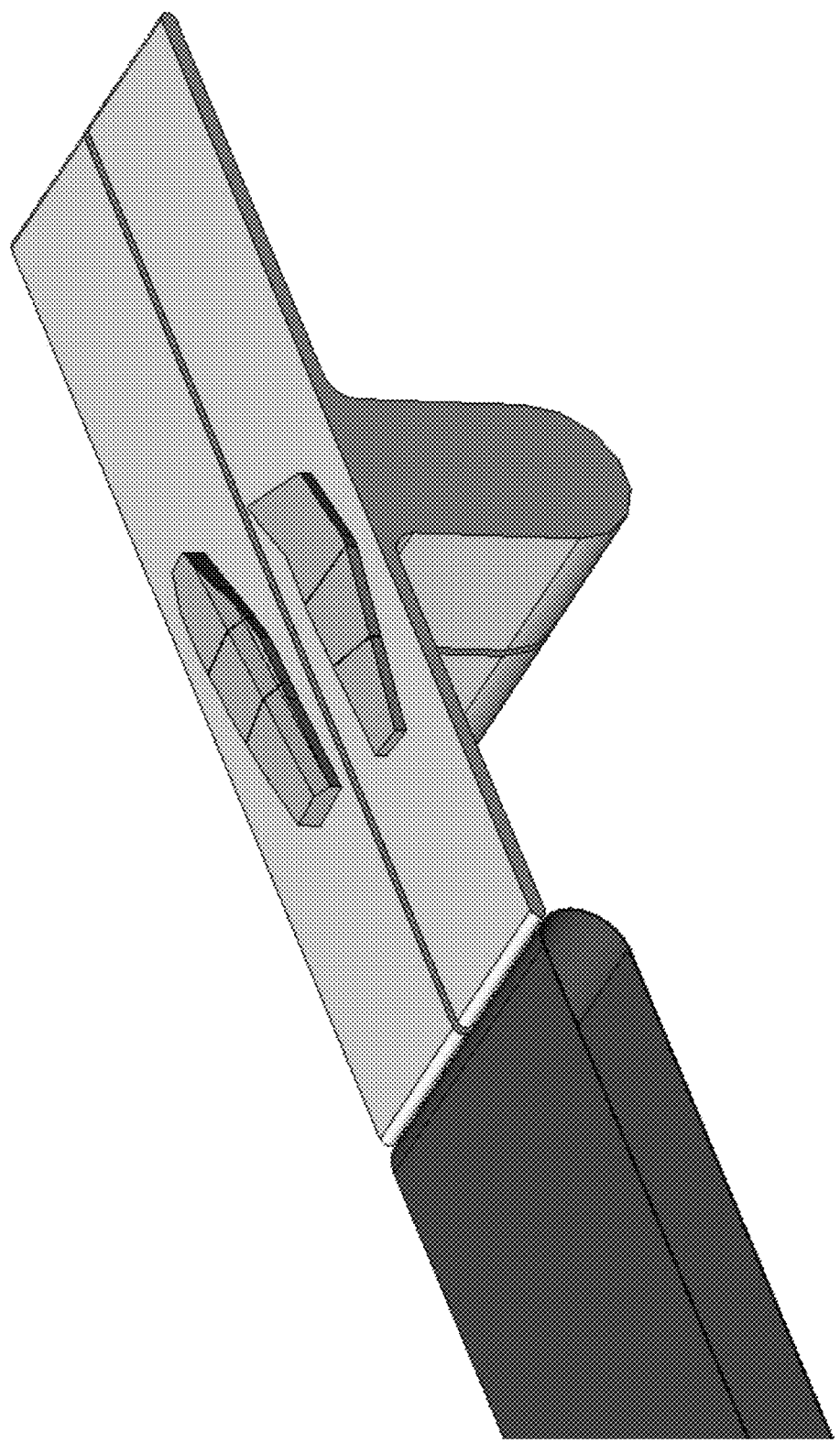
FIG. 9C includes a perspective view of a further represented conveyor system. In this example, a second conveyor and a third conveyor are oriented to follow the first conveyor in its direction of movement. In this example, a grading robot may separate one or more portions of a food article from the remaining portions on the surface of the first conveyor, such that the movement of the conveyor guides the separated portions onto the second conveyor, while guiding the remaining portions onto the third conveyor.
Figure 9D:
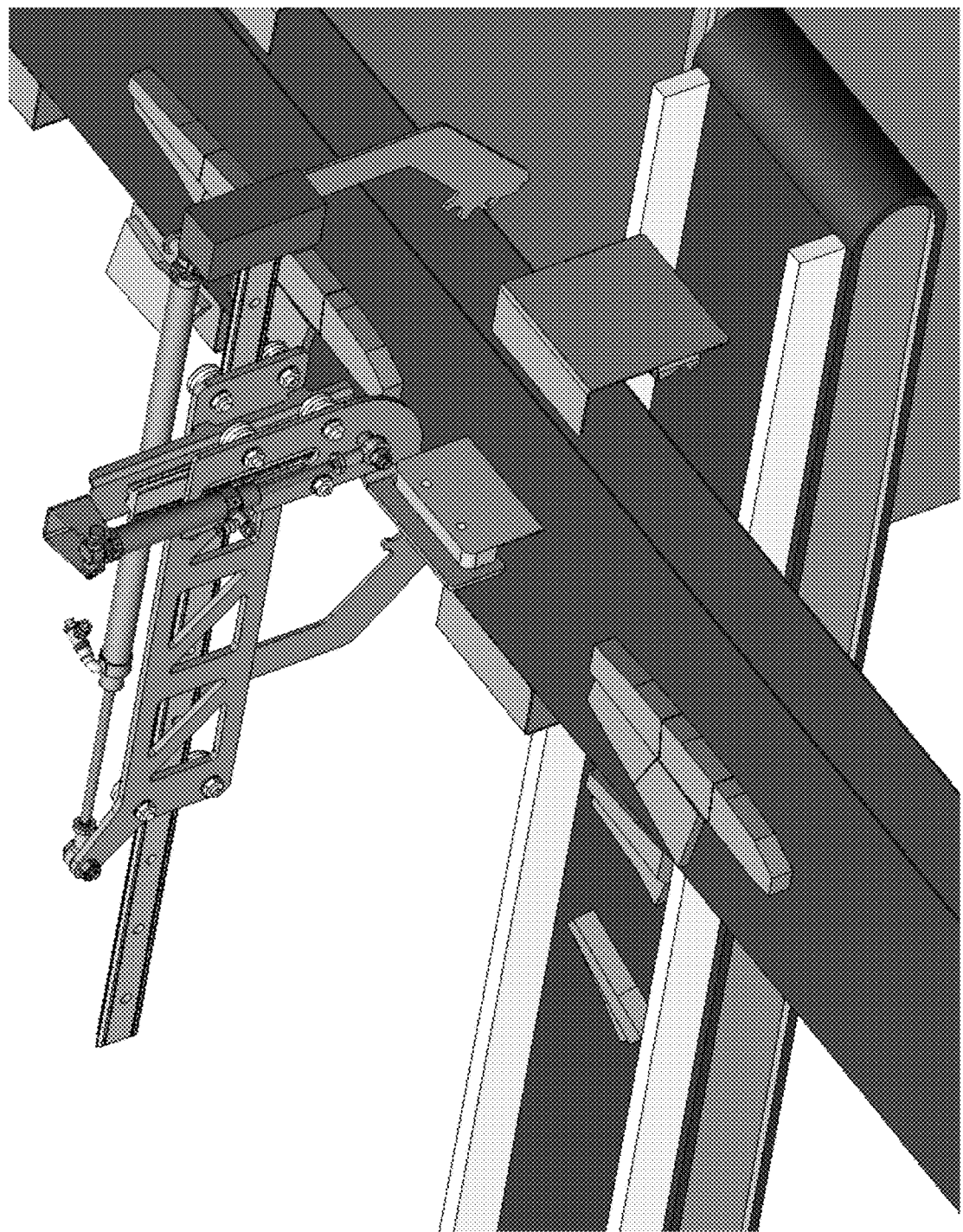
In FIG. 9D, the grading robot transfers portions from the first conveyor to a second conveyor oriented perpendicularly with respect to the first conveyor.
Figure 9E:
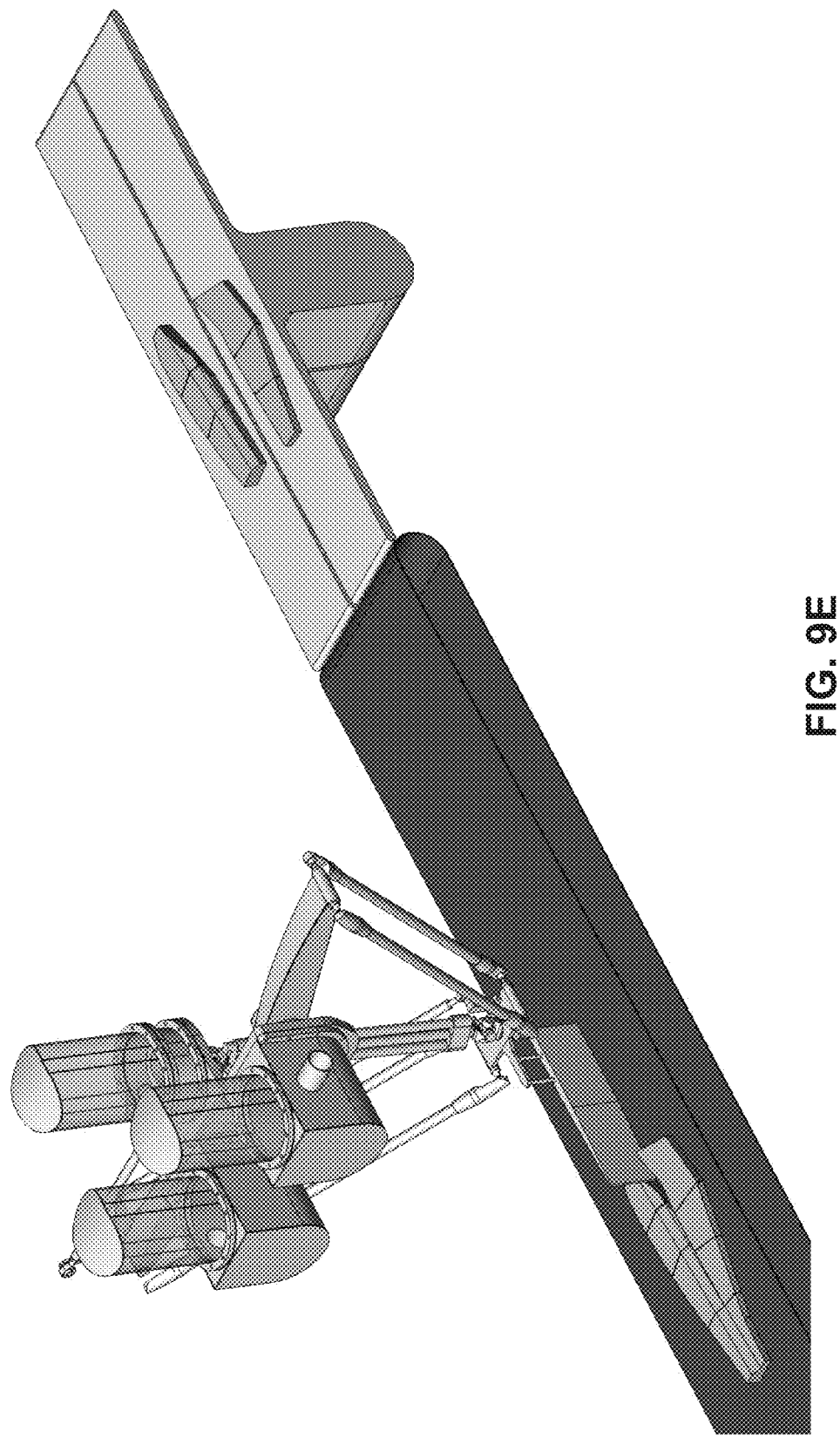
In FIG. 9E, the grading robot transfers portions from the first conveyor to a second and a third conveyor that are oriented to follow the first conveyor in its direction of movement.
Figure 9F:
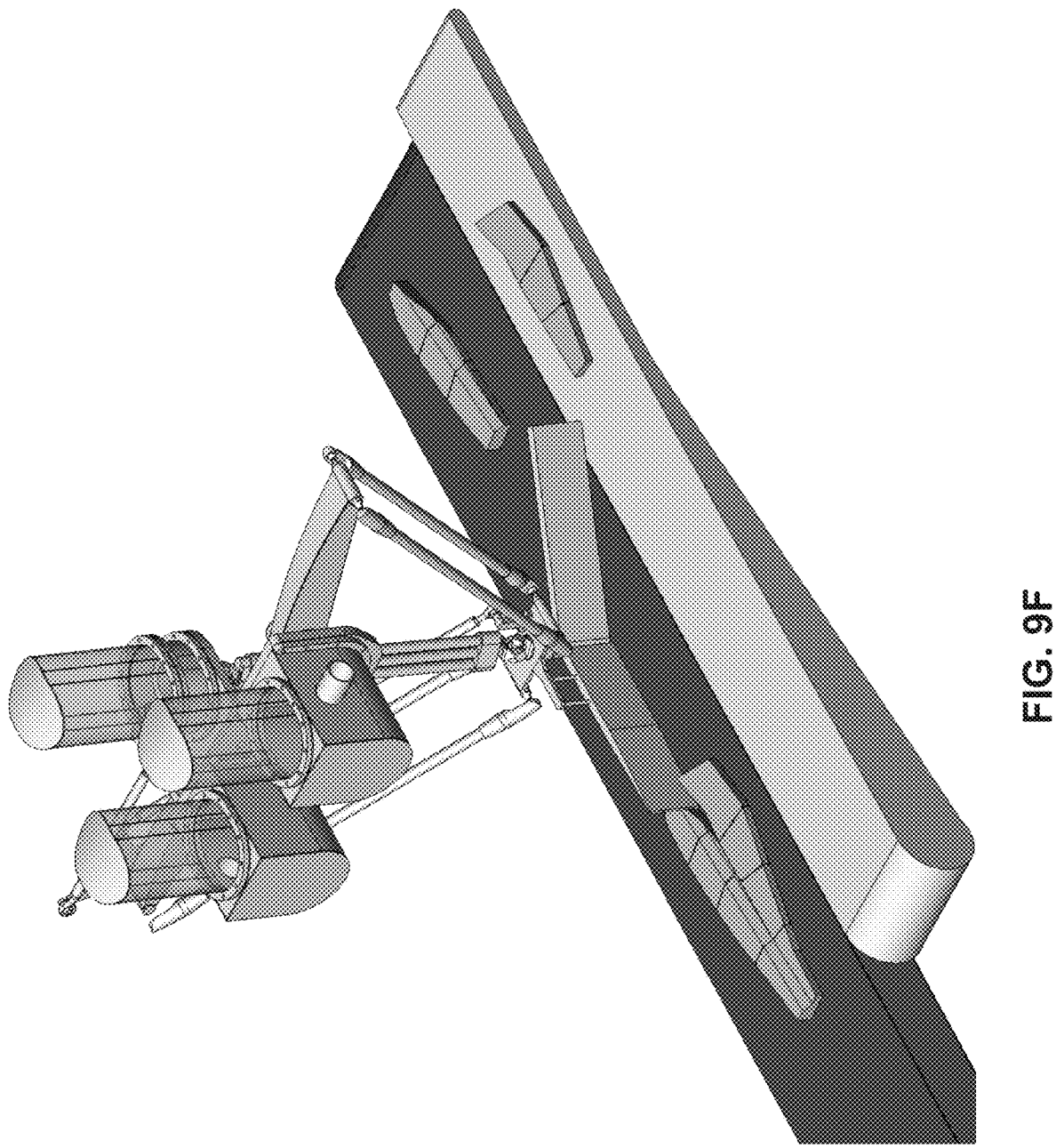
FIG. 9F shows an example of rotation of the second plant being utilized to move portions of the food article from a first to a second conveyor. In this example, rotation of the plate moves a plurality of portions to a second conveyor oriented in parallel and on the right side with respect to the first conveyor.
Figure 9G:
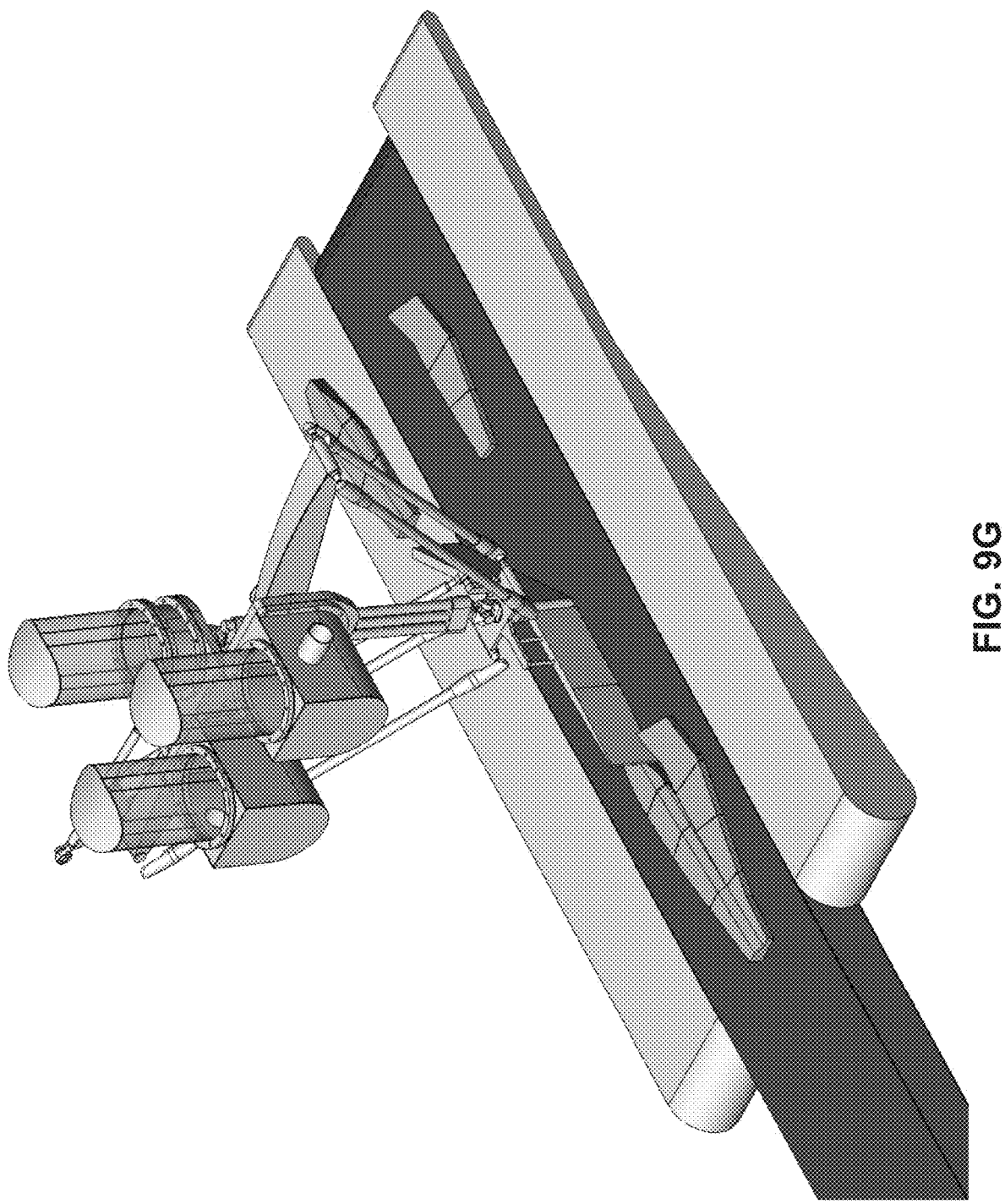
FIG. 9G shows an example of rotation of the second plate being utilized to move portions of the food article from a first to one of two further conveyors. In this example, rotation of the plate in one direction moves a plurality of portions to a second conveyor oriented in parallel and on the left side with respect to the first conveyor. In this example, rotation of the plate in the other direction would move the plurality of portions to a third conveyor oriented in parallel and on the right side with respect to the first conveyor. In some examples, a grading robot comprising a plate may have a further degree of freedom, such that the grading robot can lift diverting plate(s) from the conveyor. This functionality makes simplifies the task of cleaning the plates following use.
Figure 9H:
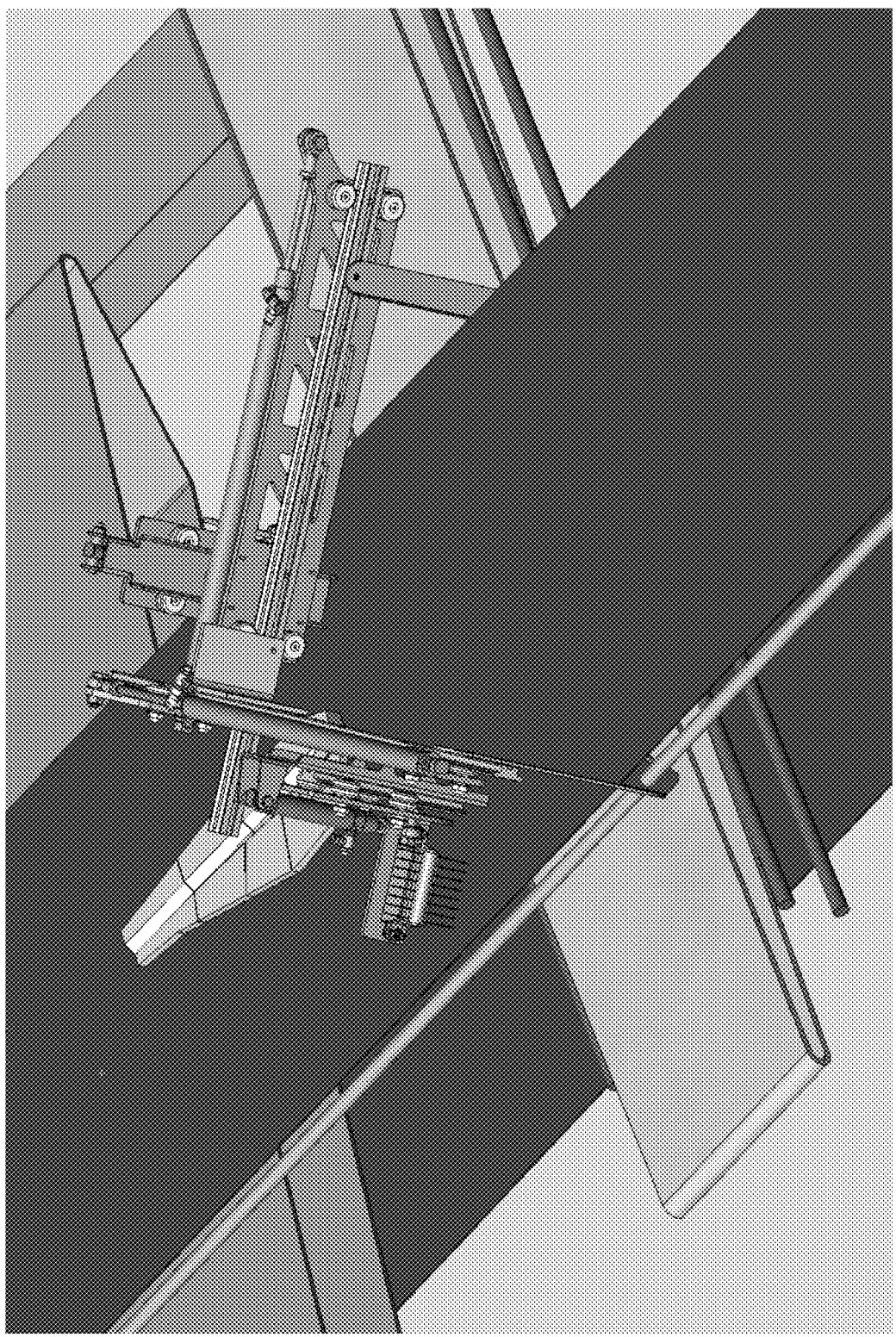
FIG. 9H includes a perspective view of a single degree of freedom grading robot, wherein the vertically movable support member is oriented at an angle with respect to the conveyor, so as to even further minimize the chance of damaging and/or changing the orientation and/or alignment of the other portions of the food article. For example, if the gripped portion(s) is to be moved then the chance of moving further portions is minimized by orienting the vertically movable support member at an angle, such that the gripped portion will be moved away from the further portions when it is moved from its original alignment and orientation on the conveyor.
Figure 9I:
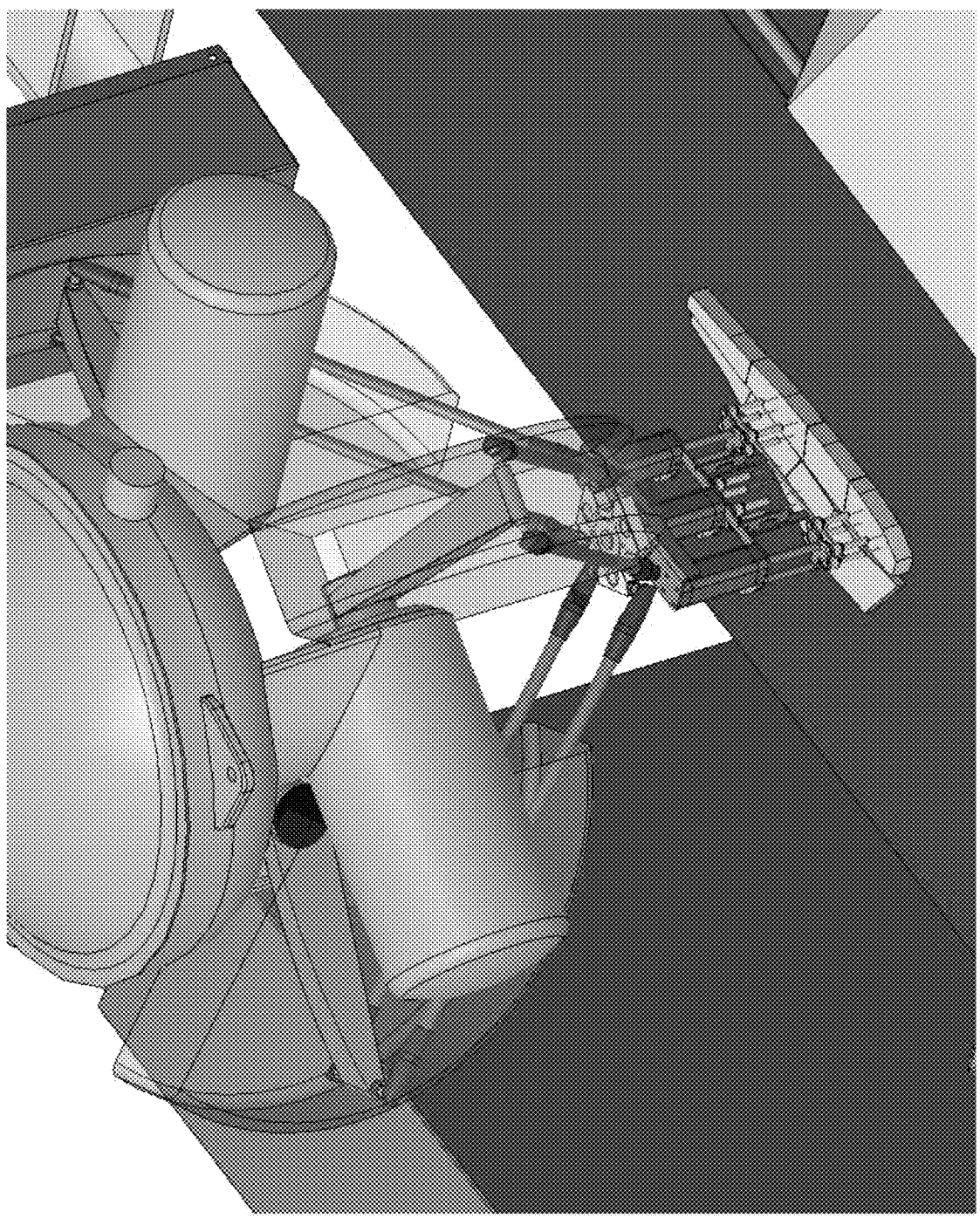
FIGS. 9(D-F) include perspective views of a grading robot with a plate transferring portions of a food article from a first to a second conveyor.
Referring to FIG. 9K, rotation of the vertically movable support member along the fourth degree of freedom moves the first means for moving at least one portion of a food article, with the gripped portion, away from the surface of the conveyor, while also moving a second means for moving at least one portion of a food article into position to grip a further portion.
Figure 9J:
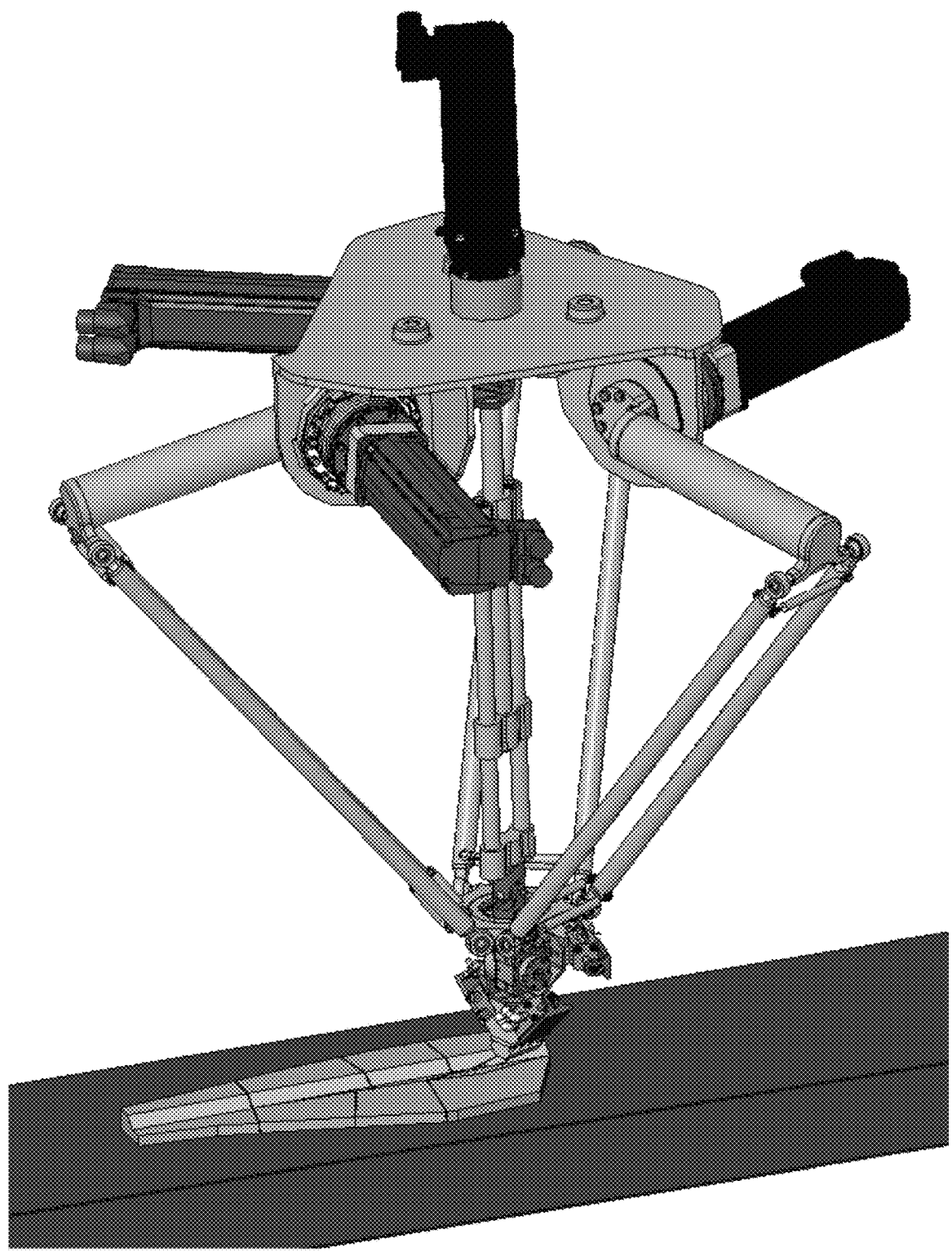
Figure 9K:
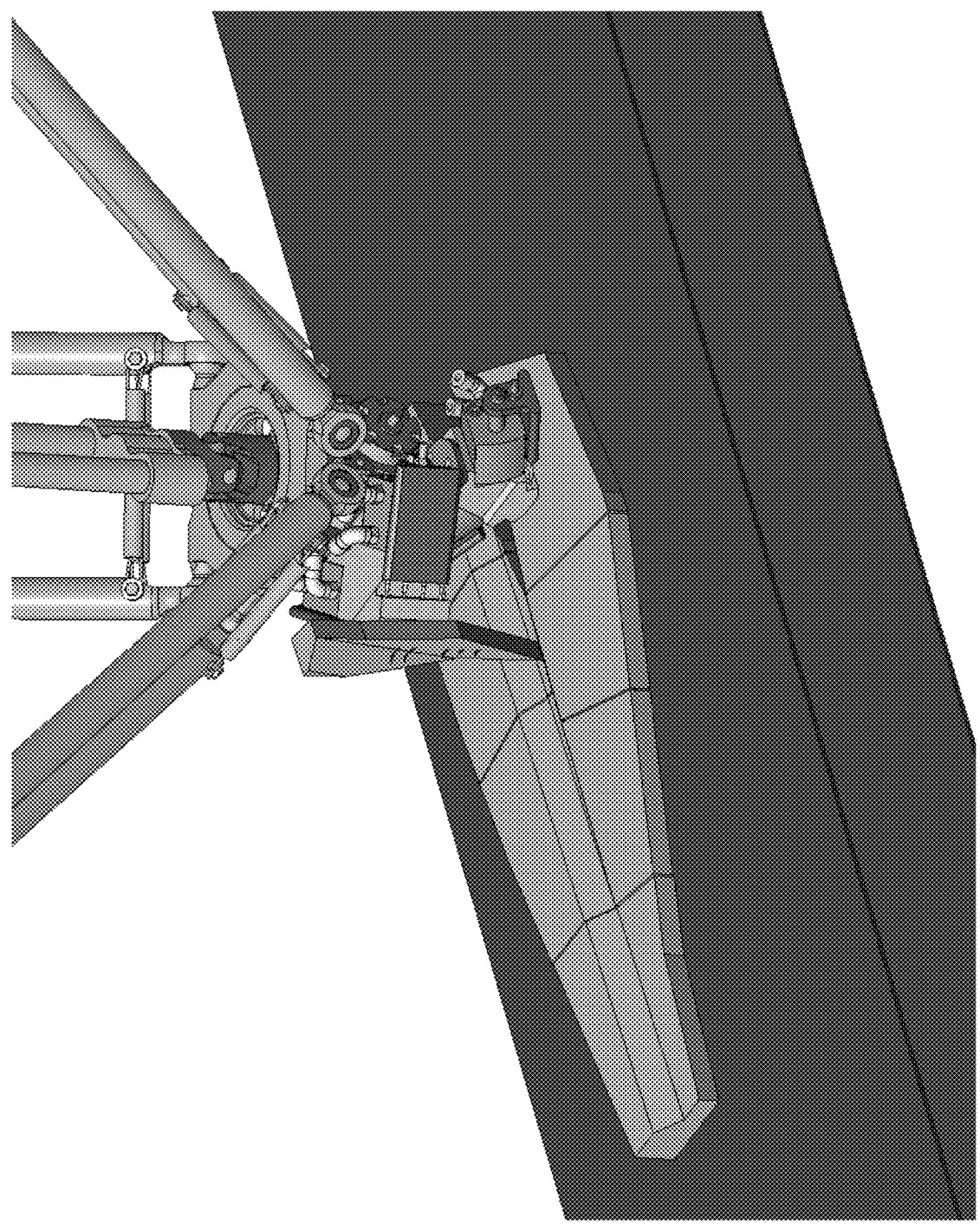

As shown in FIG. 9A, an illustrative two degrees of freedom grading robot 700 according to some embodiments may include a horizontal actuator, for example and without limitation, an air cylinder 702, a plate 704, and a sensor 706. The horizontal air cylinder 702 may be capable of movement in arbitrary positions in the direction perpendicular to the direction of movement of the grading conveyor 218. The sensor 706 provides feedback on the actual horizontal position of the plate 704 to a computer. Based on the estimated location of the portion 117 to be moved, the computer may cause the horizontal air cylinder 702 to move the plate 704 to push the portion 117 to another portion position 256 on the grading conveyor 218, or off of the grading conveyor 218, for example and without limitation, into a tray or bin or onto another conveyor entirely. The pushing plate 704 may be so thin that it can potentially be used to go between certain portions 117 when there are more than one piece parallel on the belt.

In some embodiments, the grading section 122 of the food processing apparatus 100 may include a separating block at any location within the grading section 122. In some embodiments, the separating block may have a triangular shape, and may be suspended above the top surface 164 of the grading conveyor 118, but may be suspended close enough to the top surface 164 of the grading conveyor 118 for the portions 117 of a fish fillet 101 to contact the separating block. In embodiments where the separating block has a triangular shape, the separating block may be pointed (a tip of the triangle pointed) in a direction opposite to the direction in which the grading conveyor 118 is moving. Thus, when a portion 117 of a fish fillet 101 contacts the separating block, the portion 117 may slide along a side of the separating block, and may be moved in a direction perpendicular to the direction in which the grading conveyor 118 is moving and toward an outside edge of the grading conveyor 118, until the portion 117 reaches a base of the separating block. Thus, the separating block may serve to separate portions 117 that are oriented parallel to each other.

In some embodiments, the base of the separating block may have a width less than the width of the grading conveyor 118, such that the separating block may serve to move the portions 117 to different areas of the grading conveyor 118. In some embodiments, the grading section 122 may include secondary conveyors disposed to either side of the grading conveyor 118 in conjunction with a separating block. In such embodiments, the base of the separating block may have a width that is equal to or wider than the width of the conveyor belt, such that when a portion 117 of a fish fillet 101 contacts the separating block, the portion 117 is moved off of the grading conveyor 118 and onto one of the secondary conveyors. In some embodiments, the secondary conveyors may move at a rate faster than the grading conveyor 118 to further separate the portions 117 from each other in a direction parallel to the direction in which the secondary conveyors are moving.

In some embodiments, the grading section 222 may include multiple grading robots 224 that perform different grading functions. For example, a first grading robot 224 may remove portions 117 that contain bones into a tub 258, and a second grading robot 224 may, for example, grade the remaining portions 117 according to type, such as tail portions or loin portions. Furthermore, a third grading robot 224 may, for example, grade each type of portion 117 according to weight. Thus, each portion 117 may be graded according to multiple characteristics. In some embodiments, multiple grading robots 224 may be used to perform a single grading function. For example, multiple grading robots 224 may be used to remove portions 117 having bones, while other multiple grading robots 224 are used to organize the portions 117 according to another characteristic of the portions 117.

In some embodiments, a first group of grading robots 224 may be located on a first sub-conveyor of the grading conveyor 218 and may be controlled by a computer to perform a first function, and a second group of grading robots 224 may be located on a second subsequent sub-conveyor of the grading conveyor 218 and may be controlled by a computer to perform a second function. In particular embodiments, the first sub-conveyor and second sub-conveyor of the grading conveyor 218 may have different widths to accommodate the first and second functions, respectively. In particular embodiments, the grading conveyor 218 may include additional sub-conveyors with respective groups of grading robots 224 that perform yet other functions. In some examples, each sub-conveyor of the grading conveyor 218 may have a plurality of processing conveyors 226 associated with the sub-conveyor.

In some embodiments, the alignment and/or orientation of a portion 117 may need to be changed or adjusted to allow for further processing. For example, for processes having in-feeds perpendicular to a direction in which the grading conveyor 218 is moving ("perpendicular in-feeds"), the portion 117 may need to be oriented such that a length of the portion 117 is oriented perpendicular to a direction in which the perpendicular in-feeds are moving, as shown in FIG. 2. In particular embodiments, the food processing apparatus 200 may include at least one realigning section 800 for each process that needs realignment for the process. A realigning section 800 may include at least one realigning apparatus 802. A realigning apparatus 802 is described in further detail in relation to FIG. 10(A-B).

Figure 10A:
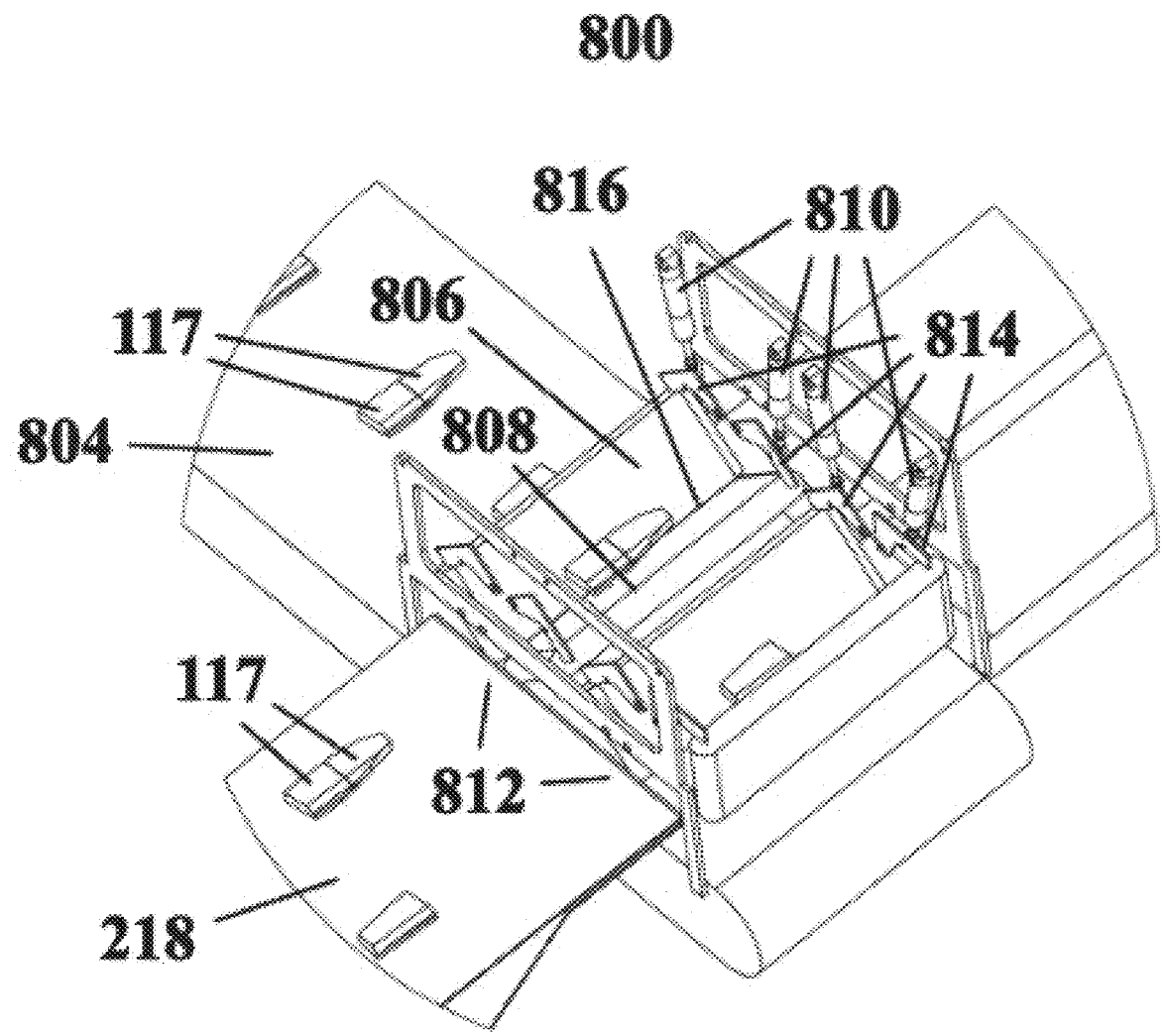
FIG. 10A includes a perspective view of an example of a realigning section comprising realigning apparatus.

FIG. 10A is a top perspective view of a realigning section 800 according to some embodiments. As shown in FIG. 8(A-C), the realigning section 800 may include at least one realigning apparatus 802. The realigning apparatus 802 may be disposed at an end of the grading conveyor 218, and above a perpendicular in-feed processing conveyor 804. The realigning apparatus 802 may include a first mini-conveyor 806, a second mini-conveyor 808, and at least one actuator (e.g., air cylinder 810, motor, linear motor, traditional motor, and solenoid). The first mini-conveyor 806 and second mini-conveyor 808 may be oriented at an acute angle to each other, such that the first mini conveyor 806 and the second mini conveyor 808 form a V-shape. The first mini-conveyor 806 and second mini-conveyor 808 may be mounted above the perpendicular in-feed processing conveyor 804, such that a length of each of the first mini-conveyor 806 and second mini-conveyor 808 is at least substantially perpendicular to a length of the perpendicular in-feed processing conveyor 804, and the direction in which the perpendicular in-feed processing conveyor 804 is moving portions 117.

When the first mini-conveyor 806 and second mini-conveyor 808 are oriented such that the first and second mini-conveyors 806, 808 form a V-shape, a point 816 of the V-shape may be lower than the top surface of the grading conveyor 218, such that portions 117 may come off of the grading conveyor 218 and drop through an open end 812 of the V-shape and into the V-shape formed by first and second mini-conveyors 806, 808.

One or more of the first mini-conveyor 806 and second mini-conveyor 808 may be mounted above the perpendicular in-feed processing conveyor 804 with a hinge member 814, such that the surface of the first mini-conveyor 806 and the surface of the second mini-conveyor 808 may be separated to provide a gap through which a portion 117 may fall. For example, the first mini-conveyor 806 may be mounted above the perpendicular in-feed processing conveyor 804 with a hinge member 814, such that the first mini-conveyor 806 may swing away from the second mini-conveyor 808 and provide a gap through which a portion 117 may fall. In some embodiments, the second mini-conveyor 808 may be mounted above the perpendicular in-feed processing conveyor 804 with a hinge member 814, such that the second mini-conveyor 808 may swing away from the first mini-conveyor 806 and provide a gap through which a portion 117 may fall. In particular embodiments, both the first mini-conveyor 806 and the second mini-conveyor 808 may be mounted above the perpendicular in-feed processing conveyor 804 with a hinge member 814, such that the first mini-conveyor 806 may swing away from the second mini-conveyor 808, and the second mini-conveyor 808 may swing away from the first mini-conveyor 806 to provide a gap through which a portion 117 may fall.

In operation, for example, a portion 117 may have a width and a length, and the length of the portion 117 may be longer than the width. For some processes subsequent to grading, it may be necessary to orient the portion 117, such that the length of the portion 117 is at least substantially perpendicular to the direction in which the processing conveyor 804 is moving. To ensure that the portion 117 is oriented correctly, the first mini-conveyor 806 and second mini-conveyor 808 may be oriented to form the V-shape, in order to receive a portion 117 from the grading conveyor 218. A grading robot 224 may organize the portion 117, such that the portion 117 will be dropped through the open end 812 of the V-shape, and into the V-shape formed be the first mini-conveyor 806 and second mini-conveyor 808. Belts on the first mini-conveyor 806 and second mini-conveyor 808 may rotate to receive the portion 117, and to spread the portion 117 along the first mini-conveyor 806 and second mini-conveyor 808. The V-shape formed by the first mini-conveyor 806 and second mini-conveyor 808 may tend to urge the portion 117 towards the point 816 of the V-shape, and to orient the portion 117 linearly along a length of the first mini-conveyor 806 and second mini-conveyor 808. Furthermore, the V-shape formed by the first mini-conveyor 806 and second mini-conveyor 808 may tend to orient the length of the portion 117, such that the length of the portion 117 is substantially parallel to the lengths of the first mini-conveyor 806 and second mini-conveyor 808, and at least substantially perpendicular to the length of the perpendicular in-feed processing conveyor 804 and the direction in which the perpendicular in-feed processing conveyor 804 is moving portions 117. Thus, when a gap is formed between the first mini-conveyor 806 and second mini-conveyor 808, the portion 117 will drop onto the perpendicular in-feed processing conveyor 804 with the length of the portion 117 oriented substantially perpendicular to the direction in which the perpendicular in-feed processing conveyor 804 is moving portions 117. As discussed above, orienting the lengths of portions 117 to be perpendicular to the direction in which the perpendicular in-feed processing conveyor 804 is moving portions 117 may be necessary for subsequent processes such as packaging and freezing processes.

Figure 10B:
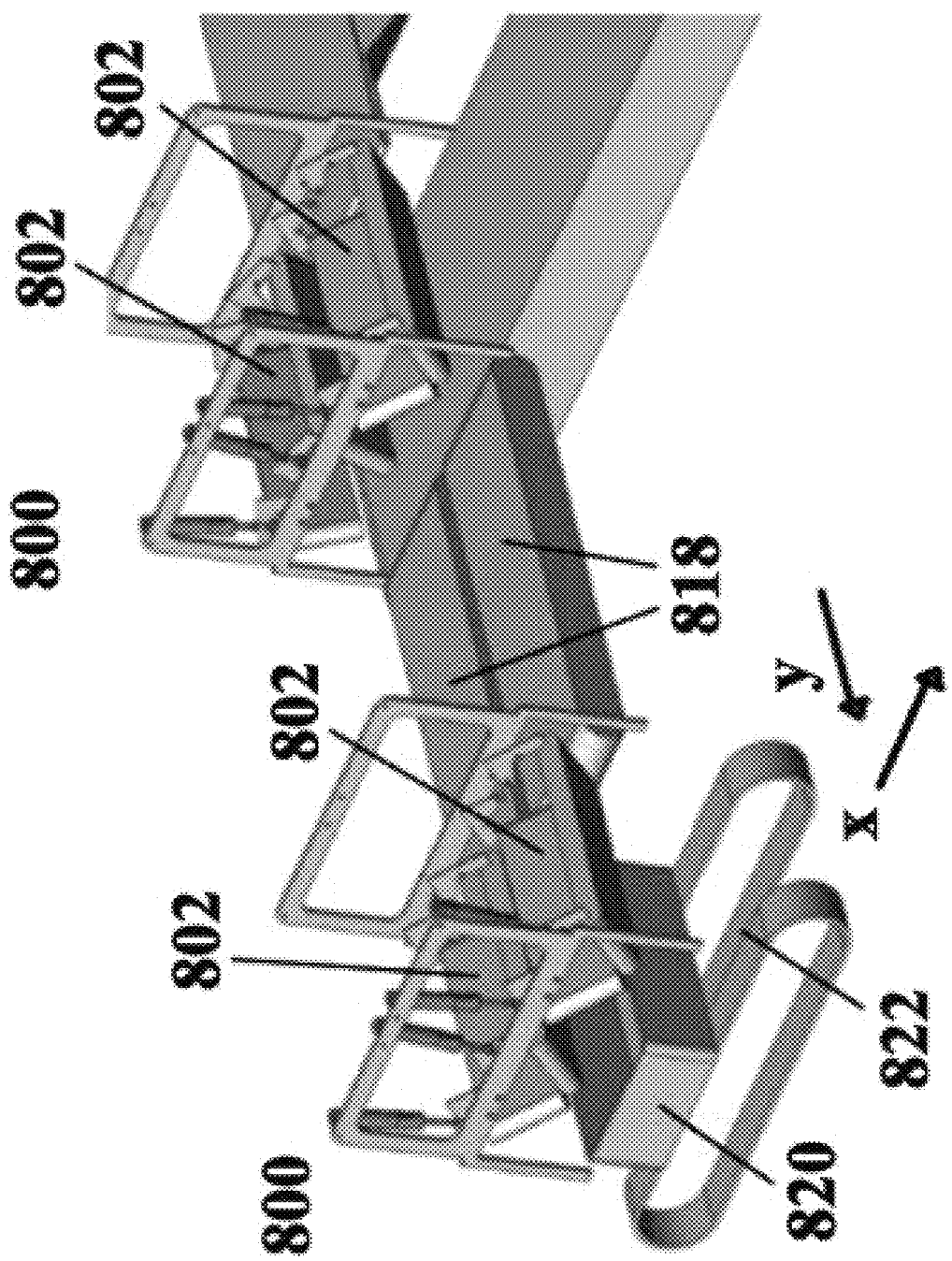
FIG. 10B includes a perspective view of illustrative first and second realigning sections of a food processing apparatus.

As shown in FIG. 10B, a food processing apparatus 200 according to some embodiments may include at least one additional realigning section 800. In particular embodiments, the food processing apparatus 200 comprises at least one additional realigning section 800 to realign a portion when the capacity of the first realigning section 800 is exceeded. A food processing apparatus 200 may include one or more transfer conveyor 818 that directs a portion 117 to the next realigning section 800. A next realigning section may, for example and without limitation, realign a portion 117 onto a next processing conveyor (not shown), or realign a portion 117 into a container 820 that the portion 117 is to be packed in. A food processing apparatus 200 may also include a packing conveyor 822 that can be used to move the container 820 to the correct location to receive the portion 117. In some examples, the packing conveyor 822 moves such that the portion 117 is placed at a specific x-coordinate in the container 820. In some examples, the time at which the realigning apparatus 802 is opened is controlled, such that a specific y-position of the portion 117 in the container 820 is selected. The container 820 may either be filled completely, or partially filled. For example, the container 820 may be partially filled, and a grader (not shown) may be used to fill container 820 completely.

While embodiments of the invention has been illustrated and described in detail in the drawings and foregoing description, such illustration and description are to be considered illustrative or exemplary and not restrictive; the invention is not limited to the particularly described examples. Other variations to the particularly described examples are understood and can effected by those skilled in the art, from a study of the drawings, the specification, and the appended claims. In the specification and claims, the terms "comprising" and "including" are open-ended, and do not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for grading a food article that has been cut into portions, the system comprising:
    a first conveyor;
    a first receiving conveyor and a second receiving conveyor, defining a space therebetween;
    at least one spray-removal robot; and
    a third receiving conveyor,
    wherein the spray-removal robot comprises at least one valve with a nozzle, wherein the valve ejects fluid through the nozzle to impact a food article being moved on the first conveyor toward the third receiving conveyor, such that at least one portion of the food article is moved by the impact through the space between the first receiving conveyor and the second receiving conveyor, and such that at least one portion of the food article is moved by the motion of the first receiving conveyor and the second receiving conveyor to the third receiving conveyor.

2. The system of claim 1, wherein at least one spray-removal robot comprises a plurality of valves with nozzles.

3. The system claim 2, wherein each of the plurality of valves with nozzles is independently controllable.

4. The system of any of claims 1-3, wherein the at least one spray-removal robot is a plurality of spray-removal robots.

5. The system of any of claims 1-3, wherein the first receiving conveyor and the second receiving conveyor are movable in a direction substantially perpendicular to the movement of the first conveyor.

6. The system of claim 5, wherein the movement of the first receiving conveyor and the movement of the second receiving conveyor are independently controllable.

7. The system of any of claims 1-3, wherein the movement of the first receiving conveyor and the movement of the second receiving conveyor are controlled by a computer that controls the at least one spray-removal robot.

8. The system of any of claims 1-3, wherein the first receiving conveyor and the second receiving conveyor are rollers.

9. The system of any of claims 1-3, wherein the first receiving conveyor and the second receiving conveyor, defining a space therebetween, is substantially as shown in FIG. 8B or FIG. 8C.

10. The system of any of claims 1-3, further comprising a laser sensor.

11. A food processing apparatus comprising:
    a cutting machine;
    at least one conveyor configured to move a food article to the cutting machine; and
    the system of any of claims 1-3 configured to grade the for grading a food article that has been cut into portions by the cutting machine.

12. The food processing apparatus of claim 11, further comprising:
    at least one imaging system;
    at least one realigning apparatus;
    at least one x-ray machine;
    at least one manual quality check station;
    at least one automated quality check station;
    at least one additional grading device; or
    at least one realigning apparatus,
    or any combination thereof.

13. The food processing apparatus of claim 12, wherein at least one additional grading device is a needle grading device, a gripper grading device, a two degrees of freedom grading device, a three degrees of freedom grading device, or a four degrees of freedom grading device.

14. The food processing apparatus of claim 11, further comprising at least one computer programmed to operate the spray-removal robot according to one or more inputs selected from the group consisting of an x-ray image, 3D image, a signal from a cutting robot, a movement of the first conveyor, and a movement of any other conveyor(s) preceding the spray-removal robot.

15. A method for grading a food article that has been cut into portions, the method comprising utilizing the system of any of claims 1-3 to remove at least one of the portions of the food article through the space defined between the first receiving conveyor and the second receiving conveyor, while transferring remaining portions of the food article to the third receiving conveyor.

16. The method according to claim 15, wherein the action of at least one spray-removal robot is controlled by a computer according to a determination of a location of the portion to be removed, wherein the computer determines a location of the portion to be removed from one or more inputs selected from the group consisting of an x-ray image, 3D image, a signal from a cutting robot, the movement of the grading conveyor, and the movement of any other conveyor (s) preceding the at least one spray-removal robot.

17. The method according to claim 15, wherein each of the portions has an alignment and orientation with respect to a surface of the first conveyor, and are positioned parallel to each other on the surface of the first conveyor,
    wherein none of the portions that are not removed and are positioned parallel to each other on the surface of the first conveyor are substantially moved during the removal of the portion through the space defined between the first receiving conveyor and the second receiving conveyor, and
    wherein the alignments and orientations of the portions that are not removed and are positioned parallel to each other on the surface of the first conveyor are substantially maintained after the removal of the portion through the space defined between the first receiving conveyor and the second receiving conveyor, and the transfer of the remaining portions that are not removed to the third receiving conveyor.

18. The method according to claim 17, wherein the portion that is removed is closely adjoined on opposing sides in an orientation substantially perpendicular to the parallel orientation of the plurality of portions by other portions.

19. The method according to claim 15, further comprising selecting at least one portion to be removed based on at least one criteria selected from the group consisting of size, weight, quality, and type.

20. The method according to claim 19, wherein at least one criteria is based on whether the at least one portion comprises bones.

* * * * *